US012760298B2

(12) United States Patent
Chandhoke et al.

(10) Patent No.: US 12,760,298 B2
(45) Date of Patent: Oct. 13, 2026

(54) TECHNOLOGIES USEFUL FOR ASSESSING PERMEABILITY

(71) Applicant: Parabilis Medicines, Inc., Cambridge, MA (US)

(72) Inventors: Amrita Singh Chandhoke, Boston, MA (US); James Andrew Madsen, Medford, MA (US); Yue-Mei Zhang, Wellesley, MA (US); John Hanney McGee, Somerville, MA (US); Marco Peter Fekkes, Waltham, MA (US)

(73) Assignee: PARABILIS MEDICINES, INC., Cambridge, MA (US)

( * ) Notice: Subject to any disclaimer, the term of this patent is extended or adjusted under 35 U.S.C. 154(b) by 1003 days.

(21) Appl. No.: 17/784,482

(22) PCT Filed: Dec. 11, 2020

(86) PCT No.: PCT/US2020/064685
§ 371 (c)(1),
(2) Date: Jun. 10, 2022

(87) PCT Pub. No.: WO2021/119537
PCT Pub. Date: Jun. 17, 2021

(65) Prior Publication Data

US 2023/0046728 A1 Feb. 16, 2023

Related U.S. Application Data

(60) Provisional application No. 62/946,736, filed on Dec. 11, 2019.

(51) Int. Cl.

| | |
|---|---|
| ***C07K 7/06*** | (2006.01) |
| ***C07K 7/08*** | (2006.01) |
| ***C12N 9/14*** | (2006.01) |
| ***C12N 15/10*** | (2006.01) |
| ***C40B 40/10*** | (2006.01) |

(52) U.S. Cl.
CPC ............ *C12N 15/1034* (2013.01); *C07K 7/06* (2013.01); *C07K 7/08* (2013.01); *C12N 9/14* (2013.01); *C40B 40/10* (2013.01); *C12Y 308/01005* (2013.01)

(58) Field of Classification Search
CPC .............................. C12N 15/1034; C07K 7/06
See application file for complete search history.

(56) References Cited

U.S. PATENT DOCUMENTS

| | | | |
|---|---|---|---|
| 7,112,552 | B2 | 9/2006 | Simpson et al. |
| 7,354,750 | B2 | 4/2008 | Simpson et al. |
| 7,429,472 | B2 | 9/2008 | Darzins et al. |
| 7,888,086 | B2 | 2/2011 | Darzins et al. |
| 7,960,506 | B2 | 6/2011 | Nash |
| 8,592,377 | B2 | 11/2013 | Verdine et al. |
| 8,957,026 | B2 | 2/2015 | Verdine et al. |
| 9,163,330 | B2 | 10/2015 | Verdine et al. |
| 9,556,227 | B2 | 1/2017 | Verdine et al. |
| 9,617,309 | B2 | 4/2017 | Verdine et al. |
| 10,081,654 | B2 | 9/2018 | Verdine et al. |
| 10,227,390 | B2 | 3/2019 | Verdine et al. |
| 10,301,351 | B2 | 5/2019 | Verdine et al. |
| 10,533,039 | B2 | 1/2020 | Verdine et al. |
| 11,198,713 | B2 | 12/2021 | Hilinski et al. |
| 11,332,496 | B2 | 5/2022 | Verdine et al. |
| 11,377,476 | B2 | 7/2022 | Verdine et al. |
| 2015/0225471 | A1 | 8/2015 | Liang et al. |
| 2016/0257725 | A1 | 9/2016 | Verdine et al. |
| 2018/0009847 | A1 | 1/2018 | Verdine et al. |
| 2018/0010001 | A1 | 1/2018 | Hersam et al. |
| 2018/0188260 | A1* | 7/2018 | Kritzer ..................... C12Q 1/32 |
| 2018/0208627 | A1* | 7/2018 | Zhao ........................ A61P 35/00 |
| 2018/0209960 | A1 | 7/2018 | Watt et al. |
| 2019/0085305 | A1 | 3/2019 | Darzins et al. |
| 2019/0202862 | A1 | 7/2019 | Verdine et al. |
| 2020/0247858 | A1 | 8/2020 | Hilinski et al. |
| 2022/0213154 | A1 | 7/2022 | Hilinski et al. |
| 2023/0137773 | A1 | 5/2023 | Verdine et al. |
| 2023/0271917 | A1 | 8/2023 | Jewett et al. |
| 2023/0357320 | A1 | 11/2023 | Verdine et al. |

FOREIGN PATENT DOCUMENTS

| | | | |
|---|---|---|---|
| EP | 0353460 | A2 | 2/1990 |
| WO | WO-2005/044839 | A2 | 5/2005 |
| WO | WO-2006/093529 | A2 | 9/2006 |
| WO | WO-2008/061192 | A2 | 5/2008 |
| WO | WO-2008/095063 | A1 | 8/2008 |

(Continued)

OTHER PUBLICATIONS

England et al., 2015, HaloTag® Technology: A Versatile Platform for Biomedical Applications, Bioconjugate Chem, 26: 975-986.*
Peraro et al., 2018, Cell Penetration Profiling Using the Chloroalkane Penetration Assay, J Am Chem Soc, 140(36): 11360-11369.*
Chandra, A. et al., A novel fluorescence-based cellular permeability assay, J. Biochem. Biophys. Methods, 70:329-333 (2007).
Chang, Y. S. et al., Stapled a-helical peptide drug development: A potent dual inhibitor of MDM2 and MDMX for p53-dependent cancer therapy, PNAS, E3445-E3454 (2013).
Horvath, R. et al., Molecular Interaction of a New Antibacterial Polymer with a Supported Lipid Bilayer Measured by an in situ Label-Free Optical Technique, Int. J. Mol. Sci., 14:9722- 9736 (2013).

(Continued)

*Primary Examiner* — Amber D Steele
(74) *Attorney, Agent, or Firm* — Choate, Hall & Stewart LLP; Xiaodong Li; William C. Howland, III

(57) ABSTRACT

In some embodiments, the invention relates to methods and reagents for the identification of compounds that traverse the cell membrane of an animal cell. In some embodiments, the invention provides additional methods for determining if a candidate compound that traverses an animal cell membrane is able to modulate an intracellular target, as well as reagents and kits for reagents and kits for performing the disclosed methods.

5 Claims, 26 Drawing Sheets

Specification includes a Sequence Listing.

(56) References Cited

FOREIGN PATENT DOCUMENTS

| | | | | |
|---|---|---|---|---|
| WO | WO-2008/121767 A2 | | 10/2008 | |
| WO | WO-2008/137633 A2 | | 11/2008 | |
| WO | WO-2009/042237 A2 | | 4/2009 | |
| WO | WO-2009/108261 A2 | | 9/2009 | |
| WO | WO-2010/011313 A2 | | 1/2010 | |
| WO | WO-2010/042225 A2 | | 4/2010 | |
| WO | WO-2010/068684 A2 | | 6/2010 | |
| WO | WO-2010/070232 A1 | | 6/2010 | |
| WO | WO-2010/148335 A2 | | 12/2010 | |
| WO | WO-2011/008260 A2 | | 1/2011 | |
| WO | WO-2011/094708 A2 | | 8/2011 | |
| WO | WO-2012/006598 A2 | | 1/2012 | |
| WO | WO-2012/065181 A2 | | 5/2012 | |
| WO | WO-2012/142604 A2 | | 10/2012 | |
| WO | WO-2012/159164 A1 | | 11/2012 | |
| WO | WO-2012/174409 A1 | | 12/2012 | |
| WO | WO-2012/174423 A1 | | 12/2012 | |
| WO | WO-2013/055949 A2 | | 4/2013 | |
| WO | WO-2013/102211 A2 | | 7/2013 | |
| WO | WO-2013/142281 A1 | | 9/2013 | |
| WO | WO-2013150338 A1 | * | 10/2013 | ........... C07K 14/001 |
| WO | WO-2014/052647 A2 | | 4/2014 | |
| WO | WO-2014/055564 A1 | | 4/2014 | |
| WO | WO-2014/144148 A1 | | 9/2014 | |
| WO | WO-2014/144768 A2 | | 9/2014 | |
| WO | WO-2014/151369 A2 | | 9/2014 | |
| WO | WO-2014/159969 A1 | | 10/2014 | |
| WO | WO-2014/197821 A1 | | 12/2014 | |
| WO | WO-2014/201370 A1 | | 12/2014 | |
| WO | WO-2015/051030 A2 | | 4/2015 | |
| WO | WO-2015/179635 A2 | | 11/2015 | |
| WO | WO-2015/179691 A2 | | 11/2015 | |
| WO | WO-2016/149613 A2 | | 9/2016 | |
| WO | WO-2017/004591 A2 | | 1/2017 | |
| WO | WO-2017/040323 A2 | | 3/2017 | |
| WO | WO-2017/040329 A2 | | 3/2017 | |
| WO | WO-2019/051327 A2 | | 3/2019 | |
| WO | WO-2019157131 A1 | * | 8/2019 | ............... C07K 7/06 |
| WO | WO-2020/041270 A1 | | 2/2020 | |
| WO | WO-2021/188659 A1 | | 9/2021 | |
| WO | WO-2022/020651 A1 | | 1/2022 | |
| WO | WO-2022/020652 A2 | | 1/2022 | |
| WO | WO-2022/261257 A1 | | 12/2022 | |

OTHER PUBLICATIONS

International Search Report for PCT/US2020/064685, 4 pages (mailed Mar. 24, 2021).

Los, G. V. et al., HaloTag: A Novel Protein Labeling Technology for Cell Imaging and Protein Analysis, ACS Chem. Bio., 3(6):373-382 (2008).

Peraro, L. et al., Diversity-Oriented Stapling Yields Intrinsically Cell-Penetrant Inducers of Autophagy, J. Am. Chem. Soc., 139:7792-7802 (2017).

Schafmeister et al., An All-Hydrocarbon Cross-Linking System for Enhancing the Helicity and Metabolic Stability of Peptides, J. Am. Chem. Soc., 122: 5891-5892 (2000).

Shin, D-S. et al., Combinatorial Solid Phase Peptide Synthesis and Bioassays, Jrnl. Biochem. Mol. Bio., 38(5):517-525 (2005).

Urh, M. and Rosenberg, M., HaloTag, a Platform Technology for Protein Analysis, Curr. Chem. Geno., 6(Suppl 1-M8):72-78 (2012).

Written Opinion for PCT/US2020/064685, 29 pages (mailed Mar. 24, 2021).

Yang, Y., Design of cleavable linkers and applications in chemical proteomics, Doctoral thesis (Technical University of Munich), 11-17 (2014), <https://mediatum.ub.tum.de/doc/1186015/file.pdf>.

Ye, G et al., Bilayer disruption and liposome restructuring by a homologous series of small Arg-rich synthetic peptides, Colloids and Surfaces B: Biointerfaces, 76(1):76-81 (2010).

Kohl, J. et al., Ultrafast tissue staining with chemical tags, PNAS, E3805-E3814 (2014).

Peraro, L. et al., Cell Penetration Profiling Using the Chloroalkane Penetration Assay, J. Am. Chem. Soc., 140(36):11360-11369 (2018).

* cited by examiner

Complex

Disruption of complex
by base hydrolysis
in pH ≥ 11.0

Candidate Compound (R) attached to releasing moiety

Representative examples of FG1 and FG2

*Compound 1-Cl*

Candidate compound 1 attached to binding moiety

*Compound 1-OH*

Candidate compound 1 attached to releasing moiety

SEQUENCE LISTING

<160> NUMBER OF SEQ ID NOS: 88

<210> SEQ ID NO 1
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NH2
modifications. See specification as filed for detailed
description of modifications and preferred embodiments.

<400> SEQUENCE: 1

-continued

```
Leu Thr Phe Ala Tyr Trp Ala Gln Ser Ala Ala
1               5                   10


<210> SEQ ID NO 2
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NH2
      modifications.  See specification as filed for detailed
      description of modifications and preferred embodiments.

<400> SEQUENCE: 2

Leu Thr Phe Glu Tyr Trp Ala Gln Ser Ala Ala
1               5                   10


<210> SEQ ID NO 3
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NH2
      modifications.  See specification as filed for detailed
      description of modifications and preferred embodiments.

<400> SEQUENCE: 3

Leu Thr Phe Thr Tyr Trp Ala Gln Ser Ala Ala
1               5                   10


<210> SEQ ID NO 4
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NHMe
      modifications.  See specification as filed for detailed
      description of modifications and preferred embodiments.

<400> SEQUENCE: 4

Leu Thr Phe Ala Tyr Trp Ala Gln Ser Ala Ala
1               5                   10


<210> SEQ ID NO 5
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NHMe
      modifications.  See specification as filed for detailed
      description of modifications and preferred embodiments.

<400> SEQUENCE: 5

Leu Thr Phe Glu Tyr Trp Ala Gln Ser Ala Ala
1               5                   10
```

<210> SEQ ID NO 6
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTag02, R8, Cba, S5 and NHMe
      modifications.  See specification as filed for detailed
      description of modifications and preferred embodiments.

<400> SEQUENCE: 6

Leu Thr Phe Thr Tyr Trp Ala Gln Ser Ala Ala
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTag02, R8, Cba, S5 and NH2
      modifications.  See specification as filed for detailed
      description of modifications and preferred embodiments.

<400> SEQUENCE: 7

Leu Thr Phe Glu Tyr Trp Ala Ala Ser Ala Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTag02, R8, Cba, S5 and NH2
      modifications.  See specification as filed for detailed
      description of modifications and preferred embodiments.

<400> SEQUENCE: 8

Leu Thr Phe Glu Tyr Trp Ala Thr Ser Ala Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTag02, R8, Cba, S5 and NHMe
      modifications.  See specification as filed for detailed
      description of modifications and preferred embodiments.

<400> SEQUENCE: 9

Leu Thr Phe Glu Tyr Trp Ala Ala Ser Ala Ala
1               5                   10

<210> SEQ ID NO 10

<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NHMe modifications. See specification as filed for detailed description of modifications and preferred embodiments.

<400> SEQUENCE: 10

Leu Thr Phe Glu Tyr Trp Ala Gln Ser Ala Ala
1 5 10

<210> SEQ ID NO 11
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NHMe modifications. See specification as filed for detailed description of modifications and preferred embodiments.

<400> SEQUENCE: 11

Leu Thr Phe Glu Tyr Trp Ala Thr Ser Ala Ala
1 5 10

<210> SEQ ID NO 12
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NH2 modifications. See specification as filed for detailed description of modifications and preferred embodiments.

<400> SEQUENCE: 12

Leu Thr Phe Ala Tyr Trp Ala Gln Ser Ala Ala
1 5 10

<210> SEQ ID NO 13
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NH2 modifications. See specification as filed for detailed description of modifications and preferred embodiments.

<400> SEQUENCE: 13

Leu Thr Phe Glu Tyr Trp Ala Gln Ser Ala Ala
1 5 10

<210> SEQ ID NO 14
<211> LENGTH: 11
<212> TYPE: PRT
<213> ORGANISM: Artificial Sequence

```
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NH2
      modifications.  See specification as filed for detailed
      description of modifications and preferred embodiments.

<400> SEQUENCE: 14

Leu Thr Phe Thr Tyr Trp Ala Gln Ser Ala Ala
1               5                   10


<210> SEQ ID NO 15
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe
      modifications.  See specification as filed for detailed
      description of modifications and preferred embodiments.

<400> SEQUENCE: 15

Leu Thr Phe Ala Tyr Trp Ala Gln Ser Ala Ala
1               5                   10


<210> SEQ ID NO 16
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe
      modifications.  See specification as filed for detailed
      description of modifications and preferred embodiments.

<400> SEQUENCE: 16

Leu Thr Phe Glu Tyr Trp Ala Gln Ser Ala Ala
1               5                   10


<210> SEQ ID NO 17
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe
      modifications.  See specification as filed for detailed
      description of modifications and preferred embodiments.

<400> SEQUENCE: 17

Leu Thr Phe Thr Tyr Trp Ala Gln Ser Ala Ala
1               5                   10


<210> SEQ ID NO 18
<211> LENGTH: 11
<212> TYPE: PRT
<213> ORGANISM: Artificial Sequence
<220> FEATURE:
<223> OTHER INFORMATION: Synthetic
<220> FEATURE:
```

<221> NAME/KEY: misc_feature
<222> LOCATION: (1)..(11)
<223> OTHER INFORMATION: Contains HaloTagO2, ReN, Cba, Az and NH2
modifications. See specification as filed for detailed
description of modifications and preferred embodiments.

<400> SEQUENCE: 18

Leu Thr Phe Glu Tyr Trp Ala Ala Ser Ala Ala
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NH2
modifications. See specification as filed for detailed
description of modifications and preferred embodiments.

<400> SEQUENCE: 19

Leu Thr Phe Glu Tyr Trp Ala Thr Ser Ala Ala
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe
modifications. See specification as filed for detailed
description of modifications and preferred embodiments.

<400> SEQUENCE: 20

Leu Thr Phe Glu Tyr Trp Ala Ala Ser Ala Ala
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe
modifications. See specification as filed for detailed
description of modifications and preferred embodiments.

<400> SEQUENCE: 21

Leu Thr Phe Glu Tyr Trp Ala Gln Ser Ala Ala
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe modifications. See specification as filed for detailed description of modifications and preferred embodiments.

<400> SEQUENCE: 22

Leu Thr Phe Glu Tyr Trp Ala Thr Ser Ala Ala
1 5 10

<210> SEQ ID NO 23
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, R8, Cba, S5 and NH2 modifications. See specification as filed for detailed description of modifications and preferred embodiments.

<400> SEQUENCE: 23

Leu Thr Phe Ala Tyr Trp Ala Gln Ser Ala Ala
1 5 10

<210> SEQ ID NO 24
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, R8, Cba, S5 and NH2 modifications. See specification as filed for detailed description of modifications and preferred embodiments.

<400> SEQUENCE: 24

Leu Thr Phe Glu Tyr Trp Ala Gln Ser Ala Ala
1 5 10

<210> SEQ ID NO 25
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, R8, Cba, S5 and NH2 modifications. See specification as filed for detailed description of modifications and preferred embodiments.

<400> SEQUENCE: 25

Leu Thr Phe Thr Tyr Trp Ala Gln Ser Ala Ala
1 5 10

<210> SEQ ID NO 26
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, R8, Cba, S5 and NHMe modifications. See specification as filed for detailed description of modifications and preferred embodiments.

-continued

<400> SEQUENCE: 26

Leu Thr Phe Ala Tyr Trp Ala Gln Ser Ala Ala
1 5 10

<210> SEQ ID NO 27
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, R8, Cba, S5 and NHMe modifications. See specification as filed for detailed description of modifications and preferred embodiments.

<400> SEQUENCE: 27

Leu Thr Phe Glu Tyr Trp Ala Gln Ser Ala Ala
1 5 10

<210> SEQ ID NO 28
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, R8, Cba, S5 and NHMe modifications. See specification as filed for detailed description of modifications and preferred embodiments.

<400> SEQUENCE: 28

Leu Thr Phe Thr Tyr Trp Ala Gln Ser Ala Ala
1 5 10

<210> SEQ ID NO 29
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, R8, Cba, S5 and NH2 modifications. See specification as filed for detailed description of modifications and preferred embodiments.

<400> SEQUENCE: 29

Leu Thr Phe Glu Tyr Trp Ala Ala Ser Ala Ala
1 5 10

<210> SEQ ID NO 30
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, R8, Cba, S5 and NH2 modifications. See specification as filed for detailed description of modifications and preferred embodiments.

<400> SEQUENCE: 30

Leu Thr Phe Glu Tyr Trp Ala Thr Ser Ala Ala 1 5 10

<210> SEQ ID NO 31
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, R8, Cba, S5 and NHMe modifications. See specification as filed for detailed description of modifications and preferred embodiments.

<400> SEQUENCE: 31

Leu Thr Phe Glu Tyr Trp Ala Ala Ser Ala Ala
1 5 10

<210> SEQ ID NO 32
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, R8, Cba, S5 and NHMe modifications. See specification as filed for detailed description of modifications and preferred embodiments.

<400> SEQUENCE: 32

Leu Thr Phe Glu Tyr Trp Ala Gln Ser Ala Ala
1 5 10

<210> SEQ ID NO 33
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, R8, Cba, S5 and NHMe modifications. See specification as filed for detailed description of modifications and preferred embodiments.

<400> SEQUENCE: 33

Leu Thr Phe Glu Tyr Trp Ala Thr Ser Ala Ala
1 5 10

<210> SEQ ID NO 34
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, ReN, Cba, Az and NH2 modifications. See specification as filed for detailed description of modifications and preferred embodiments.

<400> SEQUENCE: 34

Leu Thr Phe Ala Tyr Trp Ala Gln Ser Ala Ala
1 5 10

<210> SEQ ID NO 35
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, ReN, Cba, Az and NH2
modifications. See specification as filed for detailed
description of modifications and preferred embodiments.

<400> SEQUENCE: 35

Leu Thr Phe Glu Tyr Trp Ala Gln Ser Ala Ala
1 5 10

<210> SEQ ID NO 36
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, ReN, Cba, Az and NH2
modifications. See specification as filed for detailed
description of modifications and preferred embodiments.

<400> SEQUENCE: 36

Leu Thr Phe Thr Tyr Trp Ala Gln Ser Ala Ala
1 5 10

<210> SEQ ID NO 37
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, ReN, Cba, Az and NHMe
modifications. See specification as filed for detailed
description of modifications and preferred embodiments.

<400> SEQUENCE: 37

Leu Thr Phe Ala Tyr Trp Ala Gln Ser Ala Ala
1 5 10

<210> SEQ ID NO 38
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, ReN, Cba, Az and NHMe
modifications. See specification as filed for detailed
description of modifications and preferred embodiments.

<400> SEQUENCE: 38

Leu Thr Phe Glu Tyr Trp Ala Gln Ser Ala Ala
1 5 10

<210> SEQ ID NO 39
<211> LENGTH: 11
<212> TYPE: PRT

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, ReN, Cba, Az and NHMe
      modifications.  See specification as filed for detailed
      description of modifications and preferred embodiments.

<400> SEQUENCE: 39

Leu Thr Phe Thr Tyr Trp Ala Gln Ser Ala Ala
1               5                   10


<210> SEQ ID NO 40
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, ReN, Cba, Az and NH2
      modifications.  See specification as filed for detailed
      description of modifications and preferred embodiments.

<400> SEQUENCE: 40

Leu Thr Phe Glu Tyr Trp Ala Ala Ser Ala Ala
1               5                   10


<210> SEQ ID NO 41
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, ReN, Cba, Az and NH2
      modifications.  See specification as filed for detailed
      description of modifications and preferred embodiments.

<400> SEQUENCE: 41

Leu Thr Phe Glu Tyr Trp Ala Thr Ser Ala Ala
1               5                   10


<210> SEQ ID NO 42
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, ReN, Cba, Az and NHMe
      modifications.  See specification as filed for detailed
      description of modifications and preferred embodiments.

<400> SEQUENCE: 42

Leu Thr Phe Glu Tyr Trp Ala Ala Ser Ala Ala
1               5                   10


<210> SEQ ID NO 43
<211> LENGTH: 11
<212> TYPE: PRT
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(11)
<223> OTHER INFORMATION: Contains RN, ReN, Cba, Az and NHMe
      modifications.  See specification as filed for detailed
      description of modifications and preferred embodiments.

<400> SEQUENCE: 43

Leu Thr Phe Glu Tyr Trp Ala Gln Ser Ala Ala
1               5                   10


<210> SEQ ID NO 44
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RN, ReN, Cba, Az and NHMe
      modifications.  See specification as filed for detailed
      description of modifications and preferred embodiments.

<400> SEQUENCE: 44

Leu Thr Phe Glu Tyr Trp Ala Thr Ser Ala Ala
1               5                   10


<210> SEQ ID NO 45
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, R8, Cba, S5 and NH2
      modifications.  See specification as filed for detailed
      description of modifications and preferred embodiments.

<400> SEQUENCE: 45

Leu Thr Phe Ala Tyr Trp Ala Gln Ser Ala Ala
1               5                   10


<210> SEQ ID NO 46
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, R8, Cba, S5 and NH2
      modifications.  See specification as filed for detailed
      description of modifications and preferred embodiments.

<400> SEQUENCE: 46

Leu Thr Phe Glu Tyr Trp Ala Gln Ser Ala Ala
1               5                   10


<210> SEQ ID NO 47
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
```

<223> OTHER INFORMATION: Contains RP-L, R8, Cba, S5 and NH2 modifications. See specification as filed for detailed description of modifications and preferred embodiments.

<400> SEQUENCE: 47

Leu Thr Phe Thr Tyr Trp Ala Gln Ser Ala Ala
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, R8, Cba, S5 and NHMe modifications. See specification as filed for detailed description of modifications and preferred embodiments.

<400> SEQUENCE: 48

Leu Thr Phe Ala Tyr Trp Ala Gln Ser Ala Ala
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, R8, Cba, S5 and NHMe modifications. See specification as filed for detailed description of modifications and preferred embodiments.

<400> SEQUENCE: 49

Leu Thr Phe Glu Tyr Trp Ala Gln Ser Ala Ala
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, R8, Cba, S5 and NHMe modifications. See specification as filed for detailed description of modifications and preferred embodiments.

<400> SEQUENCE: 50

Leu Thr Phe Thr Tyr Trp Ala Gln Ser Ala Ala
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, R8, Cba, S5 and NH2 modifications. See specification as filed for detailed description of modifications and preferred embodiments.

<400> SEQUENCE: 51

Leu Thr Phe Glu Tyr Trp Ala Ala Ser Ala Ala
1 5 10

<210> SEQ ID NO 52
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, R8, Cba, S5 and NH2 modifications. See specification as filed for detailed description of modifications and preferred embodiments.

<400> SEQUENCE: 52

Leu Thr Phe Glu Tyr Trp Ala Thr Ser Ala Ala
1 5 10

<210> SEQ ID NO 53
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, R8, Cba, S5 and NHMe modifications. See specification as filed for detailed description of modifications and preferred embodiments.

<400> SEQUENCE: 53

Leu Thr Phe Glu Tyr Trp Ala Ala Ser Ala Ala
1 5 10

<210> SEQ ID NO 54
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, R8, Cba, S5 and NHMe modifications. See specification as filed for detailed description of modifications and preferred embodiments.

<400> SEQUENCE: 54

Leu Thr Phe Glu Tyr Trp Ala Gln Ser Ala Ala
1 5 10

<210> SEQ ID NO 55
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, R8, Cba, S5 and NHMe modifications. See specification as filed for detailed description of modifications and preferred embodiments.

<400> SEQUENCE: 55

-continued

```
Leu Thr Phe Glu Tyr Trp Ala Thr Ser Ala Ala
1               5                   10


<210> SEQ ID NO 56
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, ReN, Cba, Az and NH2
      modifications.  See specification as filed for detailed
      description of modifications and preferred embodiments.

<400> SEQUENCE: 56

Leu Thr Phe Ala Tyr Trp Ala Gln Ser Ala Ala
1               5                   10


<210> SEQ ID NO 57
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, ReN, Cba, Az and NH2
      modifications.  See specification as filed for detailed
      description of modifications and preferred embodiments.

<400> SEQUENCE: 57

Leu Thr Phe Glu Tyr Trp Ala Gln Ser Ala Ala
1               5                   10


<210> SEQ ID NO 58
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, ReN, Cba, Az and NH2
      modifications.  See specification as filed for detailed
      description of modifications and preferred embodiments.

<400> SEQUENCE: 58

Leu Thr Phe Thr Tyr Trp Ala Gln Ser Ala Ala
1               5                   10


<210> SEQ ID NO 59
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, ReN, Cba, Az and NHMe
      modifications.  See specification as filed for detailed
      description of modifications and preferred embodiments.

<400> SEQUENCE: 59

Leu Thr Phe Ala Tyr Trp Ala Gln Ser Ala Ala
1               5                   10
```

```
<210> SEQ ID NO 60
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, ReN, Cba, Az and NHMe
      modifications.  See specification as filed for detailed
      description of modifications and preferred embodiments.

<400> SEQUENCE: 60

Leu Thr Phe Glu Tyr Trp Ala Gln Ser Ala Ala
1               5                   10


<210> SEQ ID NO 61
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, ReN, Cba, Az and NHMe
      modifications.  See specification as filed for detailed
      description of modifications and preferred embodiments.

<400> SEQUENCE: 61

Leu Thr Phe Thr Tyr Trp Ala Gln Ser Ala Ala
1               5                   10


<210> SEQ ID NO 62
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, ReN, Cba, Az and NH2
      modifications.  See specification as filed for detailed
      description of modifications and preferred embodiments.

<400> SEQUENCE: 62

Leu Thr Phe Glu Tyr Trp Ala Ala Ser Ala Ala
1               5                   10


<210> SEQ ID NO 63
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, ReN, Cba, Az and NH2
      modifications.  See specification as filed for detailed
      description of modifications and preferred embodiments.

<400> SEQUENCE: 63

Leu Thr Phe Glu Tyr Trp Ala Thr Ser Ala Ala
1               5                   10


<210> SEQ ID NO 64
<211> LENGTH: 11
```

-continued

<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, ReN, Cba, Az and NHMe modifications. See specification as filed for detailed description of modifications and preferred embodiments.

<400> SEQUENCE: 64

Leu Thr Phe Glu Tyr Trp Ala Ala Ser Ala Ala
1 5 10

<210> SEQ ID NO 65
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, ReN, Cba, Az and NHMe modifications. See specification as filed for detailed description of modifications and preferred embodiments.

<400> SEQUENCE: 65

Leu Thr Phe Glu Tyr Trp Ala Gln Ser Ala Ala
1 5 10

<210> SEQ ID NO 66
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains RP-L, ReN, Cba, Az and NHMe modifications. See specification as filed for detailed description of modifications and preferred embodiments.

<400> SEQUENCE: 66

Leu Thr Phe Glu Tyr Trp Ala Thr Ser Ala Ala
1 5 10

<210> SEQ ID NO 67
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NH2 modifications. See specification as filed for detailed description of modifications and preferred embodiments.

<400> SEQUENCE: 67

Leu Thr Phe Ala Tyr Trp Ala Gln Ser Ala Ala
1 5 10

<210> SEQ ID NO 68
<211> LENGTH: 11
<212> TYPE: PRT
<213> ORGANISM: Artificial Sequence
<220> FEATURE:

<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NH2 modifications. See specification as filed for detailed description of modifications and preferred embodiments.

<400> SEQUENCE: 68

Leu Thr Phe Glu Tyr Trp Ala Gln Ser Ala Ala
1 5 10

<210> SEQ ID NO 69
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NH2 modifications. See specification as filed for detailed description of modifications and preferred embodiments.

<400> SEQUENCE: 69

Leu Thr Phe Thr Tyr Trp Ala Gln Ser Ala Ala
1 5 10

<210> SEQ ID NO 70
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NHMe modifications. See specification as filed for detailed description of modifications and preferred embodiments.

<400> SEQUENCE: 70

Leu Thr Phe Ala Tyr Trp Ala Gln Ser Ala Ala
1 5 10

<210> SEQ ID NO 71
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NHMe modifications. See specification as filed for detailed description of modifications and preferred embodiments.

<400> SEQUENCE: 71

Leu Thr Phe Glu Tyr Trp Ala Gln Ser Ala Ala
1 5 10

<210> SEQ ID NO 72
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTag02, R8, Cba, S5 and NHMe
      modifications.  See specification as filed for detailed
      description of modifications and preferred embodiments.

<400> SEQUENCE: 72

Leu Thr Phe Thr Tyr Trp Ala Gln Ser Ala Ala
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTag02, R8, Cba, S5 and NH2
      modifications.  See specification as filed for detailed
      description of modifications and preferred embodiments.

<400> SEQUENCE: 73

Leu Thr Phe Glu Tyr Trp Ala Ala Ser Ala Ala
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTag02, R8, Cba, S5 and NH2
      modifications.  See specification as filed for detailed
      description of modifications and preferred embodiments.

<400> SEQUENCE: 74

Leu Thr Phe Glu Tyr Trp Ala Thr Ser Ala Ala
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTag02, R8, Cba, S5 and NHMe
      modifications.  See specification as filed for detailed
      description of modifications and preferred embodiments.

<400> SEQUENCE: 75

Leu Thr Phe Glu Tyr Trp Ala Ala Ser Ala Ala
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTag02, R8, Cba, S5 and NHMe
      modifications.  See specification as filed for detailed description of modifications and preferred embodiments.

<400> SEQUENCE: 76

Leu Thr Phe Glu Tyr Trp Ala Gln Ser Ala Ala
1 5 10

<210> SEQ ID NO 77
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, R8, Cba, S5 and NHMe modifications. See specification as filed for detailed description of modifications and preferred embodiments.

<400> SEQUENCE: 77

Leu Thr Phe Glu Tyr Trp Ala Thr Ser Ala Ala
1 5 10

<210> SEQ ID NO 78
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NH2 modifications. See specification as filed for detailed description of modifications and preferred embodiments.

<400> SEQUENCE: 78

Leu Thr Phe Ala Tyr Trp Ala Gln Ser Ala Ala
1 5 10

<210> SEQ ID NO 79
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NH2 modifications. See specification as filed for detailed description of modifications and preferred embodiments.

<400> SEQUENCE: 79

Leu Thr Phe Glu Tyr Trp Ala Gln Ser Ala Ala
1 5 10

<210> SEQ ID NO 80
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NH2 modifications. See specification as filed for detailed description of modifications and preferred embodiments.

<400> SEQUENCE: 80

Leu Thr Phe Thr Tyr Trp Ala Gln Ser Ala Ala
1 5 10

<210> SEQ ID NO 81
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe modifications. See specification as filed for detailed description of modifications and preferred embodiments.

<400> SEQUENCE: 81

Leu Thr Phe Ala Tyr Trp Ala Gln Ser Ala Ala
1 5 10

<210> SEQ ID NO 82
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe modifications. See specification as filed for detailed description of modifications and preferred embodiments.

<400> SEQUENCE: 82

Leu Thr Phe Glu Tyr Trp Ala Gln Ser Ala Ala
1 5 10

<210> SEQ ID NO 83
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe modifications. See specification as filed for detailed description of modifications and preferred embodiments.

<400> SEQUENCE: 83

Leu Thr Phe Thr Tyr Trp Ala Gln Ser Ala Ala
1 5 10

<210> SEQ ID NO 84
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NH2 modifications. See specification as filed for detailed description of modifications and preferred embodiments.

<400> SEQUENCE: 84

Leu Thr Phe Glu Tyr Trp Ala Ala Ser Ala Ala
1 5 10

<210> SEQ ID NO 85
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NH2
modifications. See specification as filed for detailed
description of modifications and preferred embodiments.

<400> SEQUENCE: 85

Leu Thr Phe Glu Tyr Trp Ala Thr Ser Ala Ala
1 5 10

<210> SEQ ID NO 86
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe
modifications. See specification as filed for detailed
description of modifications and preferred embodiments.

<400> SEQUENCE: 86

Leu Thr Phe Glu Tyr Trp Ala Ala Ser Ala Ala
1 5 10

<210> SEQ ID NO 87
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe
modifications. See specification as filed for detailed
description of modifications and preferred embodiments.

<400> SEQUENCE: 87

Leu Thr Phe Glu Tyr Trp Ala Gln Ser Ala Ala
1 5 10

<210> SEQ ID NO 88
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Contains HaloTagO2, ReN, Cba, Az and NHMe
modifications. See specification as filed for detailed
description of modifications and preferred embodiments.

<400> SEQUENCE: 88

Leu Thr Phe Glu Tyr Trp Ala Thr Ser Ala Ala
1 5 10

TECHNOLOGIES USEFUL FOR ASSESSING PERMEABILITY

CROSS-REFERENCE TO RELATED APPLICATIONS

This application is a National Stage Entry of International Application No. PCT/US2020/064685, filed Dec. 11, 2020, which claims priority to U.S. Provisional Application No. 62/946,736, filed Dec. 11, 2019, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Apr. 28, 2026, is named Sequence_Listing.txt and is 37,817 bytes in size.

BACKGROUND

The invention relates to the field of biology and chemistry, particularly cellular biology and biochemistry.

Over the past three decades, there has been increased understanding of intracellular mechanisms and how these mechanisms signal cells to act. For instance, intracellular signaling can rapidly transmit signals from the cell surface to the nucleus, and vice versa, resulting in cellular activities including cell proliferation, apoptosis, differentiation, and changes in gene expression. Because of this increased understanding, there has been an identification of intracellular molecules (e.g., proteins) that can be stimulated and/or inhibited to change the way the cell will act. Sometimes, the stimulation of an intracellular target can be the result of a mutation or other damage to that target. For example, mutations and overexpression of intracellular molecule β-catenin is associated with many cancers.

Although the importance of intracellular molecules in the signaling within a cell has been known from decades, it has been a challenge to identify agents that can specifically target a particular intracellular molecule to affect that molecule's behavior, and thus affect the cell's activity. One of the challenges to identifying such an agent has been that it is difficult to predict whether an agent that specifically binds to a particular target (e.g., the Ras protein) will be able to traverse the membrane of a cell in order to access the intracellular space where their target resides.

The cell membrane of a non-plant eukaryotic cell is sometimes called a plasma membrane. The cell membrane is a double layer of lipids that separates the interior of a cell from the extracellular environment (e.g., the interstitial space and the fluids that reside therein). The lipids in the cell membrane are typically phospholipids. A phospholipid has a hydrophilic (water-loving) phosphate head along with a hydrophobic (water-repelling) fatty acid tail. In the double layer, phospholipid molecules are arranged such that the hydrophobic tails point inward, and the hydrophilic heads face outward. This double layer of phospholipids is called a phospholipid bilayer (see FIG. 1). The cell membrane in FIG. 1 would encircle the cytoplasm of a cell on the intracellular side of the depicted membrane, with the extracellular side of the membrane labeled accordingly. A cell membrane is comprised of a phospholipid bilayer along with molecules, such as proteins, that pass through all or some of the double layer membrane. For example, some molecules, such as ion channels, span the entire membrane, which one part exposed to the interior of the cell and the other part exposed to the extracellular surface. Other molecules may be attached to and partially contained within the interior layer of the plasma membrane, but do not pass through the membrane and thus do not protrude into the extracellular space.

Given its complexity, it is difficult to know if a molecule will be able to traverse the cell membrane in order to get to an intracellular target that the molecule will specifically bind to.

Thus, there is a need to discover a method for identifying intracellular target-specific agents that are able to traverse a cell membrane to access the intracellular target.

SUMMARY

Among other things, the present disclosure provides technologies for assessing barrier-crossing (e.g., cell membrane crossing) by an agent. In some embodiments, the present disclosure provides technologies for assessing interactions of a first agent (e.g., a capture molecule as described herein) with a second agent (e.g., a candidate compound linked to a binding moiety as described herein). In some embodiments, a first agent, e.g. a capture molecule, is limited in a region (e.g., a first region as described herein) by a barrier (a membrane, a layer, etc. as described herein). In some embodiments, a first agent is within a cell. In some embodiments, a first agent is within a liposome. In various embodiments, a first agent does not cross a barrier, or at very low level, to come in contact with a first agent. In some embodiments, after crossing a barrier, an agent such as a second agent forms a complex with a first agent, in some embodiments, by covalent linking. Such complexes can be utilized, as in many traditional technologies, for assessing barrier-crossing of a second agent and/or interactions between a first and a second agents. In some embodiments, after crossing a barrier, an agent, e.g., a second agent, is converted into a corresponding product agent (e.g., a product agent of a second agent) which possesses different properties and/or structures that can be utilized for detection. Among other things, the present disclosure demonstrates that utilization of such product agents of second agents can greatly improved sensitivity, accuracy and/or efficiency of detection and/or assessment. In some embodiments, multiple agents (e.g., 2, 3, 4, 5, 10, 20, 30, 40, 50, 60, 70, 80, 100, 150, 200 or more) can be assessed at the same time with high-throughput, in some embodiments administered at the same time optionally in a single composition, e.g., when combined with mass spectrometry described herein.

In some embodiments, a first agent is or comprises a capture molecule as described herein. In some embodiments, a first agent is a capture molecule as described herein. In some embodiments, a first agent, e.g., a capture molecule, is or comprises a macromolecule agent, e.g. a protein. In some embodiments, a first agent is or comprises a polypeptide moiety. In some embodiments, a polypeptide is an enzyme. In some embodiments, a polypeptide is a target of a binding moiety, e.g., a binding moiety of a second agent. In some embodiments, a first agent is or comprises a functional group optionally linked to the rest of the first agent through a linker. In some embodiments, a functional group is an amino acid residue, e.g., of a polypeptide (e.g., an acid amino residue such as Asp, Glu, etc.). In some embodiments, a first agent comprises a functional group and a linker. In some embodiments, a linker in a first agent is or comprises a chemically cleavable linker (CCL). Various first agents and compositions thereof are described herein. In some embodiments, a provided agent is a first agent.

In some embodiments, a second agent is or comprises a candidate compound as described herein. In some embodiments, a second agent is a candidate compound linked to a binding moiety as described herein. In some embodiments, a second agent comprises a binding moiety which can interact with a first agent. In some embodiments, a binding moiety binds to a first agent upon contact. In some embodiments, a binding moiety can form a covalent linkage with a first agent upon contact. In some embodiments, a binding moiety is or comprises a functional group and optionally a linker. In some embodiments, a binding moiety is or comprises a functional group and a linker. In some embodiments, a binding moiety is or comprises a functional group and optionally a linker. In some embodiments, a binding moiety is or comprises a functional group and a linker. In some embodiments, a linker, e.g., in a second agent, is or comprises a chemically cleavable linker (CCL). In some embodiments, a functional group in a second agent binds to a functional group in a first agent. In some embodiments, functional groups in a first and a second agents react with each other so that a first and a second agents are covalently linked. In some embodiments, a reaction between functional groups in a first and a second agent is a bioorthogonal reaction. Those skilled in the art reading the present disclosure will appreciate that various bioorthogonal reactions and/or functional groups can be utilized in accordance with the present disclosure. In some embodiments, a second agent consists of or comprises a scaffold agent moiety and a binding moiety. In some embodiments, a second agent consists of or comprises a scaffold agent moiety, a functional group and optionally a linker. In some embodiments, a second agent consists of or comprises a scaffold agent moiety, a second functional group and a linker. In some embodiments, a scaffold agent is or comprises a small molecule. In some embodiments, a scaffold agent is or comprises a polypeptide. In some embodiments, a scaffold agent is or comprises a stapled peptide. In some embodiments, a scaffold agent is or comprises a nucleic acid. In some embodiments, a scaffold agent is or comprises an oligonucleotide. In some embodiments, a second agent is prepared from a scaffold agent. In many embodiments, a second agent is not prepared from a scaffold agent. For example, in some embodiments, a scaffold agent is or comprises a peptide moiety, and its corresponding second agent is prepared by replacing at least one amino acid residues in a scaffold agent with an amino acid residue which comprises or can be connected to a functional group optionally through a linker during peptide synthesis. Various second agents and compositions thereof are described herein. In some embodiments, a provided agent is a second agent.

Linkers in various agents may independently be or comprise CCLs. In some embodiments, a CCL, e.g., which is or comprises —C(O)O—, is cleaved in a chemical condition, e.g., an alkaline condition. In some embodiments, cleavage includes catalytic cleavage (e.g., promoted by a metal catalyst), acidic cleavage (e.g., as shown in FIG. 8C by TFA or FIG. 8D by 10% formic acid), oxidation cleavage, reduction cleavage, light-promoted cleavage (e.g., cleavage provided by UV light), etc. In some embodiments, cleavage of a CCL in a first and/or a second agent is promoted by an enzyme. In some embodiments, a CCL is or comprises a moiety that is cleavable by an enzyme. In some embodiments, an enzyme is or comprise a protease. In some embodiments, an enzyme is or comprise a peptidase. In some embodiments, an enzyme is or comprise a hydrolase. In some embodiments, a CCL is or comprises an ester group that is cleavable by an esterase. In some embodiments, a CCL is or comprises a polypeptide moiety that is recognizable and cleavable by an enzyme. In some embodiments, a first agent comprises a CCL and a second agent does not. In some embodiments, a second agent comprises a CCL and a first agent does not. In some embodiments, both a first and a second agents independently comprise a CCL. In some embodiments, none of a first and a second agents comprises a CCL. In some embodiments, a CCL is or comprises —C(O)—O—. In some embodiments, a CCL is or comprises vicinal diols. In some embodiments, a CCL is or comprises —N=N—. In some embodiments, a CCL is or comprises —Ar—N=N—Ar—, wherein each Ar is independently an aromatic moiety. In some embodiments, a CCL is or comprises a CCL moiety as described in FIGS. 8A-8E. In some embodiments, a CCL is formed by a reaction of a first and second agent. For example, in some embodiments, a CCL is or comprises —C(O)—O— which is formed by a —COOH functional group (or a salt or activated form thereof) of a first agent with a functional group, e.g., a leaving group such as —Cl, of a second agent.

In some embodiments, a linker is a covalent bond.

In some embodiments, agents of the present disclosure form complexes when in contact. For example, in various embodiments, a first agent and a second agent can form a complex. In some embodiments, a first agent and a second agent are covalently linked. In some embodiments, a first agent and a second agent are not covalent linked but form a complex through non-covalent interaction. In some embodiments, a non-covalent interaction comprises an interaction of biotin with a biotin-binding entity, e.g., avidin, streptavidin, etc. In some embodiments, provided technologies comprises enrichment of such complexes. In some embodiments, enrichment of such complexes may improve detection of certain agents, e.g., agents comprising releasing moieties as described herein. In some embodiments, a complex comprises a CCL. In some embodiments, a complex comprises two CCLs. In some embodiments, a complex comprises a CCL in a first agent moiety. In some embodiments, a complex comprises a CCL in a second agent moiety. In some embodiments, a complex independently comprises a CCL in a first agent moiety and a second agent moiety.

As described herein, in various embodiments, an agent, e.g., a first agent, a second agent, etc., is transformed, e.g., after crossing a barrier (e.g., a layer such as cell membrane). In some embodiments, a first agent is transformed into a product agent. In some embodiments, a second agent is transformed into a product agent. In some embodiments, a product agent is a product agent of a first agent. In some embodiments, a product agent is a product agent of a second agent. In some embodiments, a product agent is formed by transforming one or more groups in a first and/or second agent.

In some embodiments, a product agent of a first agent is or comprises a moiety of a second moiety, e.g., comprising a reaction product moiety of functional groups of a first and a second moiety. In some embodiments, a product agent of a first agent has a different molecular mass from a first agent. In some embodiments, a product agent of a first agent has a different molecular mass from a first agent. In some embodiments, such difference is detected by mass spectrometry.

In some embodiments, a product agent of a second agent is or comprises a moiety of a first moiety, e.g., comprising a reaction product moiety of functional groups of a first and a second moiety. In some embodiments, a product agent of a second agent has a different molecular mass from a second agent. In some embodiments, a product agent of a second agent has a different molecular mass from a second agent. In some embodiments, such difference is detected by mass spectrometry. For example, in various embodiments, —Cl of a second agent is converted into —OH in a product agent.

In some embodiments, a product agent comprises a releasing moiety. In some embodiments, a product agent is formed by cleavage of a CCL in a complex as described herein. In some embodiments, a product agent is or comprises a first and/or second agent moiety after cleavage.

In some embodiments, a product agent, e.g., a product agent of a second agent, consists of or comprises a scaffold agent moiety as described herein, a releasing moiety, and optionally a linker. In some embodiments, a scaffold agent of a product agent shares a characteristic structural element (e.g., a scaffold, a peptide sequence, a staple, or one or more characteristic portions thereof, etc.) as that of a second agent. In some embodiments, a scaffold agent of a product agent shares a common scaffold as that of a second agent. In some embodiments, a scaffold agent of a product agent is the same as that of a second agent. In some embodiments, a releasing moiety differs from a function group. For example, in some embodiments, a releasing moiety of a product of second agent is different from a functional group of a second agent. In some embodiments, a releasing moiety is —OH. In some embodiments, a functional group of a second agent is —Cl. In some embodiments, a releasing moiety is or comprises a moiety of a first agent. In some embodiments, a releasing moiety is or comprises a moiety of a reaction product of a first and a second agents (e.g., a moiety of a product moiety of functional groups in a first and second moiety).

In some embodiments, a product agent of a second agent and a second agent shares the same scaffold agent moiety or a characteristic structural element, and optionally the same linker. In some embodiments, a scaffold agent is or comprises a peptide. In some embodiments, a scaffold agent is or comprises a stapled peptide.

Various staple peptides may be utilized in accordance with the present disclosure, e.g., stapled peptides described in U.S. Pat. No. 8,957,026, WO 2005/044839, WO 2008/061192, WO 2008/095063, WO 2008/121767, WO 2010/011313, WO 2011/008260, WO 2012/174423, WO 2012/174409, WO 2014/197821, WO 2008/137633, WO 2009/042237, WO 2009/108261, WO 2010/042225, WO 2010/068684, WO 2010/148335, WO 2011/094708, WO 2012/006598, WO 2012/065181, WO 2012/142604, WO 2013/055949, WO 2013/102211, WO 2013/142281, WO 2014/144768, WO 2014/144148, WO 2014/151369, WO 2016/149613, WO 2017/004591, WO 2017/040323, WO 2017/040329, U.S. Pat. Nos. 8,592,377, 9,556,227, 10,301,351, 9,163,330, US 2018/010001, U.S. Pat. No. 9,617,309, US 2018/0009847, US 2015/0225471, U.S. Pat. No. 10,081,654, US 2019/0202862, WO 2014/201370, WO 2015/051030, U.S. Pat. No. 10,533,039, US 2020/0247858, and WO 2020/041270, the stapled peptides and staples of each of which is independently incorporated herein by reference. In some embodiments, a stapled peptide comprises one and only one staples. In some embodiments, a stapled peptides comprises two or more staples. In some embodiments, a staple is a hydrocarbon staple. In some embodiments, a staple comprises a carbamate group. In some embodiments, a staple comprises an amine group. In some embodiments, a staple is bonded to a residue whose backbone comprises a cyclic structure, e.g., a proline residue. In some embodiments, a staple is bonded to an alpha-carbon of an amino acid residue. In some embodiments, a stapled peptide is a stitched peptide.

In some embodiments, a product agent of a second agent and a second agent comprises the same scaffold agent moiety, wherein the scaffold agent is a stapled peptide.

In some embodiments, a provided agent is or comprises a first agent. In some embodiments, a provided agent is or comprises a second agent. In some embodiments, a provided agent is or comprises a complex agent, e.g., of a first and a second agent. In some embodiments, provided agent is or comprises a product agent. In some embodiments, provided agent is or comprises a product agent of a first agent. In some embodiments, provided agent is or comprises a product agent of a second agent.

In some embodiments, linkers, functional groups, releasing moieties, etc., may be attached to scaffold agent moieties at various locations. For example, in some embodiments, a scaffold agent is or comprises a peptide, and they may be connected at N-terminus, C-terminus, side chain(s), and/or staple(s) (if stapled peptide).

As appreciated by those skilled in the art, provided technologies, e.g., agents, compounds, etc., may be provided in various forms including various salt forms, such as various pharmaceutically acceptable salt forms. In some embodiments, agents or compounds are provided as pharmaceutically acceptable salts.

In some embodiments, the present disclosure provides a method comprising detecting a product agent of an agent. In some embodiments, formation of a product agent comprises an agent crossing a barrier, e.g., crossing a barrier into a region where a product agent or a precursor thereof is formed. In some embodiments, the present disclosure provides a method, comprising detecting a product agent of an agent, or a precursor thereof, in a region, when an agent enters a region by crossing a barrier and forms a product agent of an agent, or a precursor thereof, in a region. In some embodiments, an agent is a second agent as described herein. In some embodiments, a barrier is or comprises a layer. In some embodiments, a barrier is or comprises a lipid layer. In some embodiments, a barrier is or comprises a bilayer. In some embodiments, a barrier is or comprises a phospholipid bilayer. In some embodiments, a barrier is or comprise a membrane. In some embodiments, a barrier is or comprise a cell membrane. In some embodiments, a region is within a cell. In some embodiments, an agent is a second agent, and a product agent is a product agent of a second agent. In some embodiments, a product agent of a second agent or a precursor thereof is formed at a first region, wherein a first region and a second region are separated by a barrier. In some embodiments, a first region comprises a first agent, e.g., a capture molecule, as described herein. In some embodiments, a first agent is absent from a second region. In some embodiments, a first and a second agent bind to each other in a first region to form a complex. In some embodiments, a first and a second agent react with each other in a first region to form a complex. In some embodiments, a first and a second agent are covalently linked in a first region to form a complex. In some embodiments, a precursor of a product agent, e.g., of a product agent of a first and/or a second agent is a complex. In some embodiments, cleavage of a complex forms a product agent of a second agent. In some embodiments, cleavage of a CCL forms a product agent of a second agent.

In some embodiments, complexes are enriched, e.g., through affinity purification as described herein. In some embodiments, enrichment improves detection of a product agent of a second agent. In some embodiments, production of a product agent is after enrichment of a complex. In some embodiments, product of a product agent is through chemical and/or enzymatic digestion of a complex to yield a product agent of a first and/or a second agent. In some embodiments, product of a product agent is through chemical (e.g., basic conditions as described herein) and/or enzymatic cleavage of a CCL to yield a product agent of a first and/or a second agent. For example, in some embodiments, enzymes such as esterases are utilized to cleave —CO(O)—. In some embodiments, useful enzymes are or comprises proteases, peptidases and/or hydrolases. In various embodiments, conditions utilized are effective in cleaving CCL and are mild enough to not significantly damage one or more other moieties, e.g., scaffold agent moiety, candidate compound moiety, etc. or characteristic portions thereof. In some embodiments, conditions are mild enough not to significantly damage stapled peptide moieties or characteristic portions thereof.

In some embodiments, a complex is detected and its levels assessed. In some embodiments, product agents, e.g., of first agents and/or second agents, are detected and their levels assessed. Particularly, in many embodiments, product agents of send agents are detected and their levels assessed. In some embodiments, barrier-crossing of agents is assessed by presence and/or levels of product agents (e.g., compared to those of reference agents). In some embodiments, an agent is determined to cross a barrier by the presence and/or above a certain level of its product agent. In some embodiments, a reference agent does not cross a barrier or cross at very low levels (a negative reference agent). In some embodiments, a reference agent cross a barrier at a high level (a positive reference agent). In some embodiments, relative permeability factor of an agent, which is calculated as (level/amount of product agent of an agent−level/amount of product agent of a negative reference agent)/(level/amount of product agent of a positive reference agent−level/amount of product agent of a negative reference agent), is utilized to assess permeability across a barrier, e.g., a membrane such as a call membrane. In some embodiments, product agent ratio, which is calculated as (level/amount of product agent of an agent)/(level/amount of product agent of a positive reference agent) is utilized to assess permeability across a barrier, e.g., a membrane such as a call membrane. In some embodiments, reference agents and agents to be assessed are administered separately, e.g., as exemplified herein, in some embodiments, they were administered in separate wells wherein references agents were not administered in the same wells. In some embodiments, reference agents and agents to be assessed are administered simultaneously, in some embodiments, optionally in the same composition. In some embodiments, reference agents and agents to be assessed contact the same barrier. In some embodiments, reference agents and agents, as exemplified herein, are administered in the same wells. In some embodiments, a system comprises an agent and a reference agent (positive or negative), and a barrier (e.g., cell membrane of a cell). In some embodiments, a system comprises an agent, a positive reference agent and a negative reference agent, and a barrier. In some embodiments, a system comprises an agent and a reference agent (positive or negative) and a plurality of cells. In some embodiments, a system comprises an agent, a positive and a negative reference agent, and a plurality of cells. In some embodiments, a positive reference agent crosses membrane of a plurality of cells. In some embodiments, cells comprise first agents that agents to be tested, as second agents, can bind to or react with as described herein. For example, in some embodiments, cells comprise capture molecules as described herein. In some embodiments, a system is or comprises a composition comprising components therein in a well of a plate as described herein.

As described herein, one advantage of certain provided technologies is that multiplexing assessment can be performed. In some embodiments, a plurality of agents, e.g., 2, 3, 4, 5, 6, 7, 8, 9, 10, 11, 12, 13, 14, 15, 16, 17, 18, 19, 20, 30, 40, 50, 60, 70, 80, 90, 100, 150, 200, 250, 300, 400, 500 or more compounds are assessed simultaneously in a composition (in some embodiments, administered as a single composition; in some embodiments, added as one or more separate compositions). In some embodiments, a plurality of agents are or comprises members of a library. In some embodiments, a library of agents may be assessed at the same time; in some embodiments, directly from synthesis without purification. As exemplified herein, in some embodiments, a plurality of agents can be assessed together in a well. As described herein, typically a positive and/or a negative reference agent is also administered. In some embodiments, agents of a plurality share the same binding moieties; in some embodiments, binding moieties of one or more agents in the plurality are different from one or more other agents. In some embodiments, agents of a plurality share the same functional groups; in some embodiments, functional groups of one or more agents in the plurality are different from one or more other agents. In some embodiments, agents of a plurality share the same linker; in some embodiments, linkers of one or more agents in the plurality are different from one or more other agents. In some embodiments, agents of a plurality bind to or react with the same type of agents (e.g., capture molecules as described herein); in some embodiments, they bind to or react with different types of agents (e.g., capture molecules as described herein). In some embodiments, reactions are the same; in some embodiments, reactions are different, for agents of the plurality. In some embodiments, product agents of agents of a plurality (e.g., from digestion/cleavage of complexes formed by agents of a plurality with other agents, e.g., capture molecules, or otherwise converted from agents of a plurality) share the same releasing moieties; in some embodiments, releasing moieties of one or more product agents of agents in the plurality are different from one or more other agents. In some embodiments, product agents of agents of a plurality share the same linkers; in some embodiments, linkers of one or more product agents of agents in the plurality are different from one or more other agents. In some embodiments, for each agent in a plurality, its molecular mass is different from a product agent of the agent. In some embodiments, each agent independently has a different molecular mass. In some embodiments, a product agent of each agent of a plurality independently has a different molecular mass. In some embodiments, differences in molecular mass may be utilized for assessing barrier crossing, e.g., through assessment of levels of product agents utilizing mass spectrometry.

In some embodiments, an agent, e.g., a first agent such as a capture molecule as described herein, comprises a tag. In some embodiments, complexes formed by such agent with another agent, e.g., a second agent such as a candidate compound linked to a binding moiety as described herein, comprises a tag. In some embodiments, a tag is or comprises a His tag (e.g., a hexahistidine tag), a GST tag, a FLAG tag, etc. Among other things, tags may be utilized to enrich complexes and/or agents, which can be utilized for production of product agents. As appreciated by those skilled in the art, enrichment of agents and/or complexes comprising tags can be performed using various technologies as described herein. For example, in some embodiments, an agent, e.g., a capture molecule such as a capture protein with a bound agent (e.g., a complex formed), can be enriched/purified from treated cells by lysing the cells, and then isolating a capture molecule complex through the use of an affinity tag, such as such as a hexahistidine tag, or a GST tag, or FLAG tag, etc, that is fused to a capture protein. As described herein, such a step can allow separation of a capture molecule complex from other contents of a cell and any non-captured agent, and can among other things, improve signal of an assay and/or reduce false positives from uncaptured agents or other cellular contents. A product agent can then be released from a purified capture molecule complex using various methods as described herein.

In some embodiments, the present disclosure provides a method for identifying one or more candidate compounds that traverse an cell monolayer, the method comprising:

- providing cell monolayer comprising a first side and a second side, the first side defining a first region, said first region comprising one or more capture molecules;
- adding a plurality of distinct candidate compounds, each distinct candidate compound attached to a binding moiety, to a second region defined by the second side of the cell monolayer, under conditions whereby each distinct candidate compound of the plurality traversing the cell monolayer enters the first region and forms a complex with a capture molecule in the first region via a covalent bond between a portion of the binding moiety attached to the distinct candidate compound and the capture molecule, wherein one or more complexes are formed;
- disrupting the one or more complexes to create one or more distinct candidate compounds each attached to a releasing moiety, said releasing moiety different from the binding moiety; and/or
- identifying the one or more distinct candidate compounds attached to the releasing moiety as being one or more candidate compounds that traverses an animal cell monolayer.

In some embodiments, the present disclosure provides a method for determining if a candidate compound traverses an animal cell monolayer, the method comprising:

- providing a cell monolayer comprising a first side and a second side, the first side defining a first region, said first region comprising one or more capture molecules;
- adding the candidate compound attached to a binding moiety to a second region defined by the second side of the cell monolayer, under conditions whereby the candidate compound traversing the cell monolayer enters the first region and forms a complex with a capture molecule in the first region via a covalent bond between a portion of the binding moiety attached to the candidate compound and the capture molecule;
- disrupting the complex to create the candidate compound attached to a releasing moiety, said releasing moiety different from the binding moiety; and/or
- identifying the candidate compound attached to the releasing moiety as being a compound that traverses an animal cell monolayer.

In an aspect, the invention provides a method for identifying one or more candidate compounds that traverse an animal cell membrane, the method comprising providing phospholipid bilayer comprising a first side and a second side, the first side defining a first region, said first region comprising one or more capture molecules; adding a plurality of distinct candidate compounds, each distinct candidate compound attached to a binding moiety, to a second region defined by the second side of the phospholipid bilayer, under conditions whereby each distinct candidate compound attached to the binding moiety traversing the phospholipid bilayer enters the first region and forms a complex with a capture molecule in the first region via a covalent bond between a portion of the binding moiety attached to the distinct candidate compound and the capture molecule, wherein one or more complexes are formed; disrupting the one or more complexes to create one or more distinct candidate compounds each attached to a releasing moiety, said releasing moiety different from the binding moiety; and identifying the one or more distinct candidate compounds attached to the releasing moiety as being one or more candidate compounds that traverses an animal cell membrane. In some embodiments, the identifying step identifies the amino acid sequence of the candidate compound. In some embodiments, the identifying step identifies the structure of the candidate compound.

In another aspect, the invention provides a method for determining if a candidate compound traverses an animal cell membrane, the method comprising: providing phospholipid bilayer comprising a first side and a second side, the first side defining a first region, said first region comprising one or more capture molecules; adding the candidate compound attached to a binding moiety to a second region defined by the second side of the phospholipid bilayer, under conditions whereby the candidate compound attached to the binding moiety traversing the phospholipid bilayer enters the first region and forms a complex with a capture molecule in the first region via a covalent bond between a portion of the binding moiety attached to the candidate compound and the capture molecule; disrupting the complex to create the candidate compound attached to a releasing moiety, said releasing moiety different from the binding moiety; and identifying the candidate compound attached to the releasing moiety as being a compound that traverses an animal cell membrane. In some embodiments, the identifying step identifies the amino acid sequence of the candidate compound. In some embodiments, the identifying step identifies the structure of the candidate compound.

In some embodiments of the various aspects of the invention, the phospholipid bilayer is contiguous. In some embodiments of the various aspects of the invention, the phospholipid bilayer is a cell membrane of an animal cell. In some embodiments, the first region is an interior of a liposome. In some embodiments, first region is a cytosol of the animal cell. The animal cell may be the cell of a vertebrate animal. In some embodiments, the vertebrate animal is a mammal. In some embodiments, the mammal is a human. In some embodiments, the mammal is a mouse, rat, hamster, monkey, rabbit, or dog. In some embodiments, animal cell is the cell of an insect. In some embodiments, animal cell is the cell of a bird. In some embodiments, animal cell is the cell of a fish. In some embodiments, the animal cell has a nucleus.

In some embodiments, the phospholipid bilayer is planar.

In some embodiments of the various aspects of the invention, the method further comprises the step of disrupting the phospholipid bilayer so that the first region and the second region are combined to create a mixed region after complex formation in the first region.

In some embodiments, the binding moiety is larger in mass than the releasing moiety. In some embodiments, the binding moiety is smaller in mass than the releasing moiety.

In some embodiments, the releasing moiety is created by replacing at least one atom of the binding moiety with at least one different atom.

In some embodiments, the complex is disrupted by exposing the complex to an environment with a pH of 11.0 or higher. For example, the pH may be 11.5 or higher, or the pH may be 12.0 or higher.

In some embodiments, disrupting the one or more complexes is or comprises breakup of an intermediate and/or release of a product by a capture molecule. In some embodiments, such a process is automatically performed by enzymes.

In some embodiments, the identification of the candidate compound attached to the releasing moiety is by mass spectrometry analysis.

In various embodiments, the candidate compound comprises a peptide. In some embodiments, the peptide comprises, consists essentially of, or consists of an alpha helical turn. In some embodiments, the peptide further comprises a small molecule scaffold stabilizing an alpha helical turn in the peptide. In some embodiment, the peptide is synthetic.

In some embodiments, the capture molecule comprises a linker comprising a chemically cleavable linker and a functional group, said functional group able to covalently bind to at least a portion of a binding moiety attached to a candidate compound.

In some embodiments, capture molecule comprises, consists essentially of, or consists of a mutant form of a haloalkane dehalogenase, said mutant form lacking a hydrolase activity. In some embodiments, the capture molecule forms a covalent bond with a group selected from the group consisting of a benzylguanine derivative and a O-benzylcystosine derivative. In some embodiments, the capture molecule comprises, consists essentially of, or consists of a mutant form of an $O^6$-alkylguanine-DNA alkyltransferase.

In some embodiments, the method includes providing phospholipid bilayer comprising a first side and a second side, the first side defining a first region, said first region comprising one or more capture molecules; adding a plurality of distinct candidate compounds, each distinct candidate compound attached to a binding moiety, to a second region defined by the second side of the phospholipid bilayer, under conditions whereby each distinct candidate compound of the plurality traversing the phospholipid bilayer enters the first region and forms a complex with a capture molecule in the first region via a covalent bond between a portion of the binding moiety attached to the distinct candidate compound and the capture molecule, wherein one or more complexes are formed; disrupting the one or more complexes to create one or more distinct candidate compounds each attached to a releasing moiety, said releasing moiety different from the binding moiety; and identifying the one or more distinct candidate compounds attached to the releasing moiety as being one or more candidate compounds that traverses an animal cell membrane.

In some embodiments, the invention provides methods and reagents for identifying target-specific agents that are able to traverse the cell membrane.

Additional aspects and embodiments of the invention are described herein.

BRIEF DESCRIPTION OF THE DRAWINGS

As shown in FIG. 3A, a phospholipid bilayer separates a first region from a second region, where the first region contains a capture molecule and the second region contains a candidate compound attached to a binding moiety. In FIG. 3B, if the candidate compound is able to traverse the phospholipid bilayer, the binding moiety will covalently bind to the capture molecule. In FIG. 3C, this complex of capture molecule:binding moiety:candidate compound is disrupted, creating a candidate compound attached to a releasing moiety.

As shown in FIG. 4A, Candidate Compound A does not traverse the phospholipid bilayer while Candidate Compound B and Candidate Compound C do traverse the phospholipid bilayer, and the binding moieties attached to Candidate Compound B and Candidate Compound C bind to capture molecules to form complexes in the first region. In FIG. 4B, disruption of the complexes results in Candidate Compound B attached to the releasing moiety and Candidate Compound C attached to the releasing moiety.

FIG. 5B is a magnification of the indicated section in FIG. 5A showing the phospholipid bilayer.

As shown in FIG. 6, the capture molecule is within the first region and the candidate compound attached to a binding moiety is in the second region.

In FIG. 7A, the candidate compound (R) attached to a binding moiety reacts with a capture molecule, where the capture molecule is a HaloTag protein, forming a complex comprising the HaloTag protein, a portion of the binding moiety, and the candidate compound. As shown by the circled atoms in FIGS. 7A-7B, the Cl atom in the binding moiety is replaced by an ester link in the complex, which is then replaced by a hydroxyl group (—OH) on the releasing moiety following disrupted by base hydrolysis.

As shown in FIG. 10A, the capture molecule is created in the first region by the covalent attachment of the SNAP-tag protein to the small linker that enters the first region by traversing the phospholipid bilayer. A candidate compound attached to a binding moiety (that includes a second functional group (FG2)) traversing the phospholipid bilayer will enter the first region and covalently bind to the capture molecule via the FG2 group bonding to the FG1 group to form a complex, which is then chemically cleaved to create a candidate compound attached to a releasing moiety (see bottom of FIG. 10B).

DETAILED DESCRIPTION OF THE PREFERRED EMBODIMENTS

Figure 1:
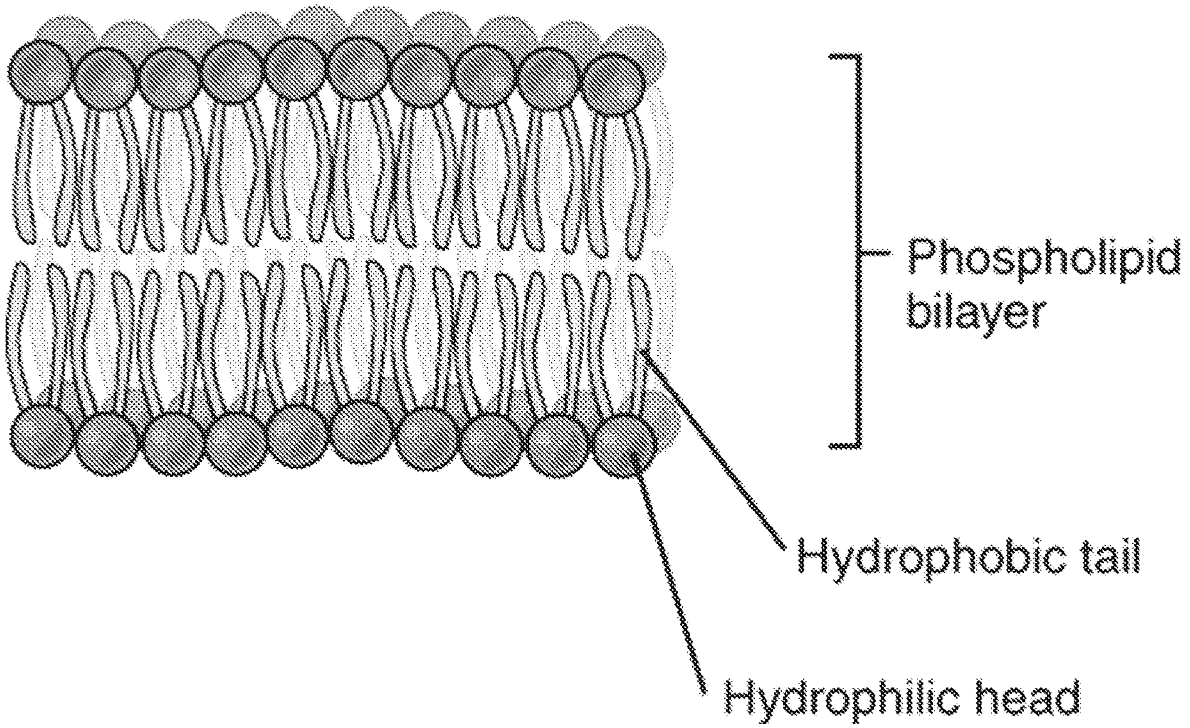
FIG. 1 is a drawing showing a phospholipid bilayer, showing how individual phospholipid molecules orient themselves such that their hydrophilic tails face one another and their hydrophilic heads face away from each other.

Among other things, the present disclosure provides various technologies, e.g., agents, methods, complexes, etc. as described herein. In some embodiments, provided technologies are useful for assessing barrier-crossing by an agent. In some embodiments, provided technologies are useful for assessing permeability of an agent across a barrier, e.g., a cell membrane. In some embodiments, provided technologies are useful for assessing membrane penetration of an agent. In some embodiments, the provided technologies are useful for identifying agents, e.g., candidate compounds, that can cross a barrier, e.g., a cell membrane.

In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents, and/or agents of certain properties (e.g., cell permeability) within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

As used herein, "polypeptide" refers to any polymeric chain of residues (e.g., amino acids) that are typically linked by peptide bonds. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

The term "peptide" as used herein generally refers to a polypeptide that is typically relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids. In some embodiments, a peptide, e.g., a stapled peptide, has a length of 5, 6, 7, 8, 9, 10, 11, 12, 13, 14, 15, 16, 17, 18, 19, 20 or more amino acids.

In some embodiments, a length of a peptide, a polypeptide, or a characteristic portion thereof, is 5 or more amino acids. In some embodiments, a length is 6 or more amino acids. In some embodiments, a length is 7 or more amino acids. In some embodiments, a length is 8 or more amino acids. In some embodiments, a length is 9 or more amino acids. In some embodiments, a length is 10 or more amino acids. In some embodiments, a length is 11 or more amino acids. In some embodiments, a length is 12 or more amino acids. In some embodiments, a length is 13 or more amino acids. In some embodiments, a length is 14 or more amino acids. In some embodiments, a length is 15 or more amino acids. In some embodiments, a length is 16 or more amino acids. In some embodiments, a length is 17 or more amino acids. In some embodiments, a length is 18 or more amino acids. In some embodiments, a length is 19 or more amino acids. In some embodiments, a length is 20 or more amino acids. In some embodiments, a peptide or a characteristic portion thereof is stapled.

As used herein, the term "characteristic portion", in the broadest sense, refers to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity. In certain embodiments, a characteristic portion shares at least one functional characteristic with the intact substance. For example, in some embodiments, a "characteristic portion" of a protein or polypeptide or peptide is one that contains a continuous stretch of amino acids, or a collection of continuous stretches of amino acids, that together are characteristic of a protein or polypeptide or a peptide. In some embodiments, each such continuous stretch generally contains at least 2, 5, 10, 15, 20, 50, or more amino acids. In general, a characteristic portion of a substance (e.g., of a protein, polypeptide, peptide etc.) is one that, in addition to the sequence and/or structural identity specified above, shares at least one functional characteristic with the relevant intact substance. In some embodiments, a characteristic portion may be biologically active. In some embodiments, a characteristic portion of a substance differentiates the substance from other substances.

Certain Agents Useful as First Agents/Capture Molecules

In some embodiments, the present disclosure provides an agent which comprises an agent which can bind to a binding moiety as described herein. In some embodiments, such an agent is a first agent as described herein. In some embodiments, such an agent is or comprises a capture molecule as described herein. In some embodiments, such an agent is or comprises a protein or a polypeptide. In some embodiments, a protein or a polypeptide comprises a functional group that can react with another functional group, e.g., of a second agent as described herein. In some embodiments, a functional group is or comprises —COOH, or a salt or activated form thereof. In some embodiments, such a functional group may react with another functional group, e.g., comprising a carbon to which a leaving group is attached. In some embodiments, in a reaction —C(O)—O— displaces a leaving group. In some embodiments, a leaving group is —Cl. In some embodiments, a protein or polypeptide is or comprises dehalogenase. In some embodiments, a protein or polypeptide is or comprises a haloalkane dehalogenase. In some embodiments, —COOH of an acid residue serves as a functional group for reactions with other functional groups, e.g., those of other agents. In some embodiments, a protein or polypeptide is expressed in a cell.

Figure 12A:
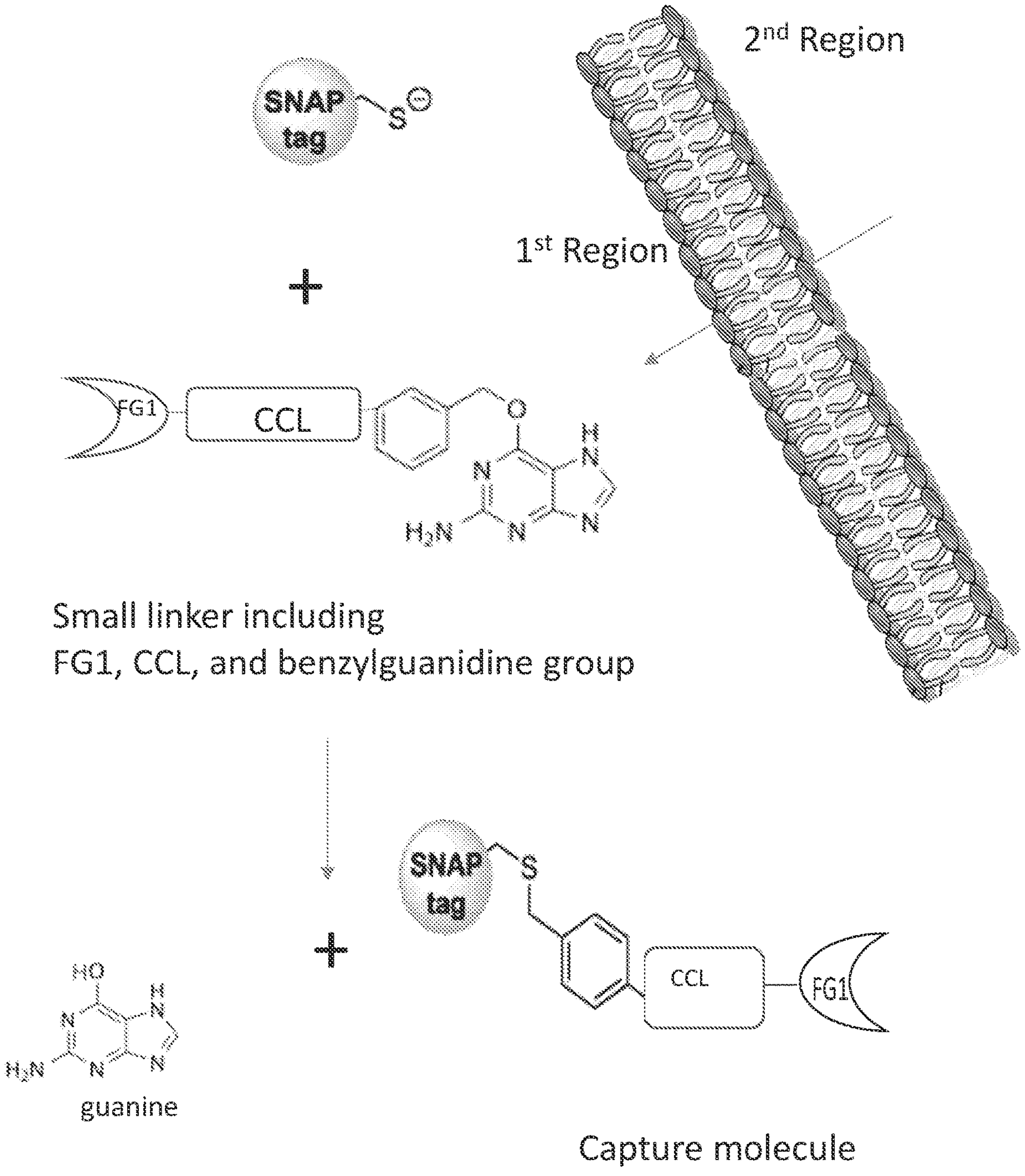
FIGS. 12A-12B are drawings showing a non-limiting embodiment of the invention where the capture molecule includes a modification of a SNAP-tag protein.

In some embodiments, an agent consists of or comprises a scaffold agent moiety which is linked to a functional group optionally through a linker. In some embodiments, a linker is or comprise a CCL. In some embodiments, such a functional group can react with a functional group of another agent, e.g., a second agent. In some embodiments, a scaffold agent is or comprises a protein or a polypeptide. In some embodiments, such an agent is constructed by modification of a protein or polypeptide, e.g., one expressed in a cell, by reacting a protein or polypeptide with an agent comprising a functional group. For example, in some embodiments, a protein or polypeptide is or comprises a SNAP tag protein or a characteristic portion thereof, and a suitable reagent for introducing a functional group to a SNAP tag protein or a characteristic portion thereof is an agent as described herein in FIG. 12A. In some embodiments, such an agent has the structure of:

$R^F$-L-FG1, or a salt thereof, wherein FG1 is a functional group, L is a linker, $R^F$ is

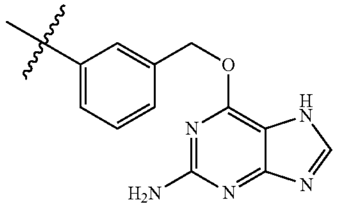 [SMILES: *c1cccc(COc2nc(N)nc3nc[nH]c23)c1]

or Cl.

In some embodiments, $R^F$ is —Cl. In some embodiments, $R^F$ is

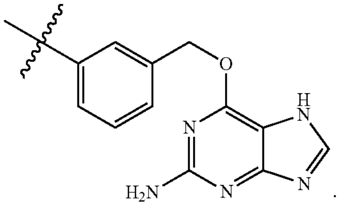 [SMILES: *c1cccc(COc2nc(N)nc3nc[nH]c23)c1]

In some embodiments, such an agent has the structure of Cl-L-FG1 or a salt thereof, wherein FG1 is a functional group. In some embodiments, a linker is or comprises a CCL.

In some embodiments, each linker, e.g., L, is independently a covalent bond, or a bivalent optionally substituted, linear or branched $C_{1-30}$ group comprising one or more aliphatic moieties, aryl moieties, heteroaliphatic moieties each independently having 1-10 heteroatoms, heteroaromatic moieties each independently having 1-10 heteroatoms, or a combination of one or more of such moieties, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, —N═N—, -Cy-, —C(R')$_2$—, —O—, —S—, —S—S—, —N(R')—, —Si(R')$_2$—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, an amino acid residue, or —[(—O—C(R')$_2$—C(R')$_2$—)$_n$]—, wherein n is 1-20; each -Cy- is independently an optionally substituted bivalent monocyclic, bicyclic or polycyclic group wherein each monocyclic ring is independently selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —OR, —C(O)R, —$CO_2$R, or —$SO_2$R;

each R is independently —H, or an optionally substituted group selected from $C_{1-20}$ aliphatic, $C_{1-20}$ heteroaliphatic having 1-10 heteroatoms, $C_{6-20}$ aryl, $C_{6-20}$ arylaliphatic, $C_{6-20}$ arylheteroaliphatic having 1-10 heteroatoms, 5-20 membered heteroaryl having 1-10 heteroatoms, and 3-20 membered heterocyclyl having 1-10 heteroatoms, or two R groups are optionally and independently taken together to form a covalent bond, or:

two or more R groups on the same atom are optionally and independently taken together with the atom to form an optionally substituted, 3-20 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

In some embodiments, a heteroatom is an atom that is not hydrogen or carbon. In some embodiments, each heteroatom is independently selected from oxygen, nitrogen, sulfur, phosphorus and silicon, including oxidized forms thereof.

In some embodiments, L comprises a CCL. In some embodiments, L is -$L^1$-CCL-$L^2$-, wherein each of $L^1$, CCL, and $L^2$ is independently a covalent bond, or a bivalent optionally substituted, linear or branched $C_{1-20}$ (e.g., $C_{1-5}$, $C_{1-10}$, $C_{1-15}$) group comprising one or more aliphatic moieties, aryl moieties, heteroaliphatic moieties each independently having 1-10 heteroatoms, heteroaromatic moieties each independently having 1-10 heteroatoms, or a combination of one or more of such moieties, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, —N═N—, -Cy-, —C(R')$_2$—, —O—, —S—, —S—S—, —N(R')—, —Si(R')$_2$—, —C(O)—, —C(S)—, —C(NR')—, —C(O)N(R')—, —C(O)C(R')$_2$N(R')—, —N(R')C(O)N(R')—, —N(R')C(O)O—, —S(O)—, —S(O)$_2$—, —S(O)$_2$N(R')—, —C(O)S—, —C(O)O—, an amino acid residue, or —[(—O—C(R')$_2$—C(R')$_2$—)$_n$]—, wherein n is 1-20.

In some embodiments, $L^1$ is bonded to —$R^F$. In some embodiments, $L^1$ is bonded to —Cl. In some embodiments, $L^1$ is a linear $C_{1-10}$ bivalent alkylene group, wherein one or more methylene units is optionally and independently replaced with —$CH_2$—O—$CH_2$— or —O—. In some embodiments, $L^1$ is a linear $C_{1-10}$ bivalent alkylene group. In some embodiments, $L^2$ is a linear $C_{1-10}$ bivalent alkylene group, wherein one or more methylene units is optionally and independently replaced with —$CH_2$—O—$CH_2$— or —O—. In some embodiments, $L^2$ is a linear $C_{1-10}$ bivalent alkylene group.

As those skilled in the art will appreciate, various CCLs may be utilized in accordance with the present disclosure in various agents of the present disclosure. In some embodiments, a CCL is or comprises —C(O)O—. In some embodiments, a CCL is or comprises

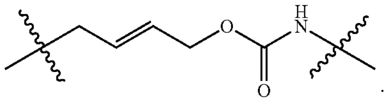 [SMILES: *C/C=C/COC(=O)N*]

In some embodiments, a CCL is or comprises

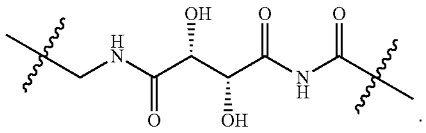 [SMILES: *CNC(=O)[C@H](O)[C@@H](O)C(=O)NC(*)=O]

In some embodiments, a CCL is or comprises

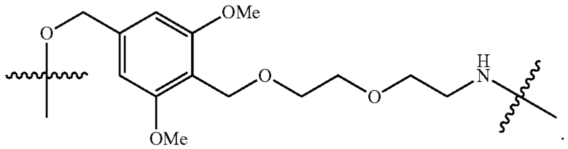 [SMILES: *NCCOCCOCc1c(OC)cc(CO*)cc1OC]

In some embodiments, a CCL is or comprises

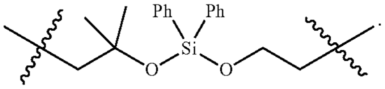 [SMILES: *CCO[Si](OC(C)(C)C*)(c1ccccc1)c1ccccc1]

In some embodiments, a CCL is or comprises

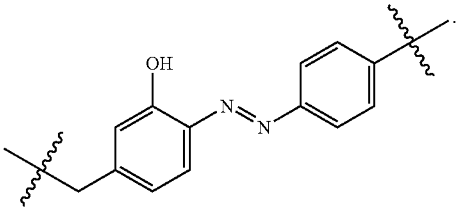 [SMILES: *Cc1ccc(/N=N/c2ccc(*)cc2)c(O)c1]

In some embodiments, a CCL is or comprises

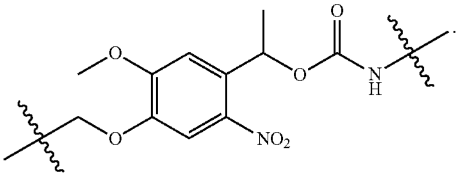 [SMILES: *COc1cc([N+](=O)[O-])c(C(C)OC(=O)N*)cc1OC]

In some embodiments, a CCL is or comprises

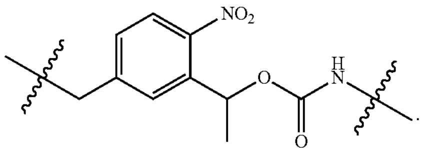 [SMILES: *Cc1ccc([N+](=O)[O-])c(C(C)OC(=O)N*)c1]

In some embodiments, a CCL is or comprises

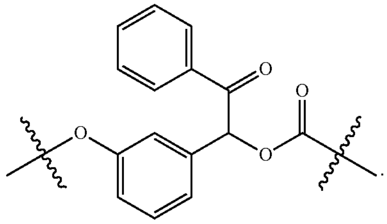 [SMILES: *Oc1cccc(C(OC(*)=O)C(=O)c2ccccc2)c1]

In some embodiments, a CCL is or comprises

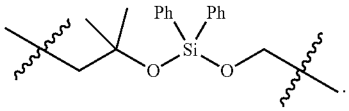 [SMILES: *CO[Si](OC(C)(C)C*)(c1ccccc1)c1ccccc1]

In some embodiments, a CCL is or comprises

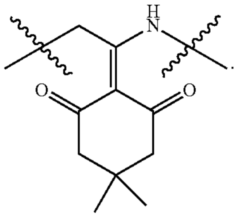 [SMILES: *CC(N*)=C1C(=O)CC(C)(C)CC1=O]

In some embodiments, a CCL is or comprises

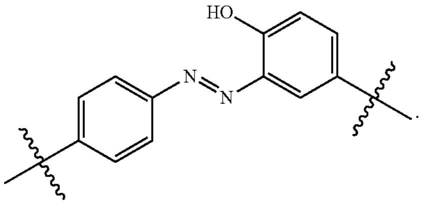 [SMILES: *c1ccc(/N=N/c2cc(*)ccc2O)cc1]

In some embodiments, each of such CCL moieties may be optionally substituted (e.g., optionally substituted

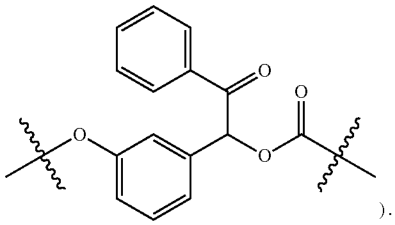 [SMILES: *Oc1cccc(C(OC(*)=O)C(=O)c2ccccc2)c1]

).

In some embodiments, a CCL is or comprises —C(O)—O—. In some embodiments, a CCL is or comprises vicinal diols. In some embodiments, a CCL is or comprises —N=N—. In some embodiments, a CCL is or comprises —Ar—N=N—Ar—, wherein each Ar is independently an optionally substituted aromatic moiety. Certain CCLs and uses thereof are described in FIGS. 8A-8E as examples.

In some embodiments, L is a covalent bond. In some embodiments, $L^1$ is a covalent bond. In some embodiments, $L^2$ is a covalent bond.

In some embodiments, a linker comprises a structural linker which is stable under isolation, lysis, and/or enrichment conditions.

In some embodiments, an agent, e.g., an agent useful as a capturing agent, a first agent, etc., has the structure of:

$R^C$-L-FG1, or salt thereof, wherein $R^C$ is a scaffold agent moiety, FG1 is a functional group, and L is as described herein. In some embodiments, $R^C$ is or comprises a protein or polypeptide moiety. In some embodiments, $R^C$ is or comprises a protein or polypeptide expressed in a cell. In some embodiments, $R^C$ is or comprises a halotag protein moiety. In some embodiments, $R^C$ is or comprises a SNAP tag protein moiety. In some embodiments, L is a covalent bond, and FG1 is a functional group of an amino acid of an amino acid residue. In some embodiments, FG1 is —COOH or a salt form thereof. In some embodiments, FG1 is or comprises —$N_3$. In some embodiments, FG1 is or comprises an alkyne. In some embodiments, an alkyne is a terminal alkyne. In some embodiments, an alkyne is an alkyne in a ring. In some embodiments, an alkyne is in a strained ring. In some embodiments, FG1 is or comprise an alkene. In some embodiments, an alkene is in a strained ring. In some embodiments, FG1 is or comprises a dipole. In some embodiments, FG1 is or comprise a diene or heterodiene. In some embodiments, a dipole or a diene or heterodiene is suitable for cycloaddition reaction with an alkene or an alkyne.

In some embodiments, as a reference, a scaffold agent moiety comprises one or more mutations. In some embodiments, In some embodiments, a scaffold agent moiety does not significantly bind to another agent, e.g., a second agent; rather, an agent binds to another agent, e.g., a second agent, through reaction of its functional group with a functional group of another agent, e.g., a second agent. Those skilled in the art appreciate that various reactions and functional groups, including many bioorthogonal ones, are available and can be utilized in accordance with the present disclosure. For example, in some embodiments, a reaction is a cycloaddition reaction, e.g., a [3+2] or [4+2] reaction. In some embodiments, a reaction is click reaction, and one functional group is azide, and the other is an alkyne, e.g., a terminal alkyne, an activated alkyne in a ring system which can comprises certain levels of ring strain, etc. Certain examples are described in FIG. 11.

In some embodiments, a functional group is connected to a scaffold agent moiety through a linker which is or comprises a CCL. In some embodiments, after cleavage of a CCL, e.g., through pure chemical and/or enzymatic process, a product moiety formed by a reaction between a functional group of an agent (e.g., a first agent) with a functional group of another agent (e.g., a second agent) becomes a releasing moiety or a characteristic portion thereof, e.g., of a product agent (e.g., a product agent of a second agent). In some embodiments, a releasing moiety is attached to a scaffold agent moiety, or a candidate compound moiety, optionally through a linker. In some embodiments, a scaffold agent or candidate compound which is linked to a releasing moiety optionally through a linker is or comprises a stapled peptide moiety as described herein. In some embodiments, a linker in a product agent is typically a stable linker. In some embodiments, a linker in a product agent does not contain a CCL. Among other things, such linker may provide desired stability for isolation and/or characterization of a product agent.

In some embodiments, provided agents, e.g., those useful as first agents, typically do not cross barriers. In some embodiments, for other agents to react with such agents, such other agents are required to cross a barrier to contact such agents.

In some embodiments, agents utilized as first agents are in a first region, which agents to be tested for barrier crossing is directly administrated in a second region, wherein the first region is separated from the second region by the barrier. In some embodiments, a barrier is a cell membrane, and a first region is intracellular. In some embodiments, to contact an agent which is a first agent in a first region, an agent, e.g., a second agent administered to a second region, will need to cross the barrier, e.g., permeating a cell membrane. In some embodiments, agents utilized as first agents do not cross barriers (or at very low levels). In some embodiments, membrane permeation or barrier-crossing may occur through a number of mechanisms including but not limited to diffusion.

In some embodiments, an agent is or comprise a capture molecule as described herein. In some embodiments, an agent is a capture molecule as described herein.

Certain Agents Comprising Binding Moieties, Useful as Second Agents or that May Cross Barriers Among other things, the present disclosure provides technologies for assessing barrier, e.g., cell membrane, or various types of agents. In some embodiments, such agents are referred to as scaffold agents. In some embodiments, an agent is or comprises a small molecule compound. In some embodiments, an agent is or comprises a nucleic acid agent. In some embodiments, an agent is or comprises an oligonucleotide agent. In some embodiments, an agent is or comprises a protein agent. In some embodiments, an agent is or comprises a polypeptide agent. In some embodiments, an agent is or comprises a peptide agent. In some embodiments, an agent is or comprises a stapled peptide agent. In some embodiments, an agent is a candidate compound as described herein.

In some embodiments, a scaffold agent, e.g., one described above, is modified to provide an agent that comprises a binding moiety which can bind to and/or react with another agent, e.g., a first agent, after an agent crosses a barrier.

In some embodiments, a provided agent comprises a scaffold agent moiety or a characteristic portion thereof which is linked to a functional group optionally through a linker. In some embodiments, a scaffold agent or a characteristic portion thereof is or comprises an amino acid sequence, and a functional group is linked to the N-terminus of the sequence. In some embodiments, a scaffold agent is or comprises an amino acid sequence, and a functional group is linked to the C-terminus of the sequence. In some embodiments, a scaffold agent is or comprises an amino acid sequence, and a functional group is linked to a side chain. In some embodiments, two or more amino acid residues are stapled.

In some embodiments, a scaffold agent is or comprises a stapled peptide. In some embodiments, a stapled peptide is a stitched peptide. In some embodiments, a stapled peptide is described in U.S. Pat. No. 8,957,026, WO 2005/044839, WO 2008/061192, WO 2008/095063, WO 2008/121767, WO 2010/011313, WO 2011/008260, WO 2012/174423, WO 2012/174409, WO 2014/197821, WO 2008/137633, WO 2009/042237, WO 2009/108261, WO 2010/042225, WO 2010/068684, WO 2010/148335, WO 2011/094708, WO 2012/006598, WO 2012/065181, WO 2012/142604, WO 2013/055949, WO 2013/102211, WO 2013/142281, WO 2014/144768, WO 2014/144148, WO 2014/151369, WO 2016/149613, WO 2017/004591, WO 2017/040323, WO 2017/040329, the stapled peptides of each of which are independently incorporated herein by reference. In some embodiments, a stapled peptide is described in U.S. Pat. Nos. 8,592,377, 9,556,227, 10,301,351, 9,163,330, US 2018/010001, U.S. Pat. No. 9,617,309, US 2018/0009847, US 2015/0225471, U.S. Pat. No. 10,081,654, US 2019/0202862, WO 2014/201370, WO 2015/051030, U.S. Pat. No. 10,533,039, US 2020/0239533, the stapled peptides of each of which are independently incorporated herein by reference. In some embodiments, a stapled peptide is described in US 2020/0247858, and WO 2020/041270, the stapled peptides of each of which are independently incorporated herein by reference.

In some embodiments, a functional group is or comprises a leaving group. In some embodiments, a leaving group is displaced when reacting with another functional group. In some embodiments, a leaving group is —Cl. In some embodiments, for example, as described in FIG. 7A, —Cl is displaced by a nucleophilic group, e.g., $—COO^-$.

In some embodiments, an agent, e.g., an agent to be assessed for barrier crossing, an agent administered into a system for barrier crossing, etc., has the structure of:

$R^B$-L-FG2, or a salt thereof, wherein $R^B$ is a scaffold agent moiety, FG2 is a functional group, and L is as described herein. For example, in some embodiments, a scaffold agent moiety is or comprises a peptide moiety. In some embodiments, a scaffold agent moiety is or comprises a stapled peptide moiety. In some embodiments, L is connected to a N-terminus of $R^B$. In some embodiments, L is connected to a C-terminus of $R^B$. In some embodiments, L is connected to a side chain of $R^B$. In some embodiments, FG2 is a functional group that can react with FG1. In some embodiments, FG2 is or comprises $—N_3$. In some embodiments, FG2 is or comprises an alkyne. In some embodiments, an alkyne is a terminal alkyne. In some embodiments, an alkyne is an alkyne in a ring. In some embodiments, an alkyne is in a strained ring. In some embodiments, FG2 is or comprise an alkene. In some embodiments, an alkene is in a strained ring. In some embodiments, FG2 is or comprises a dipole. In some embodiments, FG2 is or comprise a diene or heterodiene. In some embodiments, a dipole or a diene or heterodiene is suitable for cycloaddition reaction with an alkene or an alkyne. In various embodiments, FG1 is one partner of a cycloaddition reaction (e.g., $—N_3$), and FG2 is the other partner of a cycloaddition reaction (e.g., a moiety comprising an alkyne). In some embodiments, FG2 is or comprises a leaving group (e.g., —Cl). In some embodiments, FG2 is a leaving group, and FG1 is or comprises a nucleophile (e.g., —COO—) which can displace a leaving group.

In some embodiments, L is a covalent bond. In some embodiments, L is or comprises a CCL as described herein. In some embodiments, L is $-L^1$-CCL-$L^2$- as described herein. In some embodiments, L does not contain a CCL. In some embodiments, L is optionally substituted bivalent $C_{1-30}$ alkylene wherein one or more methylene units are optionally and independently replaced with —O—. In some embodiments, L is optionally substituted linear bivalent $C_{1-30}$ alkylene wherein one or more methylene units are optionally and independently replaced with —O—. In some embodiments, L is linear bivalent $C_{1-30}$ alkylene wherein one or more methylene units are optionally and independently replaced with —O—. In some embodiments, L is linear bivalent $C_{1-30}$ alkylene.

L may be utilized in various agents of the present disclosure, either as L in a formula, or as a linker, or as another moiety, e.g., $L^P$, which may be L. In some embodiments, -L- is or comprises $—(CH_2)—$. In some embodiments, -L- is or comprises $—(CH_2)_2—$. In some embodiments, -L- is or comprises $—(CH_2)_3—$. In some embodiments, -L- is or comprises $—(CH_2)_4—$. In some embodiments, -L- is or comprises $—(CH_2)_5—$. In some embodiments, -L- is or comprises $—(CH_2)_6—$. In some embodiments, -L- is or comprises $—(CH_2)_2—O—$. In some embodiments, -L- is or comprises $—(CH_2)_2—O—(CH_2)_2—$. In some embodiments, -L- is or comprises $—(CH_2)_2—O—(CH_2)_2O—$. In some embodiments, -L- is or comprises $—(CH_2)_6O(CH_2)_2O(CH_2)_2—$. In some embodiments, -L- is or comprises $—(CH_2)_n—$, wherein n is 1-20. In some embodiments, n is 1, 2, 3, 4, 5, 6, 7, 8, 9, 10, 11, 12, 13, 14, 15, 16, 17, 18, 19, 20.

In some embodiments, -L-FG2 is or comprises $Cl—(CH_2)—$. In some embodiments, -L-FG2 is or comprises $Cl—(CH_2)_2—$. In some embodiments, -L-FG2 is or comprises $Cl—(CH_2)_3—$. In some embodiments, -L-FG2 is or comprises $Cl—(CH_2)_4—$. In some embodiments, -L-FG2 is or comprises $Cl—(CH_2)_5—$. In some embodiments, -L-FG2 is or comprises $Cl—(CH_2)_6—$. In some embodiments, -L-FG2 is or comprises $Cl—(CH_2)_2—O—$. In some embodiments, -L-FG2 is or comprises $Cl—(CH_2)_2—O—(CH_2)_2—$. In some embodiments, -L-FG2 is or comprises $Cl—(CH_2)_2—O—(CH_2)_2O—$. In some embodiments, -L-FG2 is or comprises $Cl—(CH_2)_6O(CH_2)_2O(CH_2)_2—$. In some embodiments, -L-FG2 is or comprises $Cl—(CH_2)_n—$, wherein n is 1-20. In some embodiments, n is 1, 2, 3, 4, 5, 6, 7, 8, 9, 10, 11, 12, 13, 14, 15, 16, 17, 18, 19, 20.

In some embodiments, FG2 is or comprises $Cl—(CH_2)—$. In some embodiments, FG2 is or comprises $Cl—(CH_2)_2—$. In some embodiments, FG2 is or comprises $Cl—(CH_2)_3—$. In some embodiments, FG2 is or comprises $Cl—(CH_2)_4—$. In some embodiments, FG2 is or comprises $Cl—(CH_2)_5—$. In some embodiments, FG2 is or comprises $Cl—(CH_2)_6—$. In some embodiments, FG2 is or comprises $Cl—(CH_2)_2—O—$. In some embodiments, FG2 is or comprises $Cl—(CH_2)_2—O—(CH_2)_2—$. In some embodiments, FG2 is or comprises $Cl—(CH_2)_2—O—(CH_2)_2O—$. In some embodiments, FG2 is or comprises $Cl—(CH_2)_6O(CH_2)_2O(CH_2)_2—$. In some embodiments, FG2 is or comprises $Cl—(CH_2)_n—$, wherein n is 1-20. In some embodiments, n is 1, 2, 3, 4, 5, 6, 7, 8, 9, 10, 11, 12, 13, 14, 15, 16, 17, 18, 19, 20.

In some embodiments, a binding moiety is or comprises a functional group and optionally a linker as described herein. In some embodiments, a binding moiety is or comprises -L-FG2, wherein each of L and FG2 is as described herein.

In some embodiments, agents comprising scaffold agent moieties and functional groups optionally linked by linkers, or agents comprising scaffold agent moieties and binding moieties, do not significantly change properties of the corresponding scaffold agents (e.g., candidate compounds). In some embodiments, such agents change sizes and/or molecular weights of corresponding scaffold agents by no more than 1%, 2%, 3%, 4%, 5%, 6%, 7%, 8%, 9%, 10%, 11%, 12%, 13%, 14%, 15%, 16%, 17%, 18%, 19%, 20%, 25%, or 30%. In some embodiments, binding moieties, functional groups and/or linkers change polarity, solubility, and/or Log P, etc. of scaffold agents by no more than 1%, 2%, 3%, 4%, 5%, 6%, 7%, 8%, 9%, 10%, 11%, 12%, 13%, 14%, 15%, 16%, 17%, 18%, 19%, 20%, 25%, or 30%.

Certain useful agents are described below:

| SEQ ID NO | |
|---|---|
| 1 | HaloTagO2-Leu-Thr-Phe-R8-Ala-Tyr-Trp-Ala-GIn-Cba-S5-Ser-Ala-Ala-NH2 |
| 2 | HaloTagO2-Leu-Thr-Phe-R8-Glu-Tyr-Trp-Ala-Gln-Cba-S5-Ser-Ala-Ala-NH2 |
| 3 | HaloTagO2-Leu-Thr-Phe-R8-Thr-Tyr-Trp-Ala-Gln-Cba-S5-Ser-Ala-Ala-NH2 |
| 4 | HaloTagO2-Leu-Thr-Phe-R8-Ala-Tyr-Trp-Ala-GIn-Cba-S5-Ser-Ala-Ala-NHMe |
| 5 | HaloTagO2-Leu-Thr-Phe-R8-Glu-Tyr-Trp-Ala-Gln-Cba-S5-Ser-Ala-Ala-NHMe |
| 6 | HaloTagO2-Leu-Thr-Phe-R8-Thr-Tyr-Trp-Ala-Gln-Cba-S5-Ser-Ala-Ala-NHMe |
| 7 | HaloTagO2-Leu-Thr-Phe-R8-Glu-Tyr-Trp-Ala-Ala-Cba-S5-Ser-Ala-Ala-NH2 |
| 8 | HaloTagO2-Leu-Thr-Phe-R8-Glu-Tyr-Trp-Ala-Thr-Cba-S5-Ser-Ala-Ala-NH2 |
| 9 | HaloTagO2-Leu-Thr-Phe-R8-Glu-Tyr-Trp-Ala-Ala-Cba-S5-Ser-Ala-Ala-NHMe |
| 10 | HaloTagO2-Leu-Thr-Phe-R8-Glu-Tyr-Trp-Ala-Gln-Cba-S5-Ser-Ala-Ala-NHMe |
| 11 | HaloTagO2-Leu-Thr-Phe-R8-Glu-Tyr-Trp-Ala-Thr-Cba-S5-Ser-Ala-Ala-NHMe |
| 12 | HaloTagO2-Leu-Thr-Phe-ReN-Ala-Tyr-Trp-Ala-Gln-Cba-Az-Ser-Ala-Ala-NH2 |
| 13 | HaloTagO2-Leu-Thr-Phe-ReN-Glu-Tyr-Trp-Ala-Gln-Cba-Az-Ser-Ala-Ala-NH2 |
| 14 | HaloTagO2-Leu-Thr-Phe-ReN-Thr-Tyr-Trp-Ala-Gln-Cba-Az-Ser-Ala-Ala-NH2 |
| 15 | HaloTagO2-Leu-Thr-Phe-ReN-Ala-Tyr-Trp-Ala-Gln-Cba-Az-Ser-Ala-Ala-NHMe |
| 16 | HaloTagO2-Leu-Thr-Phe-ReN-Glu-Tyr-Trp-Ala-Gln-Cba-Az-Ser-Ala-Ala-NHMe |
| 17 | HaloTagO2-Leu-Thr-Phe-ReN-Thr-Tyr-Trp-Ala-Gln-Cba-Az-Ser-Ala-Ala-NHMe |
| 18 | HaloTagO2-Leu-Thr-Phe-ReN-Glu-Tyr-Trp-Ala-Ala-Cba-Az-Ser-Ala-Ala-NH2 |
| 19 | HaloTagO2-Leu-Thr-Phe-ReN-Glu-Tyr-Trp-Ala-Thr-Cba-Az-Ser-Ala-Ala-NH2 |
| 20 | HaloTagO2-Leu-Thr-Phe-ReN-Glu-Tyr-Trp-Ala-Ala-Cba-Az-Ser-Ala-Ala-NHMe |
| 21 | HaloTagO2-Leu-Thr-Phe-ReN-Glu-Tyr-Trp-Ala-Gln-Cba-Az-Ser-Ala-Ala-NHMe |
| 22 | HaloTagO2-Leu-Thr-Phe-ReN-Glu-Tyr-Trp-Ala-Thr-Cba-Az-Ser-Ala-Ala-NHMe |

wherein HaloTagO2 is -L-FG2 and is bonded to N-terminus of a peptide, wherein -L-FG2 is $Cl—(CH_2)_6O(CH_2)_2O(CH_2)_2NHC(O)(CH_2)_2C(O)—$, wherein the peptide chain is a scaffold agent moiety. In some embodiments, a scaffold agent is:

| SEQ ID NO | |
|---|---|
| 23 | $R^N$-Leu-Thr-Phe-R8-Ala-Tyr-Trp-Ala-Gln-Cba-S5-Ser-Ala-Ala-NH2 |
| 24 | $R^N$-Leu-Thr-Phe-R8-Glu-Tyr-Trp-Ala-Gln-Cba-S5-Ser-Ala-Ala-NH2 |
| 25 | $R^N$-Leu-Thr-Phe-R8-Thr-Tyr-Trp-Ala-Gln-Cba-S5-Ser-Ala-Ala-NH2 |
| 26 | $R^N$-Leu-Thr-Phe-R8-Ala-Tyr-Trp-Ala-Gln-Cba-S5-Ser-Ala-Ala-NHMe |
| 27 | $R^N$-Leu-Thr-Phe-R8-Glu-Tyr-Trp-Ala-Gln-Cba-S5-Ser-Ala-Ala-NHMe |
| 28 | $R^N$-Leu-Thr-Phe-R8-Thr-Tyr-Trp-Ala-Gln-Cba-S5-Ser-Ala-Ala-NHMe |
| 29 | $R^N$-Leu-Thr-Phe-R8-Glu-Tyr-Trp-Ala-Ala-Cba-S5-Ser-Ala-Ala-NH2 |
| 30 | $R^N$-Leu-Thr-Phe-R8-Glu-Tyr-Trp-Ala-Thr-Cba-S5-Ser-Ala-Ala-NH2 |
| 31 | $R^N$-Leu-Thr-Phe-R8-Glu-Tyr-Trp-Ala-Ala-Cba-S5-Ser-Ala-Ala-NHMe |

-continued

| SEQ ID NO | |
|---|---|
| 32 | $R^N$-Leu-Thr-Phe-R8-Glu-Tyr-Trp-Ala-Gln-Cba-S5-Ser-Ala-Ala-NHMe |
| 33 | $R^N$-Leu-Thr-Phe-R8-Glu-Tyr-Trp-Ala-Thr-Cba-S5-Ser-Ala-Ala-NHMe |
| 34 | $R^N$-Leu-Thr-Phe-ReN-Ala-Tyr-Trp-Ala-Gln-Cba-Az-Ser-Ala-Ala-NH2 |
| 35 | $R^N$-Leu-Thr-Phe-ReN-Glu-Tyr-Trp-Ala-Gln-Cba-Az-Ser-Ala-Ala-NH2 |
| 36 | $R^N$-Leu-Thr-Phe-ReN-Thr-Tyr-Trp-Ala-Gln-Cba-Az-Ser-Ala-Ala-NH2 |
| 37 | $R^N$-Leu-Thr-Phe-ReN-Ala-Tyr-Trp-Ala-Gln-Cba-Az-Ser-Ala-Ala-NHMe |
| 38 | $R^N$-Leu-Thr-Phe-ReN-Glu-Tyr-Trp-Ala-Gln-Cba-Az-Ser-Ala-Ala-NHMe |
| 39 | $R^N$-Leu-Thr-Phe-ReN-Thr-Tyr-Trp-Ala-Gln-Cba-Az-Ser-Ala-Ala-NHMe |
| 40 | $R^N$-Leu-Thr-Phe-ReN-Glu-Tyr-Trp-Ala-Ala-Cba-Az-Ser-Ala-Ala-NH2 |
| 41 | $R^N$-Leu-Thr-Phe-ReN-Glu-Tyr-Trp-Ala-Thr-Cba-Az-Ser-Ala-Ala-NH2 |
| 42 | $R^N$-Leu-Thr-Phe-ReN-Glu-Tyr-Trp-Ala-Ala-Cba-Az-Ser-Ala-Ala-NHMe |
| 43 | $R^N$-Leu-Thr-Phe-ReN-Glu-Tyr-Trp-Ala-Gln-Cba-Az-Ser-Ala-Ala-NHMe |
| 44 | $R^N$-Leu-Thr-Phe-ReN-Glu-Tyr-Trp-Ala-Thr-Cba-Az-Ser-Ala-Ala-NHMe |

wherein $R^N$ is —H or —Ac. In some embodiments, $R^N$ is —H. In some embodiments, $R^N$ is —Ac. As appreciated by those skilled in the art, R8 and S5, and ReN and Az can be stapled by olefin metathesis. In some embodiments, barrier-crossing properties of a scaffold agent is determined based on, associated with, related to and/or inferred from, barrier-crossing properties of an agent administered to contact a barrier (e.g., agents comprising -L-FG2, such as those comprising HaloTagO2).

Agents, when administered to contact a barrier to assess barrier-crossing, are typically administered to a region that absence of agents utilized as first agents/capture molecules. In some embodiments, to bind to or react with first agents/capture molecules at a significant level, such agents are required to cross barriers.

Certain Complexes

In some embodiments, the present disclosure provides complexes. In some embodiments, a complex is formed by one agent (e.g., a first agent) binding to another (e.g., a second agent). In some embodiments, a complex is formed by one agent reacting with another. In some embodiments, two agents are covalently linked to form a complex. In some embodiments, FG1 and FG2 of two agents react such a complex is formed.

In some embodiments, a complex is formed after an agent, e.g., a second agent, crosses a barrier and contacts another agent, e.g., a first agent.

In some embodiments, a reaction forming a complex is a bioorthogonal reaction. Such reactions are widely known in the art and can be utilized in accordance with the present disclosure. In some embodiments, such reactions occur in a second region. In some embodiments, such reactions occur inside a cell.

In some embodiments, a complex comprises one or more CCLs. In some embodiments, one or more CCLs are independently from agents that form a complex (e.g., see FIG. 9B). In some embodiments, a CCL is a reaction product of two functional groups, e.g., FG1 and FG2 (e.g., see FIG. 7A).

In some embodiments, a complex agent has the structure of:

$R^C$-L-$L^P$-L-$R^B$, or a salt thereof, wherein $L^P$ is L and each of the other variable is independently as described herein. In some embodiments, $R^C$-L- is as described for an agent having the structure of $R^C$-L-FG1 or a salt thereof. In some embodiments, $R^C$-L- is from an agent having the structure of $R^C$-L-FG1 or a salt thereof. In some embodiments, $R^B$-L- is as described for an agent having the structure of $R^B$-L-FG1 or a salt thereof. In some embodiments, $R^C$-L- is from an agent having the structure of $R^B$-L-FG1 or a salt thereof. In some embodiments, $L^P$ is or comprises a product moiety formed by FG1 and FG2 reacting with each other. In some embodiments, FG1 is or comprises —COOH or a salt or activated form, and FG2 is or comprises a leaving group such as —Cl. In some embodiments, $L^P$ is or comprises —C(O)—O—. In some embodiments, FG1 and FG2 are two reaction partners of a cycloaddition reaction, e.g., click chemistry reaction, and $L^P$ is or comprises a cycloaddition product moiety, e.g., a triazole moiety, a 6-membered ring moiety, etc. In some embodiments, $L^P$ is or comprises -Cy-. In some embodiments, -Cy-comprises at least one partially unsaturated or aromatic monocyclic ring. In some embodiments, -Cy- is partially unsaturated. In some embodiments, -Cy- is aromatic.

In some embodiments, L bonded to $R^C$ is or comprises a CCL. In some embodiments, L bonded to $R^B$ is or comprises a CCL. In some embodiments, both L independently are or comprise a CCL. In some embodiments, L bonded to $R^B$ is cleaved to provide a product agent, e.g., one has the structure of $R^P$-L-FG3 or a salt thereof, which is different from $R^B$-L-FG2. In some embodiments, L bonded to $R^C$ is cleaved to provide a product agent which is different from $R^B$-L-FG2. In some embodiments, a product agent has the structure of H-L-$L^P$-L-$R^B$, wherein the L bonded to H is the same as or, in many embodiments, is different from the L bonded to $R^C$. In some embodiments, FG3 or a releasing moiety in a product agent is or comprises H-L-$L^P$-. In some embodiments, FG3 is or comprises -Cy- as described herein. In some embodiments, FG3 is -Cy-L-H.

In some embodiments, each L in $R^C$-L-$L^P$-L-$R^B$ contains no CCL that is cleaved during production of product agents. In some embodiments, $L^P$ is or comprises a CCL which is cleaved. For example, in some embodiments, $L^P$ is or comprises —C(O)O— which is cleaved to provide a product agent, e.g., one has the structure of $R^P$-L-FG3 or a salt thereof. In some embodiments, a product agent has the structure of $R^C$-L-COOH or a salt thereof, wherein $R^C$-L- is the same or different as $R^C$-L- in $R^C$-L-FG1 or a salt thereof. In some embodiments, a product agent has the structure of $R^P$-L-OH or a salt thereof, wherein $R^P$-L- is the same or different as $R^B$-L- in $R^B$-L-FG2 or a salt thereof. In some embodiments, they are the same. In some embodiments, they are different.

In some embodiments, complexes are enriched. For example, in some embodiments, complexes can be enriched from a composition, e.g., cell lysate, through affinity enrichment. In some embodiments, enrichment is achieved utilizing an antibody. In some embodiments, an antibody recognizes and binds a complex. In some embodiments, an antibody recognizes and binds to a protein or polypeptide moiety of an agent in a complex (e.g., a first agent or capture molecule). In some embodiments, a complex is enriched using a tag. In some embodiments, an agent in a complex, e.g., an agent utilized as a first agent/capture molecule comprises a tag. In some embodiments, a tag is or comprises a His tag (e.g., a hexahistidine tag). In some embodiments, a tag is or comprises a hexahistidine tag. In some embodiments, a tag is or comprises a GST tag. In some embodiments, a tag is or comprises a FLAG tag.

Among other things, enrichment may increase accuracy, sensitivity, signal to noise ratio, etc.

In some embodiments, complexes are not enriched.

In some embodiments, complexes are converted to product agents, e.g., by cleavage of CCLs. In some embodiments, a CCL is cleaved by a chemical condition, e.g., a basic condition. In some embodiments, a basic condition is strong enough to cleave a CCL, e.g., a CCL that is or comprises —CO(O)— but would not significantly damage scaffold agent moieties, e.g., that are or comprise peptide moieties. In some embodiments, a condition utilizes a base, such as an amine base. In some embodiments, a condition has a pH of about 9, 10, 11, 12, 13 or 14. In some embodiments, a pH is or about 9. In some embodiments, a pH is or about 10. In some embodiments, a pH is or about 11. In some embodiments, a pH is or about 12. In some embodiments, a pH is or about 13. In some embodiments, a pH is or about 14. In some embodiments, cleavage includes catalytic cleavage (e.g., promoted by a metal catalyst), acidic cleavage, oxidation cleavage, reduction cleavage, light-promoted cleavage (e.g., cleavage provided by UV light), etc.

In some embodiments, a CCL is cleaved utilizing one or more enzymes. For example, in some embodiments, CCLs that are or comprise —C(O)O— may be cleaved by hydrolases such as esterases. In some embodiments, cleavage is or comprises catalytic cleavage (e.g., promoted by a metal catalyst), acidic cleavage, basic cleavage, oxidation cleavage, reduction cleavage, light-promoted cleavage (e.g., cleavage provided by UV light), etc. In some embodiments, cleavage is or comprises an acidic cleavage. In some embodiments, an acid cleavage is or comprises 10% formic acid. In some embodiments, a cleavage is or comprises a basic cleavage, e.g., a condition described in the Examples.

Those skilled will appreciate that other enzymes may also be utilized in accordance with the present disclosure.

In some embodiments, a complex may be formed transiently. In some embodiments, a complex may be an intermediate during a transformation process, e.g., a —Cl to —OH conversion process by a dehalogenase. In some embodiments, an agents, e.g., having the structure of $R^B$-L-FG2 or a salt thereof, or a second agent, may be converted into a product agent, e.g., having the structure of $R^P$-L-FG2 or a salt thereof, without a cleavage manipulation. One of such examples is conversion of $R^B$-L-Cl or a salt thereof to $R^P$-L-OH or a salt thereof by a dehalogenase. In some embodiments, an enzyme is a mutant enzyme, e.g., a mutant dehalogenase whose hydrolase activity is greatly reduced or removed such that a complex of two agents may be stably formed, enriched and/or further processed to provide product agents.

Certain Product Agents

In various embodiments, reactions of the present disclosure provide product agents. Particularly, in some embodiments, after an agent crosses a barrier, it provides, through one or more steps and/or with one or more other agents, to provide a product agent which can be detected and to determine barrier-crossing of an agent. In some embodiments, a product agent is formed after cleavage of a complex.

In some embodiments, a product agent, e.g., one utilized for detection, comprises a scaffold agent moiety as described herein linked to a releasing moiety optionally through a linker. In some embodiments, a linker is L. In some embodiments, a scaffold agent is an agent whose barrier-crossing is to be determined. Various scaffold agents are described herein, for example, in some embodiments, a scaffold agent is or comprises a stapled peptide.

In some embodiments, a product agent and an agent comprising a binding moiety or a functional group such as FG2 share the same scaffold agent moiety or a characteristic portion thereof. In some embodiments, a product agent has the structure of:

$R^P$-L-FG3, or a salt thereof, wherein each variable is independently as described herein. In some embodiments, $R^P$ is a scaffold agent moiety. In some embodiments, $R^P$ is the same or share the same characteristic portion as $R^B$. In some embodiments, $R^P$ is the same or share the same characteristic portion as $R^C$. In some embodiments, product agents utilized for detection independently comprise $R^P$ that is the same or share the same characteristic portion as $R^B$. In some embodiments, FG3 is or comprises -$L^P$-L-H or —OH. In some embodiments, FG3 is or comprises -Cy-L-H or —OH. In some embodiments, a releasing moiety is or comprises FG3. In some embodiments, a releasing moiety is or comprises -L-FG3. In some embodiments, -L-FG2 of an agent and -L-FG3 of a product agent are different, while an agent and a product agent share the same scaffold agent moiety or a characteristic portion thereof.

In some embodiments, FG3 is —OH. In some embodiments, FG3 is or comprises a reaction product moiety of FG1 and FG2. In some embodiments, CCL of an agent as a capturing agent is cleaved. In some embodiments, FG3 is H.

In some embodiments, -L-FG3 is or comprises HO—$(CH_2)$—. In some embodiments, -L-FG3 is or comprises HO—$(CH_2)_2$—. In some embodiments, -L-FG3 is or comprises HO—$(CH_2)_3$—. In some embodiments, -L-FG3 is or comprises HO—$(CH_2)_4$—. In some embodiments, -L-FG3 is or comprises HO—$(CH_2)_5$—. In some embodiments, -L-FG3 is or comprises HO—$(CH_2)_6$—. In some embodiments, -L-FG3 is or comprises HO—$(CH_2)_2$—O—. In some embodiments, -L-FG3 is or comprises HO—$(CH_2)_2$—O—$(CH_2)_2$—. In some embodiments, -L-FG3 is or comprises HO—$(CH_2)_2$—O—$(CH_2)_2$O—. In some embodiments, -L-FG3 is or comprises HO—$(CH_2)_6O(CH_2)_2O(CH_2)_2$—. In some embodiments, -L-FG3 is or comprises HO—$(CH_2)_n$—, wherein n is 1-20. In some embodiments, n is 1, 2, 3, 4, 5, 6, 7, 8, 9, 10, 11, 12, 13, 14, 15, 16, 17, 18, 19, 20.

In some embodiments, FG3 is or comprises HO—$(CH_2)$—. In some embodiments, FG3 is or comprises HO—$(CH_2)_2$—. In some embodiments, FG3 is or comprises HO—$(CH_2)_3$—. In some embodiments, FG3 is or comprises HO—$(CH_2)_4$—. In some embodiments, FG3 is or comprises HO—$(CH_2)_5$—. In some embodiments, FG3 is or comprises HO—$(CH_2)_6$—. In some embodiments, FG3 is or comprises HO—$(CH_2)_2$—O—. In some embodiments, FG3 is or comprises HO—$(CH_2)_2$—O—$(CH_2)_2$—. In some embodiments, FG3 is or comprises HO—$(CH_2)_2$—O—$(CH_2)_2$O—. In some embodiments, FG3 is or comprises HO—$(CH_2)_6O(CH_2)_2O(CH_2)_2$—. In some embodiments, FG3 is or comprises HO—$(CH_2)_n$—, wherein n is 1-20. In some embodiments, n is 1, 2, 3, 4, 5, 6, 7, 8, 9, 10, 11, 12, 13, 14, 15, 16, 17, 18, 19, 20.

In some embodiments, a product agent and an administered agent (e.g., which is administered to a system and contact a barrier for assessment of barrier crossing) comprises the same linker.

In some embodiments, a product agent of an administered agent differ in or more properties which can be utilized for detection and for distinguishing a product agent. In some embodiments, a product agent and an administered agent differ in molecular mass and can be detected and distinguished by mass spectrometry.

In some embodiments, a product agent is:

| SEQ ID NO | |
|---|---|
| 45 | $R^P$-L-Leu-Thr-Phe-R8-Ala-Tyr-Trp-Ala-Gln-Cba-S5-Ser-Ala-Ala-NH2 |
| 46 | $R^P$-L-Leu-Thr-Phe-R8-Glu-Tyr-Trp-Ala-Gln-Cba-S5-Ser-Ala-Ala-NH2 |
| 47 | $R^P$-L-Leu-Thr-Phe-R8-Thr-Tyr-Trp-Ala-Gln-Cba-S5-Ser-Ala-Ala-NH2 |
| 48 | $R^P$-L-Leu-Thr-Phe-R8-Ala-Tyr-Trp-Ala-Gln-Cba-S5-Ser-Ala-Ala-NHMe |
| 49 | $R^P$-L-Leu-Thr-Phe-R8-Glu-Tyr-Trp-Ala-Gln-Cba-S5-Ser-Ala-Ala-NHMe |
| 50 | $R^P$-L-Leu-Thr-Phe-R8-Thr-Tyr-Trp-Ala-Gln-Cba-S5-Ser-Ala-Ala-NHMe |
| 51 | $R^P$-L-Leu-Thr-Phe-R8-Glu-Tyr-Trp-Ala-Ala-Cba-S5-Ser-Ala-Ala-NH2 |
| 52 | $R^P$-L-Leu-Thr-Phe-R8-Glu-Tyr-Trp-Ala-Thr-Cba-S5-Ser-Ala-Ala-NH2 |
| 53 | $R^P$-L-Leu-Thr-Phe-R8-Glu-Tyr-Trp-Ala-Ala-Cba-S5-Ser-Ala-Ala-NHMe |
| 54 | $R^P$-L-Leu-Thr-Phe-R8-Glu-Tyr-Trp-Ala-Gln-Cba-S5-Ser-Ala-Ala-NHMe |
| 55 | $R^P$-L-Leu-Thr-Phe-R8-Glu-Tyr-Trp-Ala-Thr-Cba-S5-Ser-Ala-Ala-NHMe |
| 56 | $R^P$-L-Leu-Thr-Phe-ReN-Ala-Tyr-Trp-Ala-Gln-Cba-Az-Ser-Ala-Ala-NH2 |
| 57 | $R^P$-L-Leu-Thr-Phe-ReN-Glu-Tyr-Trp-Ala-Gln-Cba-Az-Ser-Ala-Ala-NH2 |
| 58 | $R^P$-L-Leu-Thr-Phe-ReN-Thr-Tyr-Trp-Ala-Gln-Cba-Az-Ser-Ala-Ala-NH2 |
| 59 | $R^P$-L-Leu-Thr-Phe-ReN-Ala-Tyr-Trp-Ala-Gln-Cba-Az-Ser-Ala-Ala-NHMe |
| 60 | $R^P$-L-Leu-Thr-Phe-ReN-Glu-Tyr-Trp-Ala-Gln-Cba-Az-Ser-Ala-Ala-NHMe |
| 61 | $R^P$-L-Leu-Thr-Phe-ReN-Thr-Tyr-Trp-Ala-Gln-Cba-Az-Ser-Ala-Ala-NHMe |
| 62 | $R^P$-L-Leu-Thr-Phe-ReN-Glu-Tyr-Trp-Ala-Ala-Cba-Az-Ser-Ala-Ala-NH2 |
| 63 | $R^P$-L-Leu-Thr-Phe-ReN-Glu-Tyr-Trp-Ala-Thr-Cba-Az-Ser-Ala-Ala-NH2 |
| 64 | $R^P$-L-Leu-Thr-Phe-ReN-Glu-Tyr-Trp-Ala-Ala-Cba-Az-Ser-Ala-Ala-NHMe |
| 65 | $R^P$-L-Leu-Thr-Phe-ReN-Glu-Tyr-Trp-Ala-Gln-Cba-Az-Ser-Ala-Ala-NHMe |

-continued

| SEQ ID NO | |
|---|---|
| 66 | $R^P$-L-Leu-Thr-Phe-ReN-Glu-Tyr-Trp-Ala-Thr-Cba-Az-Ser-Ala-Ala-NHMe |

wherein $R^P$-L- is HO—$(CH_2)_6O(CH_2)_2O(CH_2)_2NHC(O)(CH_2)_2C(O)$—. As appreciated by those skilled in the art, R8 and S5, and ReN and Az can be stapled by olefin metathesis. Corresponding scaffold agents and agents administered are described above.

Among other things, the provided technologies differ from various other technologies in that they detects product agents that share the same or the same characteristic portions of scaffold agents which are administered to cross barriers. Such an approach can provide significantly improved sensitivity, accuracy, efficiency and/or throughput. As described herein, in some embodiments, multiple agents can be assessed simultaneously (e.g., administered in the same solution for contacting a barrier (e.g., administered to a single well for assessing cell permeability)).

Multiplexing

Among other things, the provided technologies provide surprising efficiency and/or throughput. In some embodiments, a plurality of agents are administered simultaneously, optionally as a single solution, into a single system for assessing barrier crossing, e.g., administered into a single well with cells for assessing cell-membrane crossing. In some embodiments, a plurality of agents share the same functional groups, linkers and/or binding moieties, but different scaffold agent moieties (they are thus useful, among other things, for assess barrier crossing of various scaffold agents). In some embodiments, a plurality of agents share the same functional groups. In some embodiments, agents of a plurality share the same binding moieties but not the same base moieties. In some embodiments, each agent independently comprise a different base moieties. In some embodiments, each agent of the plurality independently has the structure of $R^B$-L-FG2 or a salt thereof. In some embodiments, by assessing one or more properties of agents having the structure of $R^B$-L-FG2 or a salt thereof, one or more properties (e.g., barrier crossing such as cell membrane penetration) of scaffold agents which comprise $R^B$ or characteristic portion thereof but no -L-FG2 can be assessed.

In some embodiments, a plurality of agents are members of a library, e.g., peptide or stapled peptide library. In some embodiments, a crude library is assessed for crossing cell membrane. Various technologies for preparing libraries are known in the art (e.g., Shin et al., Combinatorial Solid Phase Peptide Synthesis and Bioassays, Journal of Biochemistry and Molecular Biology, 38 (5), September 2005, pp. 517-525) and can be utilized in accordance with the present disclosure.

When a plurality of agents are administered and contact a barrier, some or all may cross the barrier. In some embodiments, none of them cross a barrier. In some embodiments, those cross the barrier bind to and/or react with another plurality of agents there, e.g., capturing agents to provide a plurality of complexes.

In some embodiments, agents of another plurality are the same. In some embodiments, they are different.

In some embodiments, each of the agents of another plurality independently has the structure of $R^F$-L-FG1 or a salt thereof. In some embodiments, $R^F$ are the same for agents of the plurality. In some embodiments, $R^F$ are different. In some embodiments, L is the same. In some embodiments, L is different. In some embodiments, FG1 is the same. In some embodiments, FG1 is different.

In some embodiments, each of the agents of another plurality independently has the structure of $R^C$-L-FG1 or a salt thereof. In some embodiments, $R^C$ are the same for agents of the plurality. In some embodiments, $R^C$ are different. In some embodiments, L is the same. In some embodiments, L is different. In some embodiments, FG1 is the same. In some embodiments, FG1 is different. In some embodiments, each agent of another plurality is the same.

In some embodiments, complexes in a plurality share the same reaction product moieties. In some embodiments, they share different reaction product moieties. In some embodiments, they have the same linkers. In some embodiments, linkers are different. In some embodiments, they share a common CCL. In some embodiments, no common CCL is shared. In some embodiments, they share CCLs that can be cleaved at the same condition.

In some embodiments, each of those agent that cross barriers forms a product agent, e.g., through one or more reactions. In some embodiments, a plurality of product agents are provided, e.g., after cleavage of CCLs. In some embodiments, product agents of a plurality share the same releasing moiety. In some embodiments, releasing moieties are different. In some embodiments, linkers are the same. In some embodiments, linkers are different. In some embodiments, product agents of a plurality are assessed under suitable conditions.

Those skilled in the art appreciates that if desired, an agent of a plurality may be assessed individually.

Detection and Data Analysis

As those skilled in the art will appreciate, various methods can be utilized in accordance with the present disclosure to detect and assess levels of product agents. In some embodiments, product agents are assessed using mass spectrometry. In some embodiments, mass spectrometry provides high efficiency.

Many technologies are available for data processing and analysis. Certain useful technologies are described herein. In some embodiments, RPF is utilized. In some embodiments, COR is utilized.

In some embodiments, one or more reference agents are utilized as controls. In some embodiments, a reference agent is a positive reference agent, and can cross a barrier with high efficiency. In some embodiments, a reference agent is a negative reference agent, and can cross a barrier at very low levels if at all.

In some embodiments, positive and/or negative reference agents are administered into the same system together with an agent to be assessed, e.g., a well comprising a barrier, a well comprising a plurality of cells where agents are assessed for cell membrane crossing. In some embodiments, positive and/or negative reference agents are administered separately from agents to be assessed, e.g., in some embodiments, they are administered in separate wells which do not contain agents to be assessed.

Barrier

As appreciated by those skilled in the art, provided technologies can be utilized to assess various types of barriers. In some embodiments, a barrier is or comprises a layer. In some embodiments, a barrier is or comprises a bilayer. In some embodiments, a barrier is or comprises a phospholipid bilayer. In some embodiments, a barrier is or comprises a membrane. In some embodiments, a barrier is or comprises a cell membrane. In some embodiments, a barrier is or comprises an artificial barrier.

In some embodiments, a barrier is or comprises a biological barrier. In some embodiments, a barrier is or comprises a barrier that is relevant in drug delivery. In some embodiments, a barrier is or comprises a barrier that a therapeutic agent needs to cross to be absorbed and/or delivered to its target locations. In some embodiments, a barrier is or comprises one or more layers of cells. In some embodiments, a barrier is a monolayer, e.g., a monolayer utilized in monolayer assays. In some embodiments, a barrier is or comprises a monolayer of cells (e.g., CaCo-2, RRCK, MDCK, etc.). In some embodiments, agents assessed for crossing a barrier (e.g., a monolayer of cells) contact a barrier at one side, and capturing agent and/or product agent if formed is at the other side a barrier Among other things, the present disclosure provides technologies that are particularly useful for assessing cell membrane crossing of various agents as described herein. In some embodiments, agents are administered to systems comprising cells. Those that can cross cell membranes bind to and/or react with agents, e.g., capture molecules, inside cells to form complexes. Complexes are optionally enriched and cleavage to provide product agents, which can be utilized for detection and/or assessment using, e.g., mass spectrometry.

In some embodiments, the present disclosure provides a composition or a system, comprising an agent as described herein and a barrier as described herein. In some embodiments, an agent is a first agent as described herein. In some embodiments, an agent has the structure of $R^C$-L-FG1 or a salt thereof. In some embodiments, an agent has the structure of $R^B$-L-FG2 or a salt thereof. In some embodiments, an agent has the structure of $R^P$-L-FG3 or a salt thereof. In some embodiments, an agent has the structure of $R^C$-L-$L^P$-L-$R^B$ or a salt thereof. In some embodiments, a composition or system comprises a barrier, and one or more or all of a first agent, a second agent, a complex agent and a product agent. In some embodiments, a composition or system comprises a barrier, a first agent, a second agent and a complex agent. In some embodiments, a composition or system comprises a barrier, a first agent, a second agent and a product agent. In some embodiments, a composition or system comprises a barrier, a second agent and a product agent. In some embodiments, a composition or system comprises a barrier, an agent having the structure of $R^C$-L-FG1 or a salt thereof and an agent has the structure of $R^P$-L-FG3 or a salt thereof. In some embodiments, a composition or system comprises a barrier, an agent having the structure of $R^C$-L-FG1 or a salt thereof and an agent has the structure of $R^B$-L-FG2 or a salt thereof. In some embodiments, a composition or system comprises a barrier, an agent having the structure of $R^P$-L-FG3 or a salt thereof and an agent has the structure of $R^B$-L-FG2 or a salt thereof. In some embodiments, a composition or system comprises a barrier, an agent having the structure of $R^P$-L-FG3 or a salt thereof, an agent has the structure of $R^B$-L-FG2 or a salt thereof, and an agent having the structure of $R^C$-L-FG1 or a salt thereof. In some embodiments, a composition or system comprises a barrier, an agent having the structure of $R^C$-L-$L^P$-L-$R^B$ or a salt thereof, an agent has the structure of $R^B$-L-FG2 or a salt thereof, and an agent having the structure of $R^C$-L-FG1 or a salt thereof. In some embodiments, a composition or system comprises a barrier, and one or more or all of an agent having the structure of $R^C$-L-$L^P$-L-$R^B$ or a salt thereof, an agent has the structure of $R^B$-L-FG2 or a salt thereof, an agent has the structure of $R^P$-L-FG2 or a salt thereof, and an agent having the structure of $R^C$-L-FG1 or a salt thereof. In some embodiments, such a composition or system comprises a plurality of cells. In some embodiments, one or more or all of an agent having the structure of $R^C$-L-$L^P$-L-$R^B$ or a salt thereof, an agent has the structure of $R^B$-L-FG2 or a salt thereof, an agent has the structure of $R^P$-L-FG2 or a salt thereof, and an agent having the structure of $R^C$-L-FG1 or a salt thereof are within one or more cells.

In some embodiments, a composition or system comprises one or more or all of a first agent, a second agent, a complex agent and a product agent. In some embodiments, a composition or system comprises a first agent, a second agent and a complex agent. In some embodiments, a composition or system comprises a first agent, a second agent and a product agent. In some embodiments, a composition or system comprises a second agent and a product agent. In some embodiments, a composition or system comprises an agent having the structure of $R^C$-L-FG1 or a salt thereof and an agent has the structure of $R^P$-L-FG3 or a salt thereof. In some embodiments, a composition or system comprises an agent having the structure of $R^C$-L-FG1 or a salt thereof and an agent has the structure of $R^B$-L-FG2 or a salt thereof. In some embodiments, a composition or system comprises an agent having the structure of $R^P$-L-FG3 or a salt thereof and an agent has the structure of $R^B$-L-FG2 or a salt thereof. In some embodiments, a composition or system comprises an agent having the structure of $R^P$-L-FG3 or a salt thereof, an agent has the structure of $R^B$-L-FG2 or a salt thereof, and an agent having the structure of $R^C$-L-FG1 or a salt thereof. In some embodiments, a composition or system comprises an agent having the structure of $R^C$-L-$L^P$-L-$R^B$ or a salt thereof, an agent has the structure of $R^B$-L-FG2 or a salt thereof, and an agent having the structure of $R^C$-L-FG1 or a salt thereof. In some embodiments, a composition or system comprises one or more or all of an agent having the structure of $R^C$-L-$L^P$-L-$R^B$ or a salt thereof, an agent has the structure of $R^B$-L-FG2 or a salt thereof, an agent has the structure of $R^P$-L-FG2 or a salt thereof, and an agent having the structure of $R^C$-L-FG1 or a salt thereof. In some embodiments, the present disclosure provide cells comprising such compositions or systems. In some embodiments, the present disclosure provide cell cultures comprising such compositions or systems.

In some embodiments, the invention provides methods and reagents for determining if a candidate compound is able to traverse an animal cell membrane. Such a candidate compound that can traverse an animal cell membrane is a cell penetrating compound.

The published patents, patent applications, websites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

Terms defined or used in the description and the claims shall have the meanings indicated, unless context otherwise requires. Technical and scientific terms used herein have the meaning commonly understood by one of skill in the art to which the present invention pertains, unless otherwise defined. Any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Accordingly, in a first aspect, the invention provides a method for identifying one or more candidate compounds that traverse an animal cell membrane. The method comprises providing phospholipid bilayer comprising a first side and a second side, the first side defining a first region, said first region comprising one or more capture molecules; adding a plurality of distinct candidate compounds, each distinct candidate compound attached to a binding moiety, to a second region defined by the second side of the phospholipid bilayer, under conditions whereby each distinct candidate compound of the plurality traversing the phospholipid bilayer enters the first region and forms a complex with a capture molecule in the first region via a covalent bond between a portion of the binding moiety attached to the distinct candidate compound and the capture molecule, wherein one or more complexes are formed; disrupting the one or more complexes to create one or more distinct candidate compounds each attached to a releasing moiety, said releasing moiety different from the binding moiety; and identifying the one or more distinct candidate compounds attached to the releasing moiety as being one or more candidate compounds that traverses an animal cell membrane. In some embodiments, the identifying step identifies the amino acid sequence of the candidate compound. In some embodiments, the identifying step identifies the structure of the candidate compound.

In another aspect, the invention provides a method for determining if a candidate compound traverses an animal cell membrane, the method comprising providing phospholipid bilayer comprising a first side and a second side, the first side defining a first region, said first region comprising one or more capture molecules; adding the candidate compound attached to a binding moiety to a second region defined by the second side of the phospholipid bilayer, under conditions whereby the candidate compound traversing the phospholipid bilayer enters the first region and forms a complex with a capture molecule in the first region via one or more covalent bonds between a portion of the binding moiety (e.g., a functional group in the binding moiety) attached to the candidate compound and the capture molecule; disrupting the complex to create the candidate compound attached to a releasing moiety, said releasing moiety different from the binding moiety; and identifying the candidate compound attached to the releasing moiety as being a compound that traverses an animal cell membrane. In some embodiments, the identifying step identifies the amino acid sequence of the candidate compound. In some embodiments, the identifying step identifies the structure of the candidate compound.

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001.

As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation (but not aromatic), or combinations thereof. In some embodiments, aliphatic groups contain 1-50 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "alkenyl" refers to an aliphatic group, as defined herein, having one or more double bonds.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, an alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkynyl" refers to an aliphatic group, as defined herein, having one or more triple bonds.

The term "aryl", as used herein, used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term “aryl” may be used interchangeably with the term “aryl ring.” In certain embodiments of the present disclosure, “aryl” refers to an aromatic ring system which includes, but is not limited to, phenyl, biphenyl, naphthyl, binaphthyl, anthracyl and the like, which may bear one or more substituents. Also included within the scope of the term “aryl,” as it is used herein, is a group in which an aromatic ring is fused to one or more non-aromatic rings, such as indanyl, phthalimidyl, naphthimidyl, phenanthridinyl, or tetrahydronaphthyl, and the like.

The term “cycloaliphatic,” “carbocycle,” “carbocyclyl,” “carbocyclic radical,” and “carbocyclic ring,” are used interchangeably, and as used herein, refer to saturated or partially unsaturated, but non-aromatic, cyclic aliphatic monocyclic, bicyclic, or polycyclic ring systems, as described herein, having, unless otherwise specified, from 3 to 30 ring members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, a cycloaliphatic group has 3-6 carbons. In some embodiments, a cycloaliphatic group is saturated and is cycloalkyl. The term “cycloaliphatic” may also include aliphatic rings that are fused to one or more aromatic or nonaromatic rings, such as decahydronaphthyl or tetrahydronaphthyl. In some embodiments, a cycloaliphatic group is bicyclic. In some embodiments, a cycloaliphatic group is tricyclic. In some embodiments, a cycloaliphatic group is polycyclic. In some embodiments, “cycloaliphatic” refers to $C_3$-$C_6$ monocyclic hydrocarbon, or $C_8$-$C_{10}$ bicyclic or polycyclic hydrocarbon, that is completely saturated or that contains one or more units of unsaturation, but which is not aromatic, that has a single point of attachment to the rest of the molecule, or a $C_9$-$C_{16}$ polycyclic hydrocarbon that is completely saturated or that contains one or more units of unsaturation, but which is not aromatic, that has a single point of attachment to the rest of the molecule.

The term “heteroaliphatic”, as used herein, is given its ordinary meaning in the art and refers to aliphatic groups as described herein in which one or more carbon atoms are independently replaced with one or more heteroatoms (e.g., oxygen, nitrogen, sulfur, silicon, phosphorus, and the like). In some embodiments, one or more units selected from C, CH, $CH_2$, and $CH_3$ are independently replaced by one or more heteroatoms (including oxidized and/or substituted forms thereof). In some embodiments, a heteroaliphatic group is heteroalkyl. In some embodiments, a heteroaliphatic group is heteroalkenyl.

The terms “heteroaryl” and “heteroar-”, as used herein, used alone or as part of a larger moiety, e.g., “heteroaralkyl,” or “heteroaralkoxy,” refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 Tn electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms “heteroaryl” and “heteroar-”, as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term “heteroaryl” may be used interchangeably with the terms “heteroaryl ring,” “heteroaryl group,” or “heteroaromatic,” any of which terms include rings that are optionally substituted. The term “heteroaralkyl” refers to an alkyl group substituted by a heteroaryl group, wherein the alkyl and heteroaryl portions independently are optionally substituted.

The term “heteroatom”, as used herein, means an atom that is not carbon or hydrogen. In some embodiments, a heteroatom is boron, oxygen, sulfur, nitrogen, phosphorus, or silicon (including various forms of such atoms, such as oxidized forms (e.g., of nitrogen, sulfur, phosphorus, or silicon), quaternized form of a basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl) etc.). In some embodiments, a heteroatom is oxygen, sulfur or nitrogen.

As used herein, the terms “heterocycle,” “heterocyclyl,” “heterocyclic radical,” and “heterocyclic ring”, as used herein, are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term “nitrogen” includes substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^+NR$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms “heterocycle,” “heterocyclyl,” “heterocyclyl ring,” “heterocyclic group,” “heterocyclic moiety,” and “heterocyclic radical,” are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term “heterocyclylalkyl” refers to an alkyl group substituted by a heterocyclyl, wherein the alkyl and heterocyclyl portions independently are optionally substituted.

As described herein, agents, compounds, and moieties thereof may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. Certain substituents are described below.

Suitable monovalent substituents on a substitutable atom, e.g., a suitable carbon atom, are independently halogen; $-(CH_2)_{0-4}R^{\circ}$; $-(CH_2)_{0-4}OR^{\circ}$; $-O(CH_2)_{0-4}R^{\circ}$, $-O-(CH_2)_{0-4}C(O)OR^{\circ}$; $-(CH_2)_{0-4}CH(OR^{\circ})_2$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH{=}CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)NR^{\circ}_2$; $-N(R^{\circ})C(S)NR^{\circ}_2$; $-(CH_2)_{0-4}N(R^{\circ})C(O)OR^{\circ}$; $-N(R^{\circ})N(R^{\circ})C(O)R^{\circ}$; $-N(R^{\circ})N(R^{\circ})C(O)NR^{\circ}_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}C(O)SR^{\circ}$; $-(CH_2)_{0-4}C(O)OSiR^{\circ}_3$; $-(CH_2)_{0-4}OC(O)R^{\circ}$; $-OC(O)(CH_2)_{0-4}SR^{\circ}$, $-SC(S)SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2NR^{\circ}_2$; $-(CH_2)_{0-4}S(O)R^{\circ}$; $-N(R^{\circ})S(O)_2NR^{\circ}_2$; $-N(R^{\circ})S(O)_2R^{\circ}$; $-N(OR^{\circ})R^{\circ}$; $-C(NH)NR^{\circ}_2$; $-Si(R^{\circ})_3$; $-OSi(R^{\circ})_3$; $-B(R^{\circ})_2$; $-OB(R^{\circ})_2$; $-OB(OR^{\circ})_2$; $-P(R^{\circ})_2$; $-P(OR^{\circ})_2$; $-P(R^{\circ})(OR^{\circ})$; $-OP(R^{\circ})_2$; $-OP(OR^{\circ})_2$; $-OP(R^{\circ})(OR^{\circ})$; $-P(O)(R^{\circ})_2$; $-P(O)(OR^{\circ})_2$; $-OP(O)(R^{\circ})_2$; $-OP(O)(OR^{\circ})_2$; $-OP(O)(OR^{\circ})(SR^{\circ})$; $-SP(O)(R^{\circ})_2$; $-SP(O)(OR^{\circ})_2$; $-N(R^{\circ})P(O)(R^{\circ})_2$; $-N(R^{\circ})P(O)(OR^{\circ})_2$; $-P(R^{\circ})_2[B(R^{\circ})_3]$; $-P(OR^{\circ})_2[B(R^{\circ})_3]$; $-OP(R^{\circ})_2[B(R^{\circ})_3]$; $-OP(OR^{\circ})_2[B(R^{\circ})_3]$; $-(C_{1-4}$ straight or branched alkylene)$O-N(R^{\circ})_2$; or $-(C_{1-4}$ straight or branched alkylene)$C(O)O-N(R^{\circ})_2$, wherein each $R^{\circ}$ may be substituted as defined herein and is independently hydrogen, $C_{1-20}$ aliphatic, $C_{1-20}$ heteroaliphatic having 1-5 heteroatoms independently selected from nitrogen, oxygen, sulfur, silicon and phosphorus, $-CH_2-(C_{6-14}$ aryl), $-O(CH_2)_{0-1}(C_{6-14}$ aryl), $-CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R^{\circ}$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R^{\circ}$ (or the ring formed by taking two independent occurrences of $R^{\circ}$ together with their intervening atoms), are independently halogen, $-(CH_2)_{0-2}R^{\bullet}$, -(halo$R^{\bullet}$), $-(CH_2)_{0-2}OH$, $-(CH_2)_{0-2}OR^{\bullet}$, $-(CH_2)_{0-2}CH(OR^{\bullet})_2$; $-O$(halo$R^{\bullet}$), $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR'_2$, $-NO_2$, $-SiR^{\bullet}_3$, $-OSiR^{\bullet}_3$, $-C(O)SR^{\bullet}$, $-(C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, and a 5-6-membered saturated, partially unsaturated, or aryl ring having 0-4 heteroatoms independently selected from nitrogen, oxygen, and sulfur. Suitable divalent substituents on a saturated carbon atom of $R^{\circ}$ include $=O$ and $=S$.

Suitable divalent substituents, e.g., on a suitable carbon atom, are independently the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, and an unsubstituted 5-6-membered saturated, partially unsaturated, and aryl ring having 0-4 heteroatoms independently selected from nitrogen, oxygen, and sulfur.

Suitable substituents on the aliphatic group of $R^*$ are independently halogen, $-R^{\bullet}$, -(halo$R^{\bullet}$), $-OH$, $-OR^{\bullet}$, $-O$(halo$R^{\bullet}$), $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur.

In some embodiments, suitable substituents on a substitutable nitrogen are independently $-R^{\dagger}$, $-NR^{\dagger}_2$, $-C(O)R^{\dagger}$, $-C(O)OR^{\dagger}$, $-C(O)C(O)R^{\dagger}$, $-C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each $R^{\dagger}$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^{\dagger}$ are independently halogen, $-R^{\bullet}$, -(halo$R^{\bullet}$), $-OH$, $-OR^{\bullet}$, $-O$(halo$R^{\bullet}$), $-CN$, $-C(O)OH$, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, and sulfur.

As used herein, the term “partially unsaturated” refers to a ring moiety that includes at least one double or triple bond. The term “partially unsaturated” is intended to encompass rings having multiple sites of unsaturation, but is not intended to include aryl or heteroaryl moieties, as herein defined.

The term “unsaturated,” as used herein, means that a moiety has one or more units of unsaturation.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present disclosure. Unless otherwise stated, all tautomeric forms of the compounds are within the scope of the present disclosure. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of the present disclosure. Such compounds are useful, for example, as analytical tools, as probes in biological assays, or as therapeutic agents in accordance with the present disclosure.

As used herein, by “candidate compound” is simply meant any type of molecule that is suspected of being able to traverse the cell membrane of an animal cell. The candidate compound may be, without limitation, a small molecule chemical (e.g., having a mass of less than about 900 daltons or less than about 1 nm in size), a larger chemical, an amino acid, a peptide including a synthetic peptide such as a peptide containing one or more synthetic amino acids (e.g., the synthetic amino acid Cba instead of Leucine) and/or made synthetically (e.g., by FMOC solid-phase synthesis or by Boc chemistry synthesis), a stapled or stitched peptide or peptide mimetic, a macrocycle peptide or a peptide mimetic, a protein including proteins having secondary modifications such as glycosylation or palmitoylation, nucleic acids including nucleic acids having secondary modifications such as methylation, lipids, glycolipids, and carbohydrates.

In some embodiments, a peptide can be prepared on a peptide synthesizer. For example, in some embodiments, a peptide candidate compound can be synthesized on an Intavis Multipep RSi peptide synthesizer using Fmoc solid phase peptide chemistry on CEM ProTide Rink Amide resin (loading 0.55-0.8 mmol/g).

In some embodiments, the candidate compound is a stapled or stitched peptide or peptide mimetic. In some embodiments, the candidate compound is a macrocycle peptide or peptide mimetic.

Cyclical, stapled, or stitched peptides or peptide mimetics (or synthetic peptides) are well known. See, for example, any of the compounds described in, e.g., U.S. Pat. Nos. 7,192,713; 8,957,026; 9,617,309; 9,163,330; 9,169,295; 10,081,654; PCT Patent Publication Nos. WO2011/008260; WO2014/052647; WO2014/159969; WO2015/179635; WO2019/051327; and EP Patent Publication Nos. 3559020. In some embodiments, the peptide is made synthetically. In some embodiments, the peptide is made using tert-butyloxycarbonyl (Boc) as a temporary N-terminal α-amino protecting group during peptide synthesis. Briefly, removal of the Boc group with an acid such as trifluoroacetic acid (TFA) allowing the next amino acid to be added to the growing peptide.

In some embodiments, the peptide is made using the fluorenylmethoxycarbonyl protecting group (FMOC) to protect the N-terminus during peptide synthesis (see, e.g., Chan and White, Fmoc Solid Phase Peptide Synthesis—A Practical Approach. Oxford University Press, 2000; PCT Publication No. WO 2019/051327). Briefly, in Fmoc solid-phase peptide synthesis, amino acids are protected at their N terminus by the Fmoc (9-fluorenylmethoxycarbonyl) group and coupled to the growing peptide chain after activation of the carboxylic acid terminus. The Fmoc group is then removed by piperidine treatment and the process repeated. The finished peptide can then be removed from the resin by treatment with trifluoroacetic acid (TFA), and the peptide purified (e.g., using reverse-phase HPLC).

In some embodiments, the candidate compound is attached to a binding moiety. In some embodiments, by “attached” is meant covalently bonded (e.g., the candidate compound is covalently bonded to a binding moiety. By “binding moiety” is meant any molecule that can be attached to a candidate compound where the binding moiety (e.g., a linker or probe), when unattached to a candidate compound, is able to traverse a phospholipid bilayer. In some embodiments, if a binding moiety is attached to a candidate compound, the binding moiety is unable to traverse a phospholipid bilayer if the candidate compound, unattached to the binding moiety, is unable to traverse that phospholipid bilayer. Thus, in some embodiments, a binding moiety does not aid a candidate compound to which the binding moiety is attached in traversing a phospholipid bilayer. In some embodiments, a binding moiety does not inhibit or impede a candidate compound to which the binding moiety is attached from traversing a phospholipid bilayer.

Methods for generating peptides synthetically are well known, as are methods for attaching a linker to the peptide at the N-terminus, C-terminus, or internally. PCT Publication No. WO2019/051327 describes non-limiting methods for generating peptides synthetically.

Figure 2:
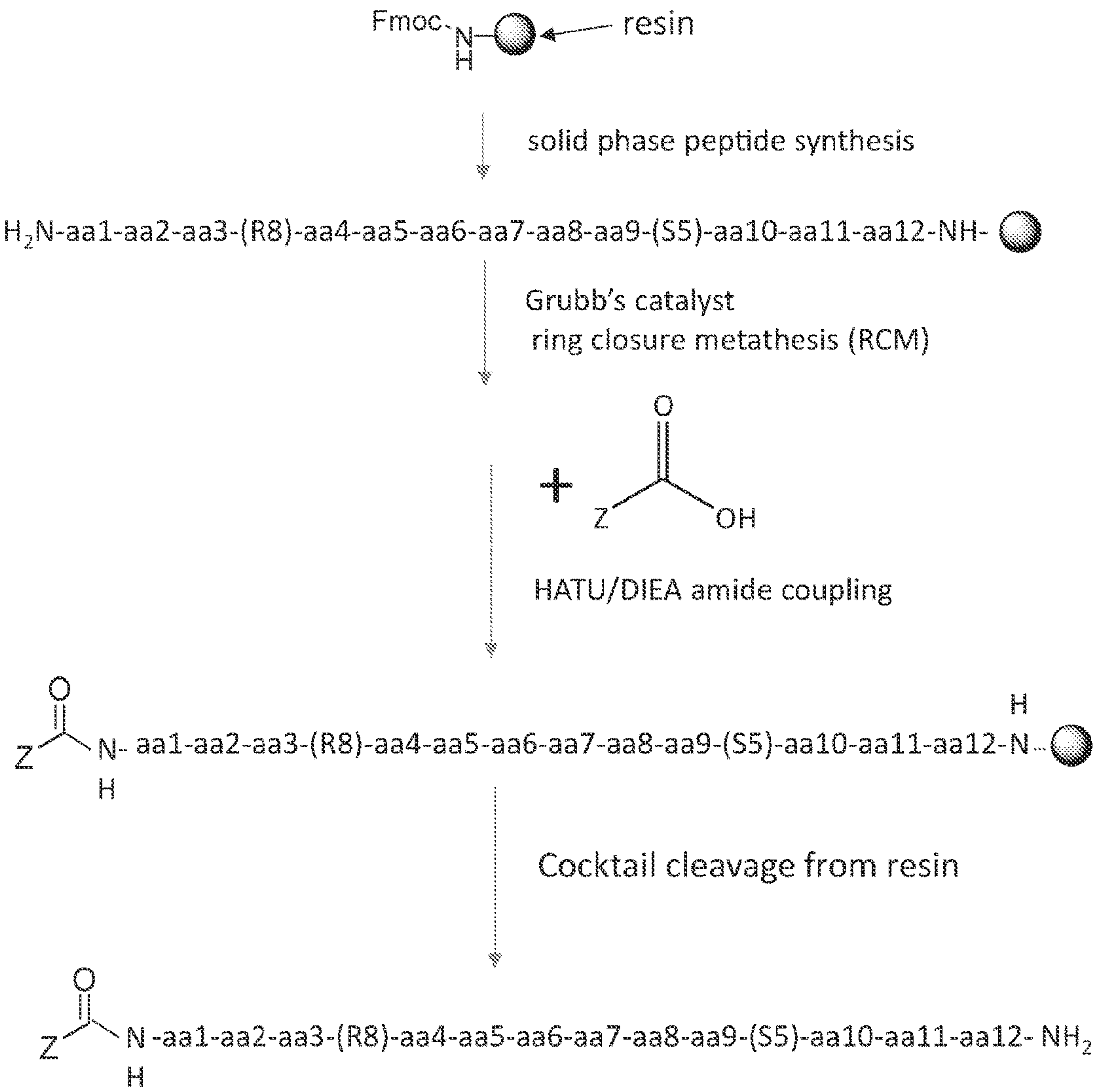
FIG. 2 is a drawing of a schematic showing a non-limiting example of how a non-limiting candidate compound that is a peptide can be generated and attached to a binding moiety.

Without wishing to be bound to a particular theory, FIG. 2 depicts a schematic showing how a non-limiting stapled peptide attached to a binding moiety can be synthesized. As shown in FIG. 2, the peptide is generated with using FMOC solid-phase peptide synthesis according to standard methods. Note the “R8” and “S5” show where the peptide, following synthesis, will be stapled using standard methods such as the Grubb’s catalyst ring closure reaction. For example, for the Grubb’s catalyst reaction, the peptide may be treated with 30 mol % of a freshly prepared 5 mM solution of Bis(tricylcohexhylphosphine)benzylidene ruthenium (IV) dichloride (Grubb’s I) in 1,2-dichloroethane (DCE) for one hour, with vortexing continuously. As shown in FIG. 2, a binding moiety having the structure:

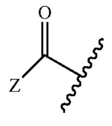

Where Z is, for example,

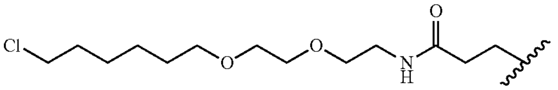

or

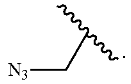

can then be added to the N-terminus of the peptide through standard methods (see, e.g., Dunetz J R et al., “Large-Scale Applications of Amide Coupling Reagents for the Synthesis of Pharmaceuticals”. Organic Process Research & Development. 20 (2): 140-177, 2016) such as the HATU/DIEA amide coupling reaction (where HATU is HATU (1-[Bis (dimethylamino)methylene]—1H-1,2,3-triazolo[4,5-b]pyridinium 3-oxide hexafluorophosphate, Hexafluorophosphate Azabenzotriazole Tetramethyl Uronium) and DIEA is N,N-Diisopropylethylamine, or Hunig’s base.

The binding moiety attached to the peptide covalently bound to the resin is then exposed to a cocktail to cleave the peptide off the resin. The cocktail may contain, for example, trifluoroacetic acid (TFA) to cleave the cocktail. The binding moiety attached to the peptide that is released from the resin is shown at the bottom of FIG. 2.

Figure 3A:
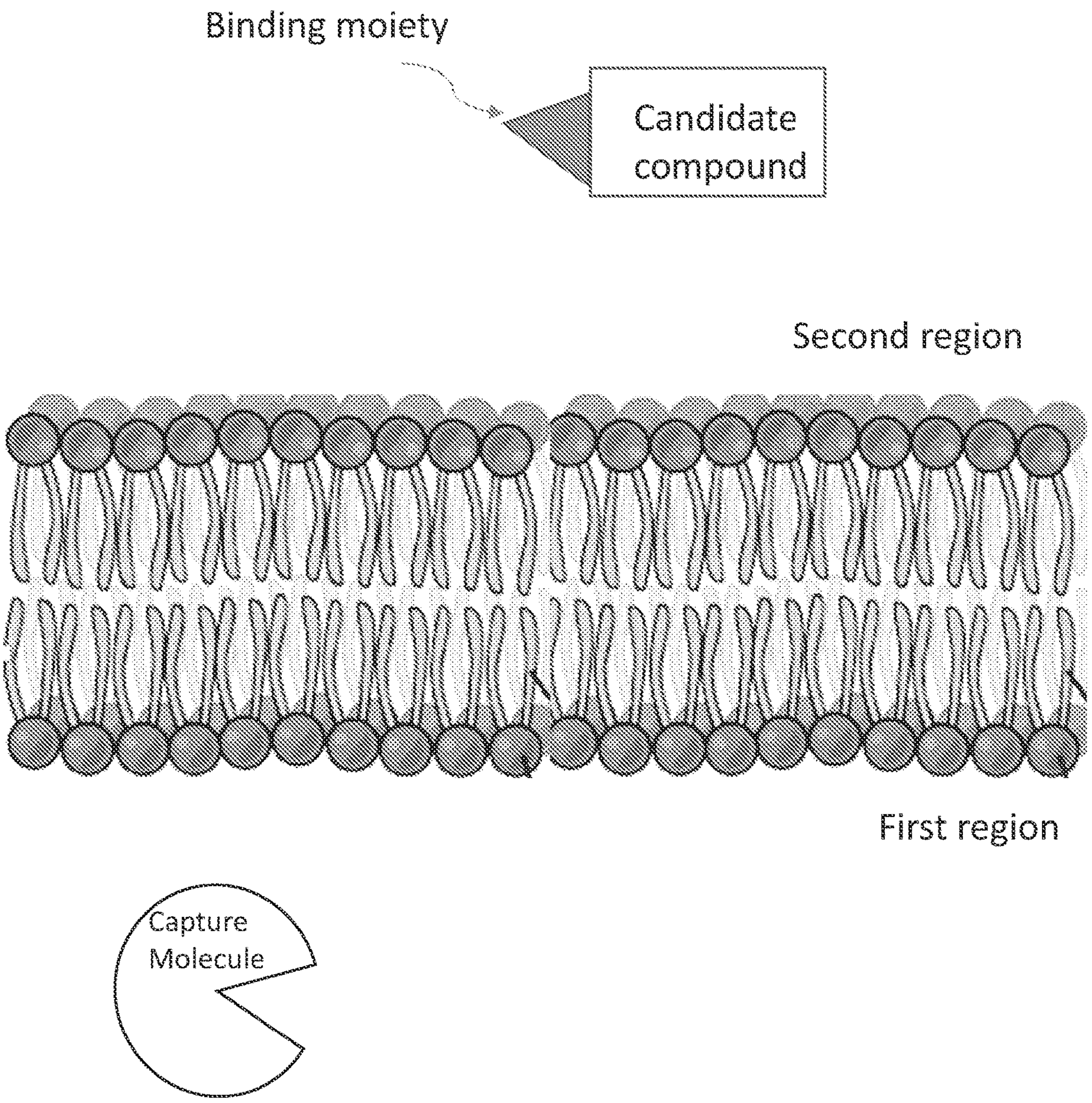
FIGS. 3A-3C are drawings showing a non-limiting embodiment of the invention.
Figure 3B:
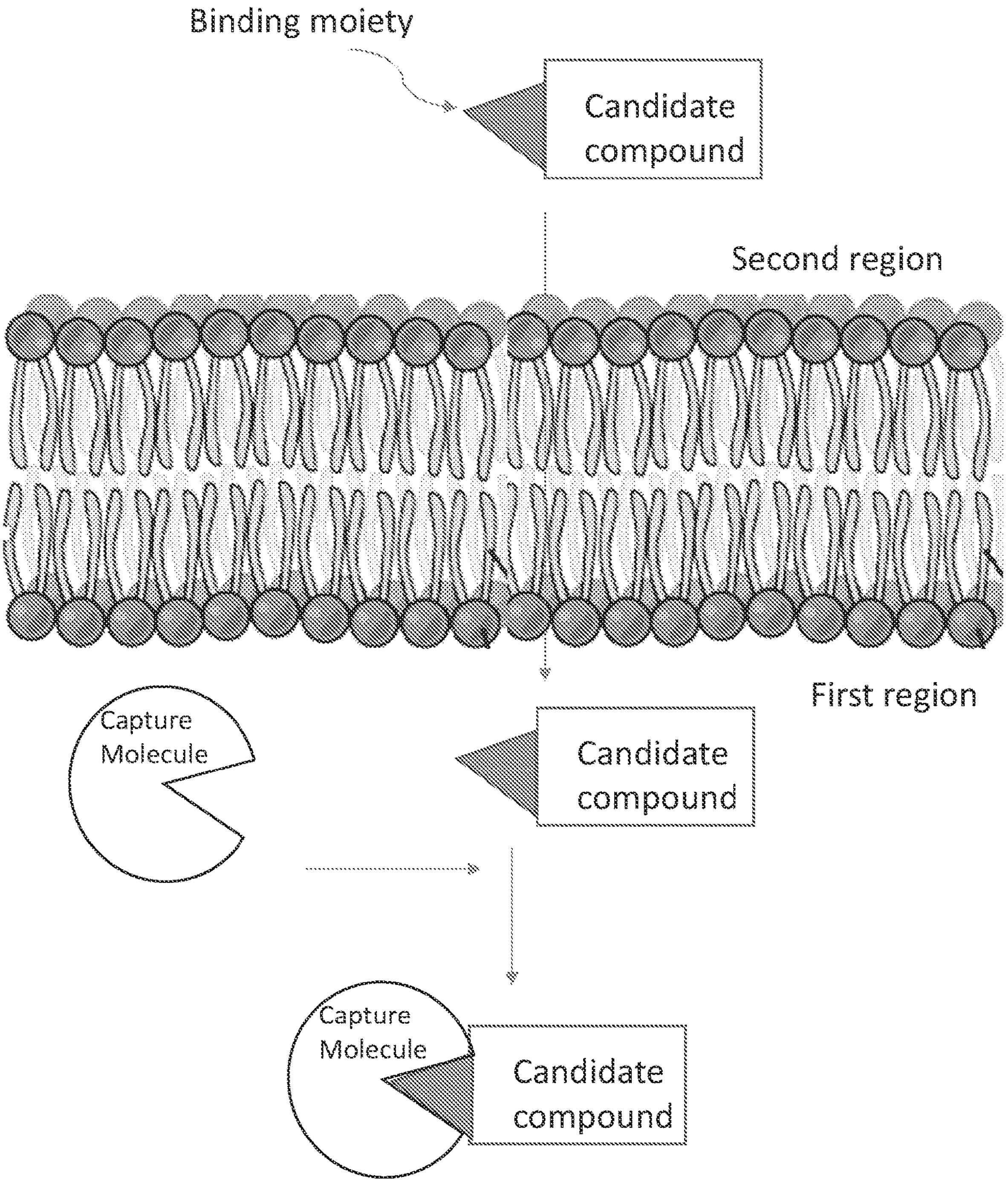
Figure 3C:
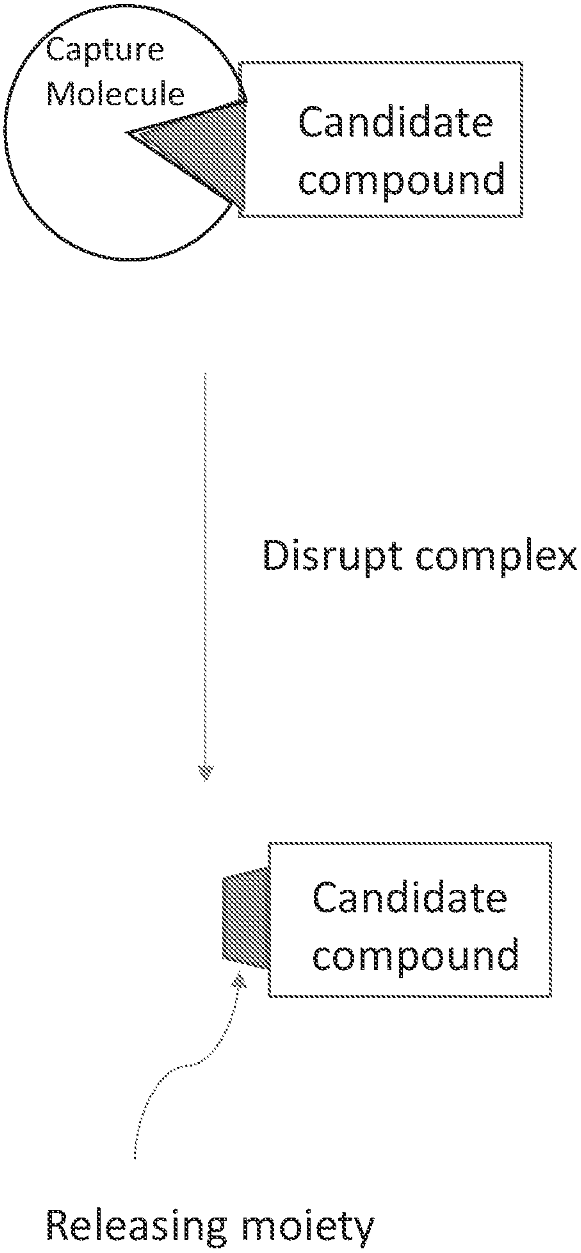

FIGS. 3A-3C schematically depict one embodiment of the invention. As shown in FIG. 3A, a phospholipid bilayer separates a first region from a second region, where the capture molecule is in the first region and a candidate compound attached to a binding moiety is in the second region. As shown in FIG. 3B, if the candidate compound is able to traverse the phospholipid bilayer (and thus move from the second region to the first region), it will covalently bind via the binding moiety attached to the candidate compound with the capture molecule to form a complex in the first region. Finally, as depicted in FIG. 3C, the complex is disrupted freeing the candidate compound that is now attached to a releasing moiety. Since the releasing moiety is different from the binding moiety, the candidate compound attached to the releasing moiety is identified as being a candidate compound that is able to traverse the phospholipid bilayer.

Figure 4A:
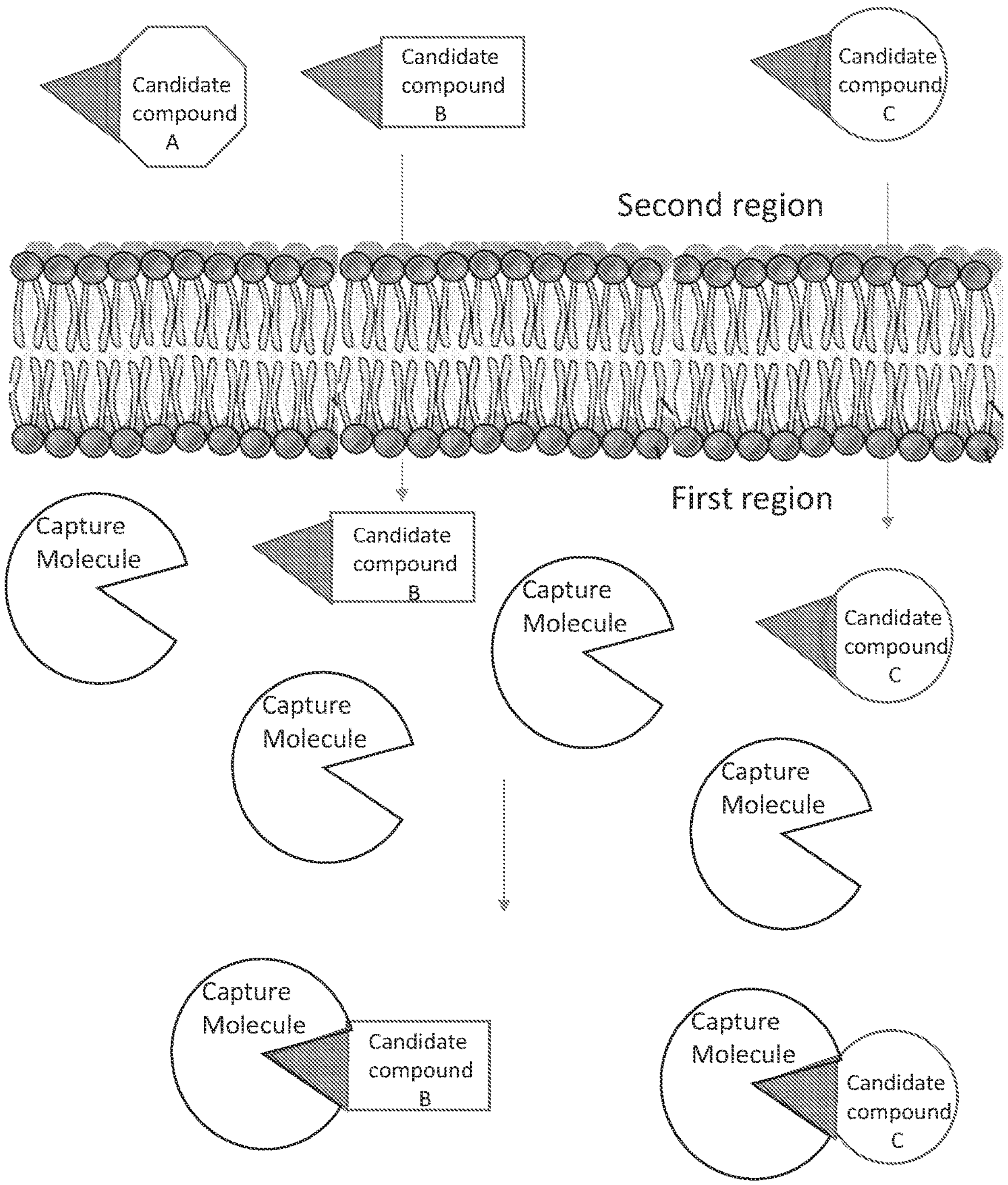
FIGS. 4A and 4B are drawings showing a non-limiting embodiment of the invention, where a phospholipid bilayer separates a first region from a second region, where the first region contains multiple capture molecules and the second region contains a plurality of distinct candidate compounds, each attached to a binding moiety.
Figure 4B:
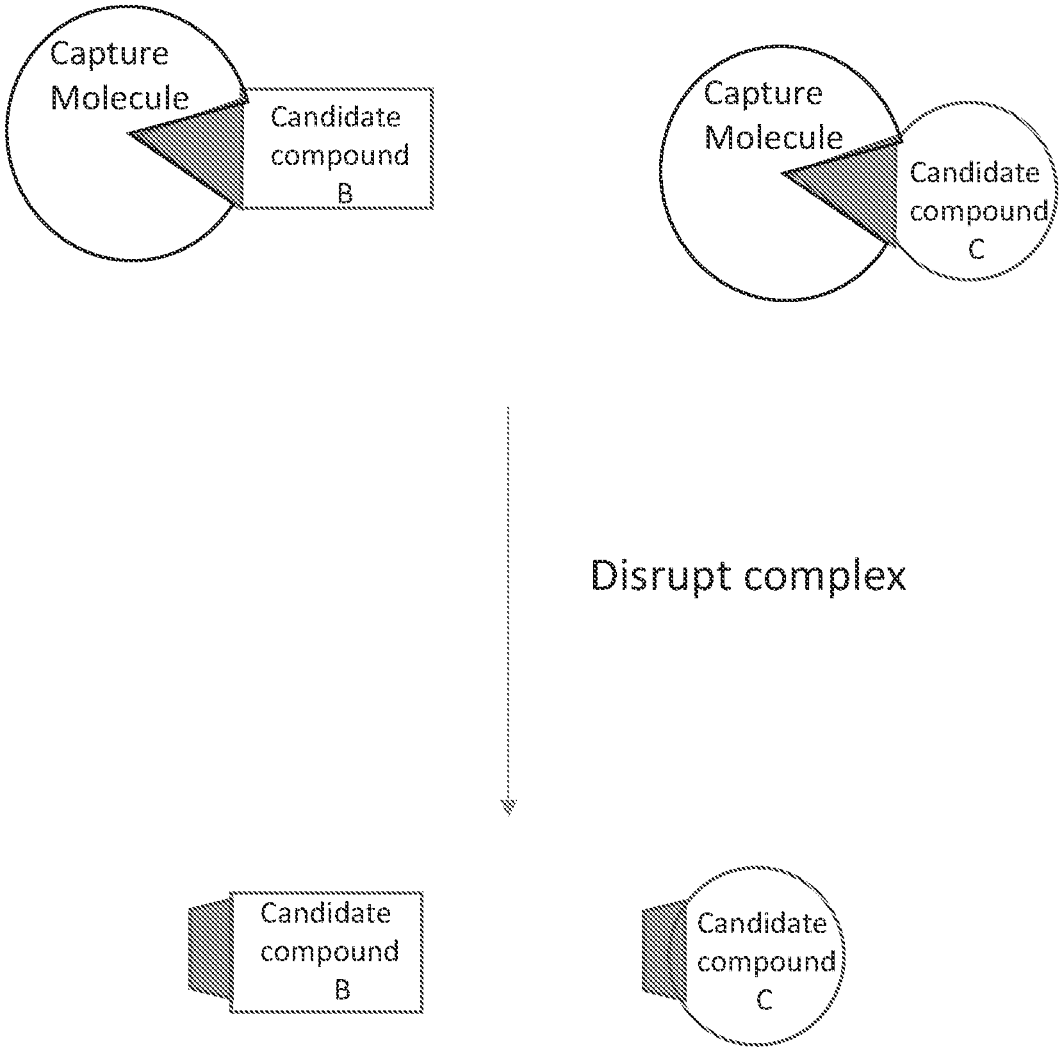

Note that the method depicted schematically in FIGS. 3A-3C is not limited to a single distinct candidate compound. As FIGS. 4A-4B depict, a plurality of distinct candidate compounds can be screened at the same time. As shown in FIG. 4A, a phospholipid bilayer separates a first region from a second region, where the first region contains multiple capture molecules and the second region contains a plurality of distinct candidate compounds, each attached to a binding moiety. Of the three distinct candidate compounds depicted in FIG. 4A, distinct Candidate Compound A does not traverse the phospholipid bilayer while distinct Candidate Compound B and distinct Candidate Compound C do traverse the phospholipid bilayer. At the bottom of FIG. 4A, the binding moiety of Candidate Compound B covalently attaches to a capture molecule and the binding moiety of Candidate Compound C covalently attaches to a capture molecule. As shown in FIG. 4B, disruption of the complexes results in distinct Candidate Compound B attached to the releasing moiety and distinct Candidate Compound C attached to the releasing moiety. In the embodiment shown in this non-limiting FIG. 4A-4B, the releasing moiety is smaller than the binding moiety. By “smaller” is mean smaller in mass, smaller in physical size, or smaller in number of atoms.

Thus, only those candidate compounds that are able to traverse the phospholipid bilayer will form a complex with the capture molecule. Following disruption of the complex, the candidate compounds that traversed the phospholipid bilayer will be those that are attached to a releasing moiety.

It should be noted that when the term “plurality” is describing distinct candidate compounds, such as “a plurality of distinct candidate compounds”, there is more than one distinct candidate compound in the plurality. While there may be one or more copies of the same candidate compound in the plurality, the plurality includes more than one different distinct candidate compounds. In some embodiments, there are at least two different distinct candidate compounds in a plurality of distinct candidate compounds. In some embodiments, there are at least three different distinct candidate compounds in a plurality of distinct candidate compounds. In some embodiments, there are at least five different distinct candidate compounds in a plurality of distinct candidate compounds. In some embodiments, there are at least ten different distinct candidate compounds in a plurality of distinct candidate compounds. In some embodiments, there are at least twenty different distinct candidate compounds in a plurality of distinct candidate compounds. In some embodiments, there are at least fifty distinct candidate compounds in a plurality of distinct candidate compounds. In some embodiments, there are at least one hundred distinct candidate compounds in a plurality of distinct candidate compounds. In some embodiments, there are at least one hundred fifty distinct candidate compounds in a plurality of distinct candidate compounds. In some embodiments, there are at least two hundred distinct candidate compounds in a plurality of distinct candidate compounds. In some embodiments, there are at least two hundred fifty distinct candidate compounds in a plurality of distinct candidate compounds. It will be understood that each distinct molecule may occur once or more than once within the plurality. For example, if a plurality of distinct candidate compounds comprises three distinct candidate compounds, there may be one copy of a first distinct candidate compound, three copies of a second distinct candidate compound, and ten copies of a third distinct candidate compound.

As used herein, by “phospholipid bilayer” is meant a double layer of phospholipids, where the hydrophobic tails face one another and the hydrophilic heads face away from one another (see, e.g., FIG. 1). Note that although a cell membrane comprises a phospholipid bilayer, it is not necessary for a phospholipid bilayer to be in a cell membrane. For example, a phospholipid bilayer may be in a liposome. A phospholipid bilayer also need not be spherical (or roughly spherical), or even circular or oval. For example, a flat phospholipid bilayer is contemplated within various embodiments of the present invention.

Figure 5A:
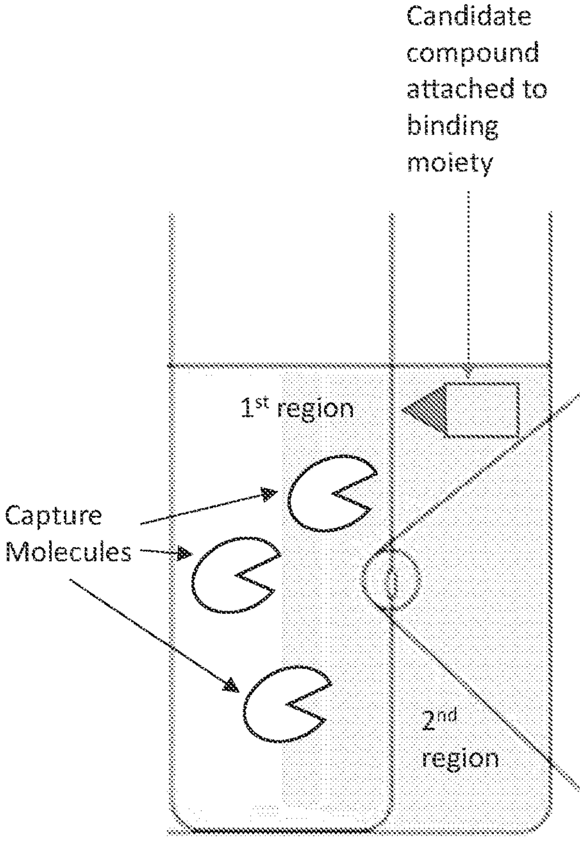
FIGS. 5A and 5B are drawings depicting a non-limiting type of planar phospholipid bilayer that can be used within various embodiments of the invention.
Figure 5B:
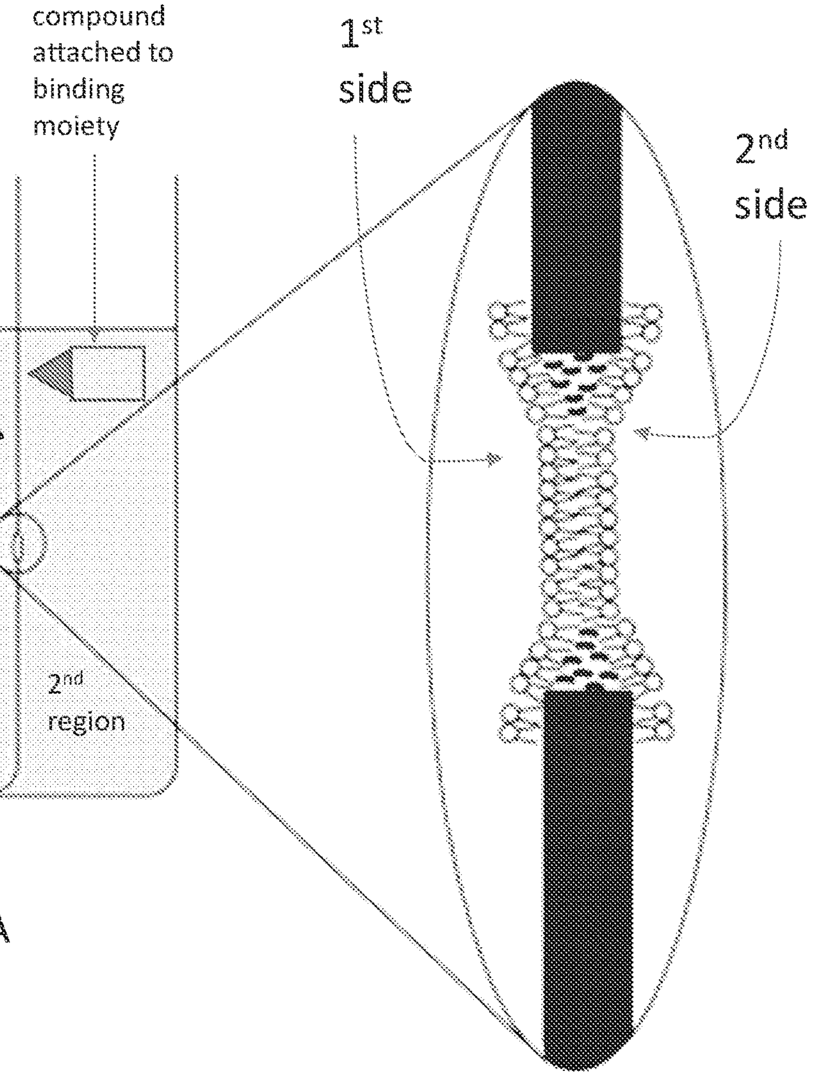

In some embodiments, the phospholipid bilayer is flat or planar. One non-limiting example of a flat phospholipid bilayer may be based on the black lipid membrane (BLM) model (see, e.g., Mueller P. et al., Nature 194 (4832):979-980, 1962; Montal and Mueller, Proc. Natl. Acad. Sci USA 69: 356103566, 1972). These can be formed by standard methods. For example, phospholipids can be dissolved in a hydrocarbon solvent and painted across a small aperture (e.g., 1-5 mm in diameter) which separates a first region from a second region. Once the phospholipid bilayer is formed, one or more capture molecules can be added to a first region and one or more candidate compounds can be added to the second region (see FIG. 5A). FIG. 5B is a blow up of a cross section of the aperture of FIG. 5A showing the phospholipid bilayer spanning the aperture. As shown in FIGS. 5A-5B, the first side of the phospholipid bilayer contacts a first region, said first region containing one or more capture molecules. The second side of the phospholipid bilayer contacts a second region. The candidate compound(s) will be added to the second region and, if the candidate compound is able to traverse the phospholipid bilayer, the binding moiety attached to the candidate compound will covalently bind to the capture molecule forming a complex. The complex can then be disrupted as shown in FIG. 3C to create a candidate compound attached to a releasing moiety.

In some embodiments, the phospholipid bilayer is spherical (or roughly spherical) such that the inside layer of the phospholipid bilayer is contiguous, and the outside layer of the phospholipid bilayer is contiguous. In some embodiments, the spherical (or roughly spherical) phospholipid bilayer completely encloses and defines a first region within the inside layer of the phospholipid bilayer, and the outside layer of the phospholipid bilayer faces a second region that it outside of the phospholipid bilayer.

Figure 6:
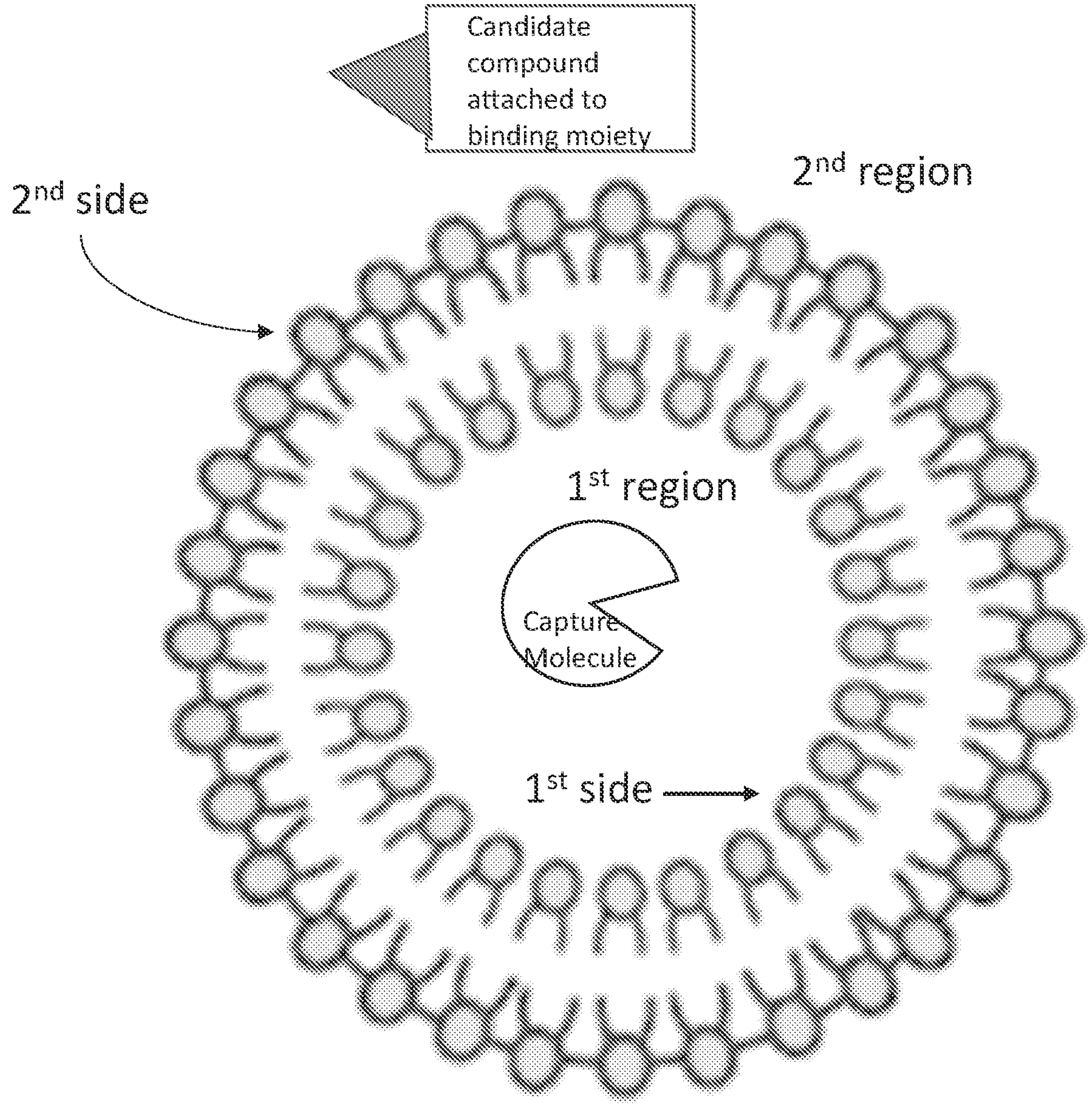
FIG. 6 is a drawing showing a non-limiting embodiment of the invention in which the phospholipid bilayer is spherical and forms a liposome with an internal region (the first region) and an external region (the second region).

In some embodiments, the spherical (or roughly spherical) phospholipid bilayer is the membrane of a liposome. The manufacture of liposomes is well known. See, e.g., Akbarzadeh A. et al., Nanoscale Res. Lett. 8(1): 102, 2013; US Patent Publication No. US20120171280; and U.S. Pat. Nos. 3,932,657, 4,311,712, and 5,013,556. As shown in FIG. 6, liposomes can be manufactured to internally bear one or more capture molecules. In other words, the interior of a liposome is a first region. These capture molecule-containing liposomes can be used in various embodiments of the invention described herein.

In some embodiments, the spherical (or roughly spherical) phospholipid is the cell membrane of a cell (e.g., an animal cell). In some embodiments, the first region within the inside layer of the phospholipid bilayer is the cytosol of the cell, and the second region outside of the outside layer of the phospholipid bilayer is extracellular. If such a cell is in vivo, the components of the extracellular space will differ with the type of cell. For example, if the cell is as sperm cell, the extracellular space may be seminal fluid. If the cell is a blood cell, the extracellular space may be blood plasma or lymphatic fluid. Of course, if the cell is ex vivo, the extracellular space will be whatever the medium is that the cell is being grown or stored in (e.g., tissue culture media, physiological saline, etc.).

In some embodiments, if the phospholipid bilayer is a cell membrane, the cell is an animal cell. In some embodiments, the animal cell is from the same species of animal as the animal cell whose cell membrane is being determined to be traversed by the candidate compound.

As used herein, by "animal cell" is meant a cell of an organism from the kingdom Animalia. In some embodiments, the animal cell is from a vertebrate animal. In some embodiments, the vertebrate animal is a mammal. In some embodiments, the animal is a human, and includes a human of either gender and at any stage of development. In certain embodiments, the animal is a non-human mammal (e.g., a rodent, a mouse, a rat, a rabbit, a monkey, a dog, a cat, a sheep, cattle, a primate, and/or a pig) of either gender and at any stage of development. In some embodiments, an animal includes, without limitation, a mammal, a bird, a reptile, an amphibian, a fish, an insect, and/or a worm. In some embodiments, an animal may be a transgenic animal, genetically engineered animal, and/or a clone.

As used herein, by "cell membrane" or "plasma membrane" is meant a membrane that separates the inside of a cell (the intracellular space) from the outside of the cell (the extracellular space). In some embodiments, a cell membrane comprises a phospholipid bilayer.

In some embodiments, the region defined by the first side of the phospholipid bilayer contains, within the region, one or more capture molecules.

In some embodiments, where the phospholipid bilayer is the cell membrane of a cell (e.g., an animal cell), the capture molecule is made by introducing a nucleic acid (e.g., DNA) encoding the capture molecule into the cell under conditions where the capture molecule is expressed in the cell.

By "introducing" or "introduced" is meant that a nucleic acid is inserted into the cytoplasm of a cell. In some embodiments, the introduced nucleic acid is inserted into the nucleus of the cell. In some embodiments, the introduced nucleic acid is inserted into the cytosol of the cell. Any means for introducing the nucleic acid molecule into the cell can be used including, without limitation, chemical transfection, electroporation transfection, transfusion, infection (e.g., with a recombinant virus), etc. In some embodiments, the nucleic acid encoding the capture molecule is introduced into the cell in a manner whereby the capture molecule is expressed in the cell. Standard methods for introducing a nucleic acid and expressing the introduced nucleic acid are known (see, e.g., *DNA Recombination: Methods and Protocols*, Springer-Verlag New York LLC. (Hideo Tsubouchi), 2011; Current Protocols in Molecule Biology, John Wiley & Sons, Inc. (Ausubel et al.), Dec. 4, 2003)). Additionally, various companies including Promega (Madison, Wisconsin), New England Biolabs (NEB) (Ipswich, MA), and Invitrogen (a Thermo Fisher Scientific company) (Carlsbad, CA) sell reagents and vectors (e.g., expression plasmids) for introducing nucleic acids and expressing them in cells. For example, a nucleic acid encoding a capture molecule can be positioned within a larger nucleic acid molecule (e.g., an expression plasmid), such that the nucleic acid encoding a capture molecule is expressed (e.g., transcribed and/or translated) as protein. In other words, the nucleic acid encoding a capture molecule can be located within a larger nucleic acid molecule along with appropriate regulatory sequences (e.g., promoter, polyA tail, enhancer, etc.) to direct the expression of the capture molecule. In another example, a nucleic acid encoding a capture molecule can be inserted at a particular location within the cell's genome or other DNA or RNA (e.g., mitochondrial DNA) such the inserted nucleic acid encoding a capture molecule is able to benefit from regulatory sequences at the location and thereby express the capture molecule.

Cells appropriate for being introduced with a nucleic acid encoding a capture molecule within the scope of various embodiments described herein include any type of cell, such as a bacterial cell or an animal cell. The American Type Culture Collection (ATCC) (Manassas, VA) sells various different bacterial cells (e.g., *E. coli*) and various different animal cells including, without limitation, cells from insects (e.g., SF9 cells), birds (e.g., Quail Muscle Clone 7 (QM7) cells), dogs (e.g., MDCK cells), frogs (e.g., *Xenopus* A6 cells), fish (e.g., Zebrafish ZF4 cells), hamsters (e.g., CHO cells), humans (e.g., HEK 293 cells), monkeys (e.g., COS cells), and mice (e.g., Py230 cells). Cells can be purchased from various vendors (e.g., Promega; Thermo Fisher Scientific (Waltham, MA), etc.).

In some embodiments, the phospholipid bilayer be spherical and form a liposome. In these embodiments, the one or more capture molecules can be mixed with the phospholipids under condition whereby a liposome will form containing one or more capture molecules in its interior.

In some embodiment, where the phospholipid bilayer is relatively flat, the one or more capture molecules may simply be added to one side of the phospholipid bilayer.

As used herein, by “capture molecule” is meant any molecule that is capable of covalently binding to another molecule to form a complex.

There are numerous capture molecules that are known in the art. A capture molecule may be any type of molecule capable of covalently binding to another molecule to form a complex. Thus, non-limiting types of capture molecules include small chemical molecules, nucleic acids (e.g., DNA, RNA, etc.), amino acids (natural or synthetic), peptides (comprised of natural and/or synthetic amino acids), protein, lipids, sugars and carbohydrates.

In some embodiments, capture molecules are produced and subsequently added to the first region of the phospholipid bilayer. For example, where the phospholipid bilayer is the membrane of a liposome, capture molecules may be mixed with the phospholipid during the formation of the liposomes, such that one or more capture molecules will be encapsulated in the formed liposomes.

In some embodiments, the capture molecule is a protein. In some embodiments, where the phospholipid bilayer is the cell membrane of a cell, the capture molecule is synthesized by the cell itself. For example, if the capture molecule is a protein, the cell may be engineered by standard recombinant methods such that the cell expresses the capture molecule protein in its cytosol.

In some embodiments, the binding moiety is very small compared to the overall size or mass of the candidate compound. For example, the mass of the binding moiety may be less than 33% of the mass of the candidate compound. In some embodiments, the mass of the binding moiety may be less than 25% of the mass of the candidate compound. In some embodiments, the mass of the binding moiety may be less than 20% of the mass of the candidate compound. In some embodiments, the mass of the binding moiety may be less than 10% of the mass of the candidate compound. In some embodiments, the mass of the binding moiety may be less than 5% of the mass of the candidate compound. In some embodiments, the binding moiety does not interfere (either positively or negatively) with the ability of the candidate compound to traverse a phospholipid bilayer.

In some embodiments, the candidate compound is at least two times larger in mass than the binding moiety. In some embodiments, the candidate compound is at least five times larger in mass than the binding moiety. In some embodiments, the candidate compound is at least ten times larger in mass than the binding moiety. In some embodiments, the candidate compound is at least fifteen times larger in mass than the binding moiety.

In one non-limiting example, the modified haloalkane dehalogenase protein sold under the name of HaloTag® by Promega Corp. (Madison, WI) is such a capture molecule. The HaloTag protein is a 34-kDa mutated version of a bacterial dehalogenase (DhaA. K175M/C176G/H272F/Y273L). The HaloTag technology is well known and has been described, for example, in Los et al., ACS Chem Biol. 3(6):73-82, 2008; Urh and Rosenberg, Curr. Chem. Genomics 6: 72-78, 2012; and in U.S. Pat. Nos. 7,112,552; 7,354,750; 7,429,472; and 7,888,086; and PCT Publication No. WO2006093529. The HaloTag® haloalkane dehalogenase protein binds to and forms a covalent bond with molecules that bear a chloroalkane linker. Such a chloroalkane linker (also called a chloroalkane group) may be included in a binding moiety having the following structure:

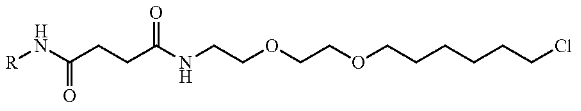

where “R” (in bold font above) is a distinct candidate compound. In accordance with the above, “R” is a candidate compound and

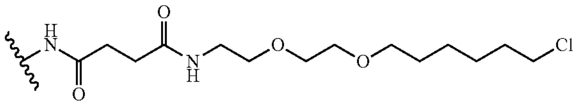 [SMILES: *NC(=O)CCC(=O)NCCOCCOCCCCCCCl]

is the binding moiety attached to the candidate compound.

Of course, it will be understood that other binding moieties comprising a chloroalkane linker can be attached to the HaloTag protein. For example, a binding moiety could have the following non-limiting structure:

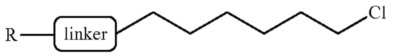

(with R being the candidate compound).

Figure 7A:
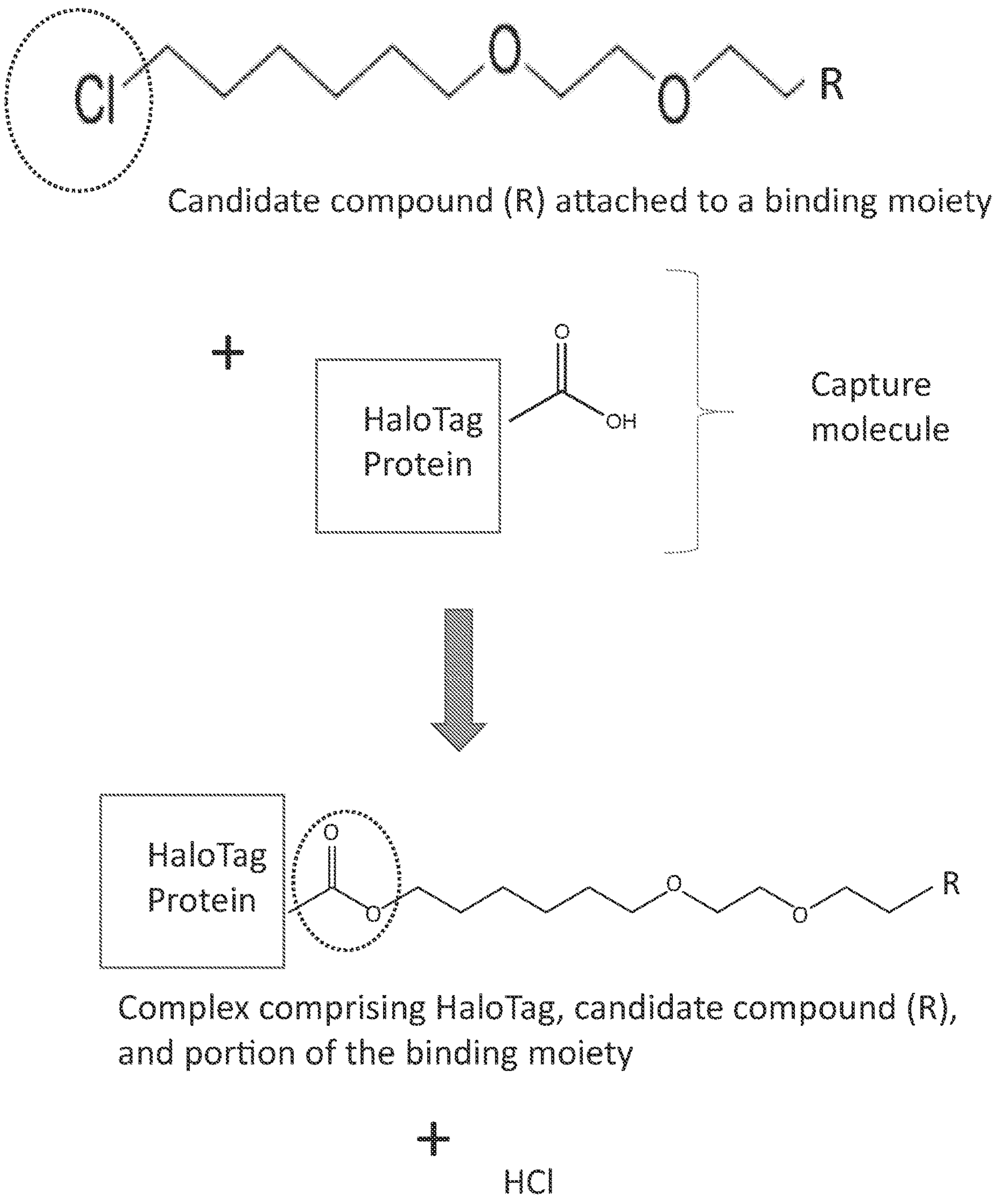
FIGS. 7A-7B are drawings showing a non-limiting embodiment of a binding moiety and capture molecule.

If a candidate compound attached to a binding moiety traverses a phospholipid bilayer, the chloroalkane linker portion of the binding moiety attached to the candidate compound reacts with a carboxyl group on the HaloTag protein to create the complex shown in FIG. 6, where the complex comprises the HaloTag, the candidate compound, and a portion of the binding moiety. As can be seen in FIG. 7A, an irreversible reaction creates the complex, with hydrogen chloride (HCl) being freed from the reaction. As FIG. 7A shows, after complex formation, the Cl atom on the binding moiety is removed (forming HCl which is released) and a ester bond is formed from the carboxyl group on HaloTag protein to create the complex of the HaloTag protein, portion of the binding moiety, and the candidate compound.

Figure 7B:
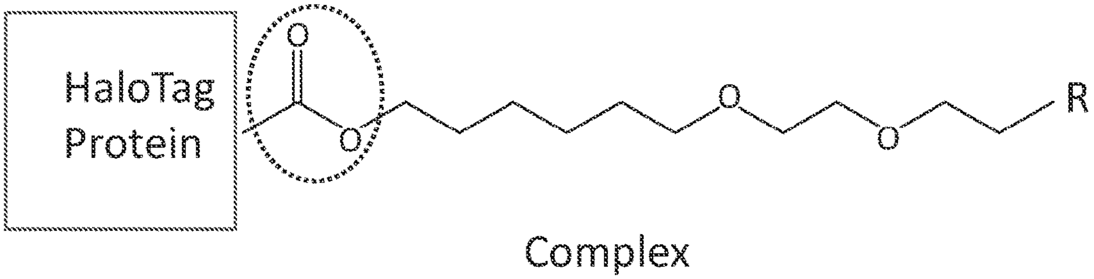
Figure 7B:
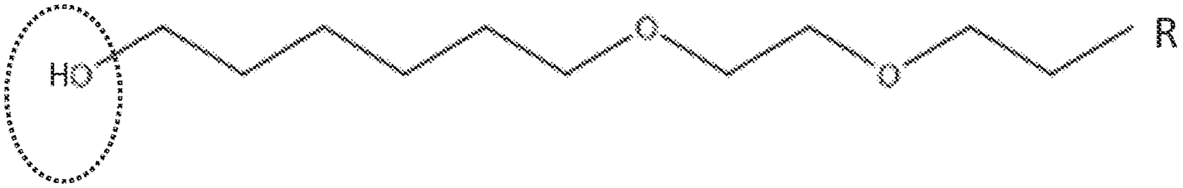

As shown in FIG. 7B, the complex comprising the HaloTag, the candidate compound (R), and portion of the binding moiety can then be disrupted, in accordance with a non-limiting embodiment of the invention, to produce a candidate compound (“R” in FIG. 7B) attached to a releasing moiety. In this case, the complex is disrupted using base hydrolysis by exposing the complex to an environment where the pH is greater than or equal to 11. In some embodiments, the complex is disrupted using base hydrolysis by exposing the complex to an environment where the pH is greater than or equal to 11.5. In some embodiments, the complex is disrupted using base hydrolysis by exposing the complex to an environment where the pH is greater than or equal to 12.0. In some embodiments, the complex is disrupted using base hydrolysis by exposing the complex to an environment where the pH is greater than or equal to 12.5. As shown in FIG. 7B, in one non-limiting embodiment where the capture molecule is a HaloTag protein and the binding moiety includes a chloroalkane linker, the releasing moiety includes a hydroxyl (—OH) group. Because the releasing moiety is different from the binding moiety, any candidate compound attached (e.g., by a covalent bond) to a releasing moiety is identified as a candidate compound that is able to traverse a phospholipid bilayer, such as a phospholipid bilayer serving as the cell membrane of an animal cell.

In some embodiments, the capture molecule comprises a functional group that can form a covalent bond (or more than one covalent bond) with the binding moiety attached to a candidate compound. In some embodiments, the one or more covalent bonds are formed by strain-promoted conjugation. In some embodiments, the one or more covalent bonds are formed by a bioorthogonal chemical reaction.

The binding moiety attached to a candidate compound may contain another functional group that can react with the capture molecule via strain-promoted conjugation. By "strain-promoted conjugation" or "strain-promoted reaction" is meant a chemical reaction that does not require a catalyst or reagent other than the two reacting partners. In some embodiments, the strain-promoted reaction is a bioorthogonal chemical reaction.

Bioorthogonal chemical reactions are those that typically occur inside of a living system (e.g., an animal cell) without interfering with the biochemical processes within the system (e.g., within the animal cell). A number of chemical ligation strategies have been developed that fulfill the requirements of bioorthogonality, including the 1,3-dipolar cycloaddition between azides and cyclooctynes (also termed copper-free click chemistry) (see, e.g., Baskin J M et al., Proc. Natl. Acad. Sci US 104(43): 16793016797, 2007; and U.S. Pat. No. 8,431,558); and between nitrones and cyclooctynes (see, e.g., Ning X. et al., *Angewandte Chemie International Edition.* 49 (17): 3065-3068, 2010, oxime/hydrazone formation from aldehydes and ketones (Yarema K J et al., J. Biol. Chem. 273(47): 31168-31179, 1998), the tetrazine ligation (Blackman et al., J. Amer. Chem. Soc. 130(41): 135-18-13519, 2008), the isocyanide-based click reaction (Stockmann H. et al., Org. & Biomol. Chem. 9(21): 7303, 2011), and the quadricyclane ligation (see, e.g., Sletten E M, et al. J. Amer. Chem. Soc. 133(44): 17570-17573, 2011).

In some embodiments, the use of bioorthogonal chemistry (e.g., a biorthogonal chemical reaction) in various aspects of the invention described herein takes place in multiple steps. In a first step, a substrate (e.g., a HaloTag protein) is introduced into the first region (e.g., the cytosol of an animal cell) creating, for example, a capture molecule. Secondly, a candidate compound attached a binding moiety comprising a functional group complementary to the capture molecule is introduced to the second region. If the candidate compound is able to traverse the phospholipid bilayer and reach the first region, the functional group will react with and bind to the capture molecule to create a complex. Using any type of chemistry (e.g., bioorthogonal or non-bioorthogonal chemistry), the complex is disrupted such that the candidate compound attached to a releasing moiety is created, and any candidate compound attached to a releasing moiety is identified as being able to traverse the phospholipid bilayer.

In some embodiments, the use of biorthogonal chemistry in various aspects of the invention describe herein takes place in three steps. In a first step, a substrate (e.g., a HaloTag protein) is introduced into the first region. Secondly, a small linker (or probe) containing a functional group is introduced into the first region where it reacts with and binds to the substrate to create the capture molecule. In other words, the capture molecule comprises the functional group as well as the substrate. Finally, a candidate compound attached to a binding moiety that comprises a second functional group that is complementary to the functional group of the capture molecule is introduced to the second region. If the candidate compound is able to traverse the phospholipid bilayer and reach the first region, the second functional group on the binding moiety attached to the candidate compound will react with the capture molecule to create a complex. Using any means (e.g., a chemical reaction (e.g., bioorthogonal or non-bioorthogonal chemistry) a change in pH, or physical means), the complex is disrupted such that the candidate compound attached to a releasing moiety is created, and any candidate compound attached to a releasing moiety is identified as being able to traverse the phospholipid bilayer.

By "releasing moiety" is meant any atom or groups of atoms attached (e.g., covalently bonded) to the candidate compound after the complex of the candidate compound, binding moiety (or portion thereof) and capture molecule has been disrupted, where the releasing moiety is different from the binding moiety. In some embodiments, the releasing moiety is smaller in mass than the binding moiety. In some embodiments, the releasing moiety is larger in mass than the binding moiety. In some embodiments, the releasing moiety contains a larger number of atoms than the binding moiety. In some embodiments, the releasing moiety contains a smaller number of atoms than the binding moiety. In some embodiments, the releasing moiety and binding moiety differ by at least one atom.

In various aspects of the invention, a capture molecule may have a functional group that can react with the complementary functional group in the binding moiety attached to the candidate compound intracellularly via strain-promoted conjugation (e.g., a bioorthogonal chemical reaction). In this manner, the capture molecule becomes attached to the candidate compound. One such non-limiting binding moiety is shown as the following structure:

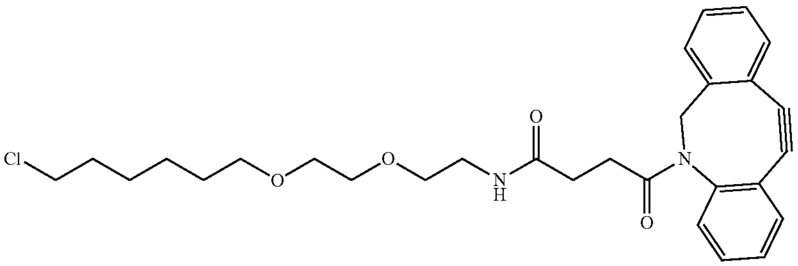 [SMILES: O=C(CCC(=O)N1Cc2ccccc2C#Cc2ccccc21)NCCOCCOCCCCCCCl]

In some embodiments, the capture molecule comprises a linker that can be chemically cleaved. Chemically cleavable linkers are well known in the art (see, e.g., Yang Y., Fonović M., Verhelst S. H. L. (2017) Cleavable Linkers in Chemical Proteomics Applications. In: Overkleeft H., Florea B. (eds)

Activity-Based Proteomics. Methods in Molecular Biology, vol 1491. Humana Press, New York, NY; Stenton B. J., et al., "A thioether-directed palladium cleavable linker for targeted biorthogonal drug decaging," Chemical Science 9: 4185-4189, 2018; Rabalski A J et al., bioRXiv pre-print of doi.org/10.1101/654384, May 2019; Szychowski J. et al., J. Amer. Chem. Soc. 132: 18351-18360, 2010; Yang Y. et al., Molecular & Cellular Proteomics 12: 10.1074/mcp.M112.021014, 237-244, 2013; Verhelst S H et al, Angewandte Chemie Intl Ed. Engl. 46 (8): 1284-1286, 2007; U.S. Pat. No. 8,314,215; US Patent Publication No. 20090181860; PCT Publication No. WO2010014236).

Figure 8A:
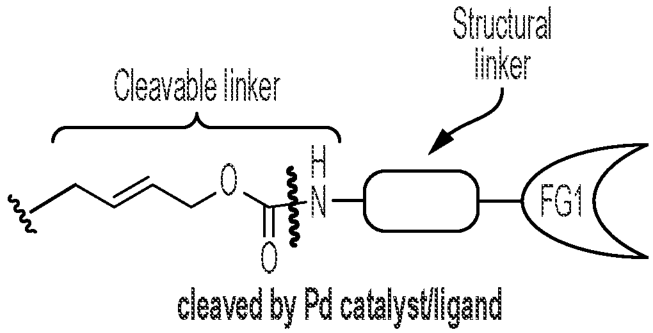
FIG. 8A-8E are drawings of non-limiting examples of chemically cleavable linkers (CCLs) (in addition to or instead of the ester bond depicted in FIGS. 7A-7B), that can be used in the various embodiments of the present invention for disrupting complexes of capture molecules and candidate compounds.

Chemically cleavable linkers include, without limitation, the linkers shown in the non-limiting binding moieties depicted in FIGS. 8A-8E. In FIG. 8A, the cleavable linker in the depicted binding moiety includes a carbamate linkage that can be specifically cleaved by a water-soluble palladium catalyst (e.g., at 1.0 mM Pd-o-DANPHOS catalyst for 30 minutes) (see, e.g., R. Friedman Ohana et al., ACS Chem. Biol., 2016, 11, 2608-2617, 2016; Stenton B. J. et al., supra). For this cleavable linkage, a palladium catalyst (e.g., a phosphine-derived palladium catalyst) will cause a breakage of the carbon-nitrogen bond as indicated in FIG. 8A.

Figure 8B:
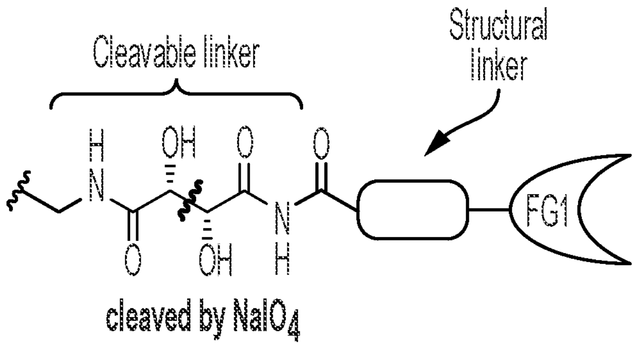

In the cleavable linker depicted in FIG. 8B, cleavage will occur at the site indicated in the figure following exposure to $NaIO_4$ according to standard methods (e.g., 1 mM NaIO4 (50 ul) in sodium phosphate buffer (100 mM sodium phosphate buffer, pH 7.4) for 1 hour). See, also, e.g., Yang Y. et al., Molecular & Cellular Proteomics 12: 10.1074/mcp.M112.021014, 237-244, 2013.

Figure 8C:
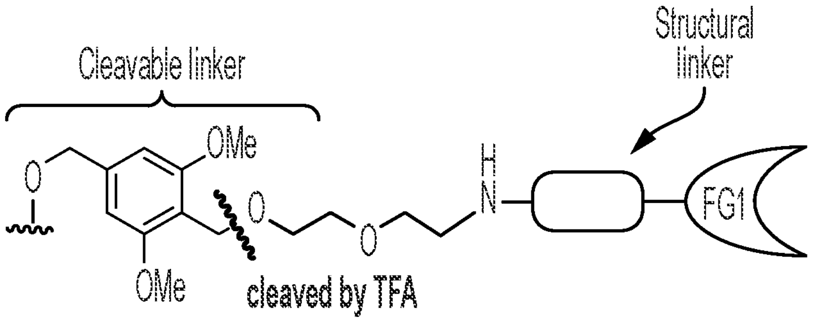
Figure 8D:
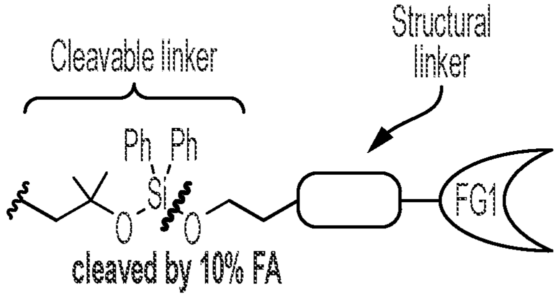
Figure 8E:
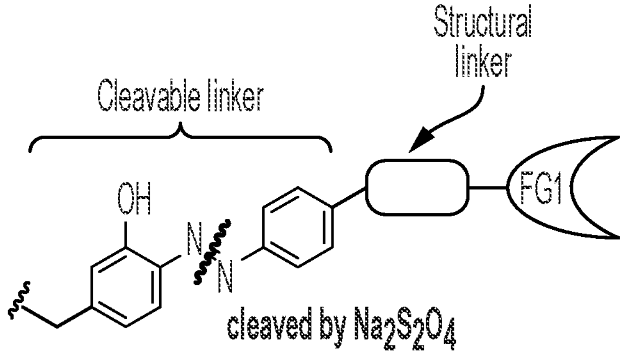

FIGS. 8C, 8D, and 8E show additional non-limiting binding moieties that include non-limiting cleavable linkers. As indicated, the cleavable linker in FIG. 8C will be cleaved at the site indicated by trifluoroacetic acid (TFA), the cleavable linker in FIG. 8D will be cleaved at the site indicated by formic acid (FA) (e.g., at 10%), and the cleavable linker in FIG. 8E will be cleaved at the site indicated by $Na_2S_2O_4$.

In some embodiments, the cleavage of a chemically cleavable linker achieves a reasonable yield of cleavage products. For example, the cleavage yield is at least 70%, or at least 80%, or at least 85%, or at least 90%, or at least 95%. In some embodiments, the conditions for cleavage of a chemically cleavable linker are compatible with a cell-based assay. In some embodiments, the cleavage reaction of a chemically cleavable linker described herein is a bioorthogonal chemical reaction.

In some embodiments where the phospholipid bilayer is the cell membrane of an animal cell, the animal cell stably expresses at least a portion of the capture molecule.

As used herein, by "stably expresses" or "stable expression" is meant that a cell and its progeny express a molecule encoded by an introduced nucleic acid. While it will be understood that some cells and/or their progeny will stop expressing a molecule due to a normal mutation rate, "stable expression" means that the cell and its progeny will continue to express a molecule encoded by an introduced nucleic acid following at least three cell divisions. To achieve stable expression, an introduced nucleic acid may be inserted into the cell's chromosomal or mitochondrial DNA, such that the introduced nucleic acid is replicated when the cell divides, enabling each daughter cell to have a copy of the introduced nucleic acid. An introduced nucleic acid may also result in stable expression of a molecule encoded by the introduced nucleic acid if the introduced nucleic was included when it was introduced, for example, on an episomal plasmid or vector that can replicate even if the plasmid or vector is not integrated into the chromosomal or mitochondrial nucleic acid of the cell. For example, an Epstein Barr virus-based vector may replicate without integrating into a cell's genome if the vector contains an origin of replication that is able to gain access to an EBNA1 protein (e.g., the EBNA1 protein may already be expressed by the cell or may be encoded by the Epstein Barr virus-based vector itself.

In contrast, "transient expression" means that an introduced nucleic acid is introduced into the cell such that the nucleic acid is not integrated into the cell's genome or mitochondrial nucleic acid, or that the introduced nucleic acid was not included in an episomal plasmid or vector. As a result, a cell that transiently expresses a protein encoded by an introduced nucleic acid may itself express that protein, but that expression does not continue for more than seven days in either the cell or its progeny.

In one non-limiting example, the HaloTag protein may be a part of the capture molecule. For example, a cell (e.g., a human cell such as the human colorectal cell line HCT116 commercially available from the ATCC) may be stably transfected with a HaloTag-encoding vector, such as the pHTC HaloTag CMV-neo vector commercially available from Promega. The vector may be linearized (e.g., by cleaving the vector in the ampicillin-encoding region) and introduced (e.g., by lipofectin transfection) into HCT116 cells, and stably transfected cells identified by their ability to grow in G418-containing cell culture media. To complete the capture molecule, any number of small linkers comprising a chloroalkane group and a functional group for strain-promoted conjugation may be added to the cell culture media. As these small linkers will readily traverse the cell membrane, they will enter the cytosol and there will irreversibly react with the HaloTag protein to form a capture molecule.

Figure 9A:
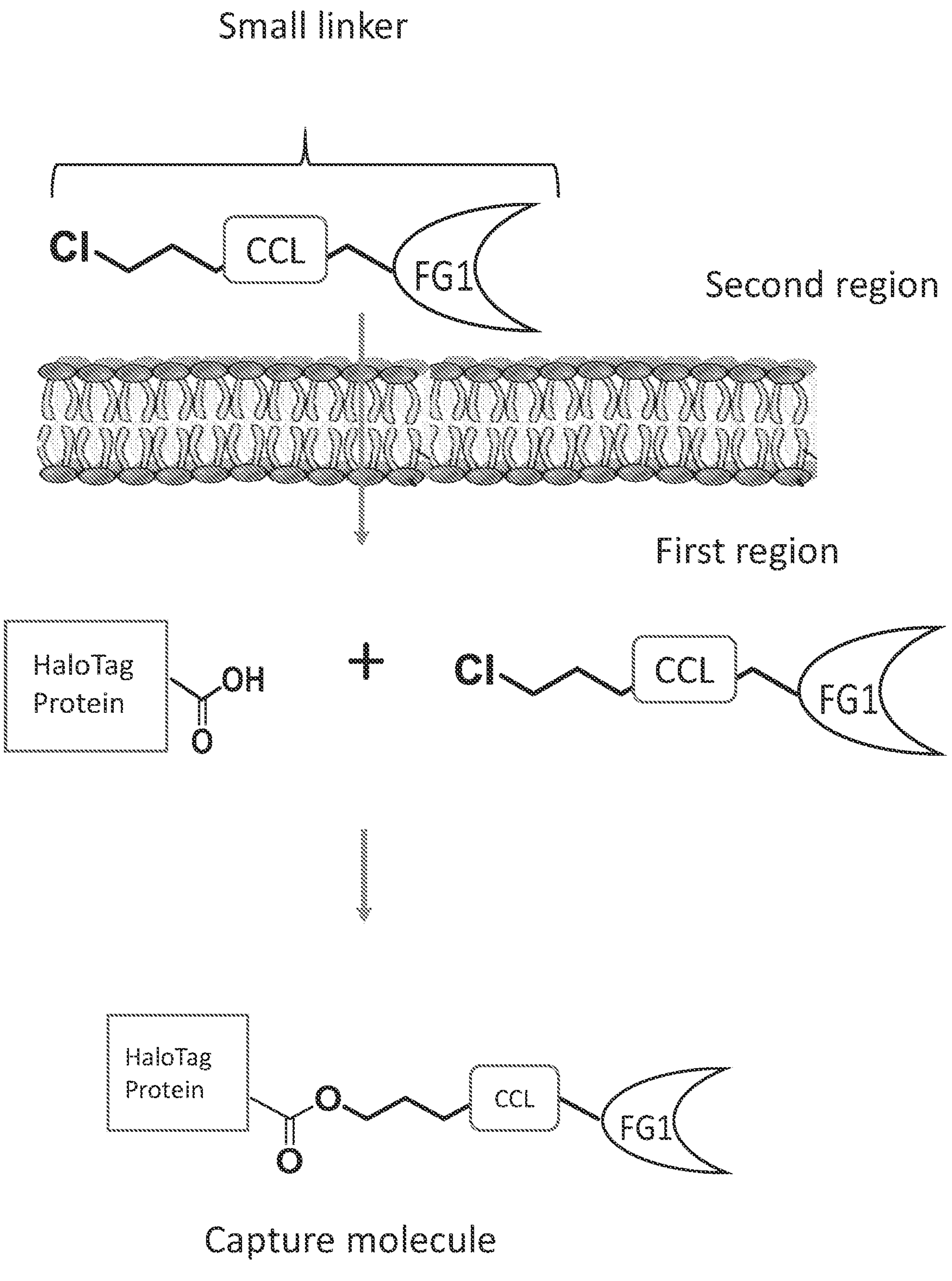
FIGS. 9A-9C are drawings showing a non-limiting embodiment of the invention, where the capture molecule comprises multiple components. The capture molecule is constructed by the covalent attachment of the HaloTag protein in the first region with the small linker containing functional group FG1 in the first region to create a capture molecule (see FIG. 9A). A candidate compound attached to a binding moiety containing functional group FG2 (which is complementary to FG1) that traverses the phospholipid bilayer enters the first region, where the functional group FG2 reacts with the functional group FG1 of the capture molecule to form a complex comprising the capture molecule, the candidate compound, and a product comprising one or more covalent bonds from the reaction of FG1 and FG2 (FIG. 9B). The complex is disrupted by chemically cleaving the CCL to produce the candidate compound attached to a releasing moiety (FIG. 9C).
Figure 9B:
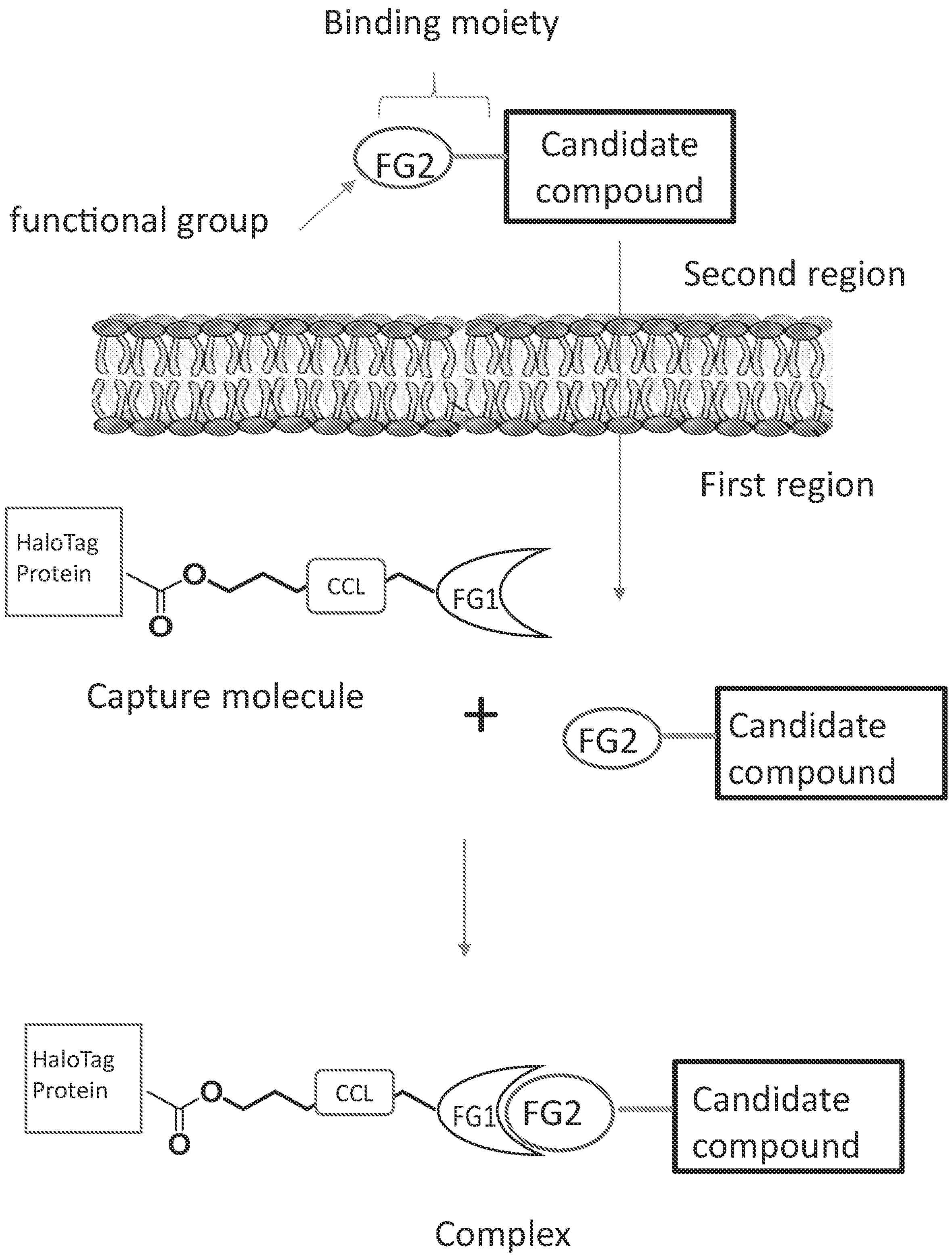
Figure 9C:
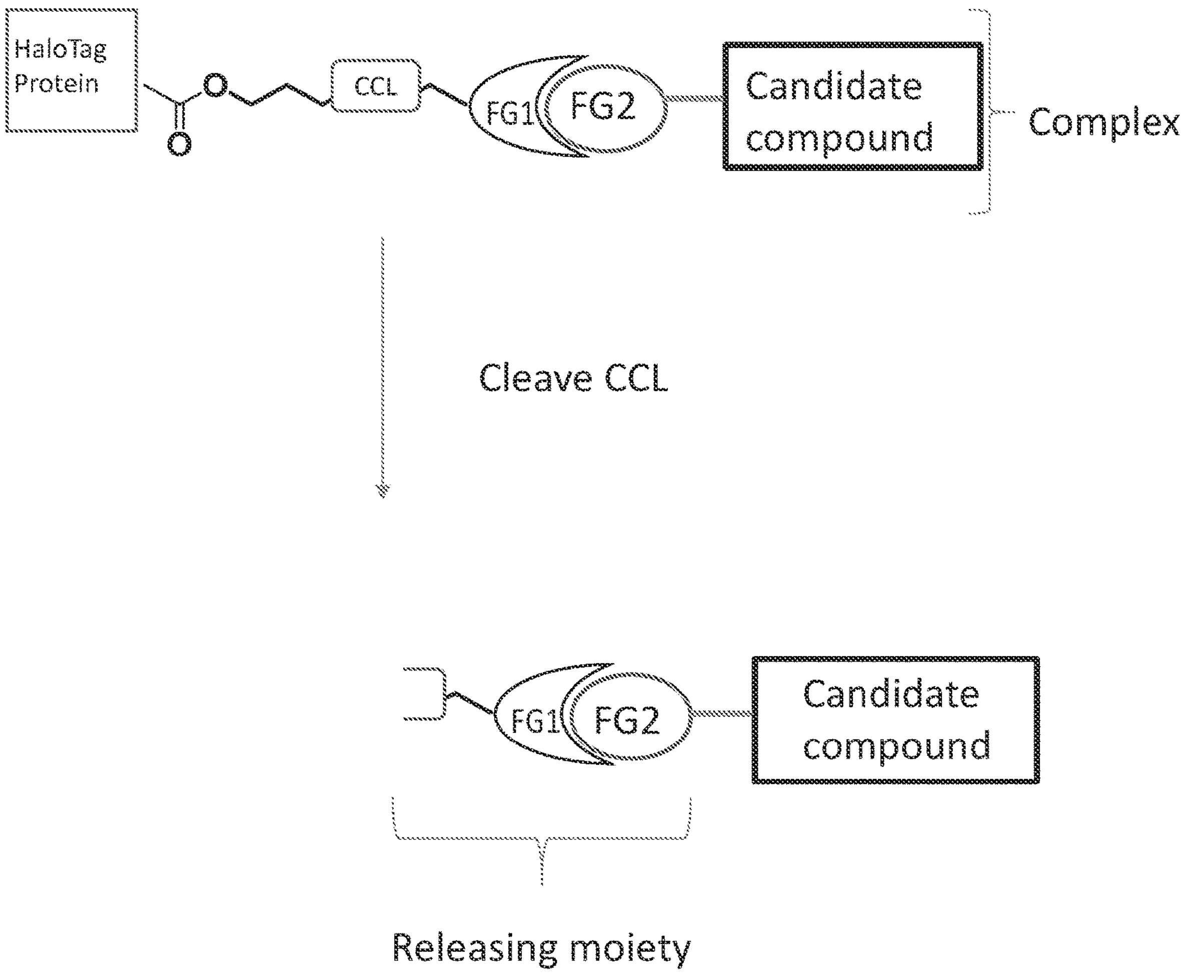

One non-limiting capture molecule comprising multi-components is depicted in FIGS. 9A-9C. In FIG. 9A the components of the capture molecule include a HaloTag protein as a substrate, and a small linker comprising a chemically cleavable inker ("CCL"), a chloroalkane group, and a functional group 1 (FG1). As shown in FIG. 9A, the HaloTag protein is in the first region (e.g., expressed stably or transiently in the cytosol of an animal cell), and the small linker (also referred to as a probe) comprising the chloroalkane group, the CCL group, and the functional group (FG1) is added to the second region (e.g., the culture media in which an animal cell is being cultured). In some embodiments, the small linker is a small molecule (e.g., with a mass of less than about 900 daltons or a size of about 1 nm or less). Being very small, the small linker traverses the phospholipid bilayer and thus enters the first region. In the first region, the small linker covalently binds to the HaloTag protein via the chloroalkane group on the linker to create a multi-component capture molecule, where the components are the HaloTag protein, a group resulting from the reaction of a portion of the binding moiety and the capture molecule (in this FIG. 9A, an ester group created from the reaction of the chloroalkane group and the aspartic acid on the HaloTag protein), the CCL, and the FG1 (see bottom of FIG. 9A). In some embodiments, the number of small linkers added to the second region is smaller than the number of HaloTag proteins in the first region. In some embodiments, there are few, if any, small linkers in the first region that are not coupled to a HaloTag protein. In some embodiments, there fewer than five small linkers in the first region that are not coupled to a HaloTag protein. In some embodiments, there fewer than three small linkers in the first region that are not coupled to a HaloTag protein. In some embodiments, there are no small linkers in the first region that are not coupled to a HaloTag protein.

As shown in FIG. 9B, a candidate compound attached to a binding moiety may then be added to the second region. If the candidate compound attached to a binding moiety is able to traverse the phospholipid bilayer, the binding moiety will react with the capture molecule to form a complex comprising the capture molecule attached to at least a portion of the binding moiety attached to the candidate compound. In FIG. 9C, the complex is disrupted by treating the complex with agent (e.g., formic acid) that cleaves the CCL. As shown at the bottom of FIG. 9C, the newly created candidate compound attached to a releasing moiety is produced. In this non-limiting example, note that the releasing moiety is larger than the binding moiety and thus can be distinguished from the binding moiety. In the embodiment shown in this non-limiting FIG. 9A-9C, the releasing moiety is larger than the binding moiety. By "larger" is mean larger in mass, larger in physical size, or larger in number of atoms. Any candidate compound attached to a releasing moiety is a compound that is able to traverse the phospholipid bilayer and, thus is a compound that is able to traverse the cell membrane of an animal cell.

Figure 10:
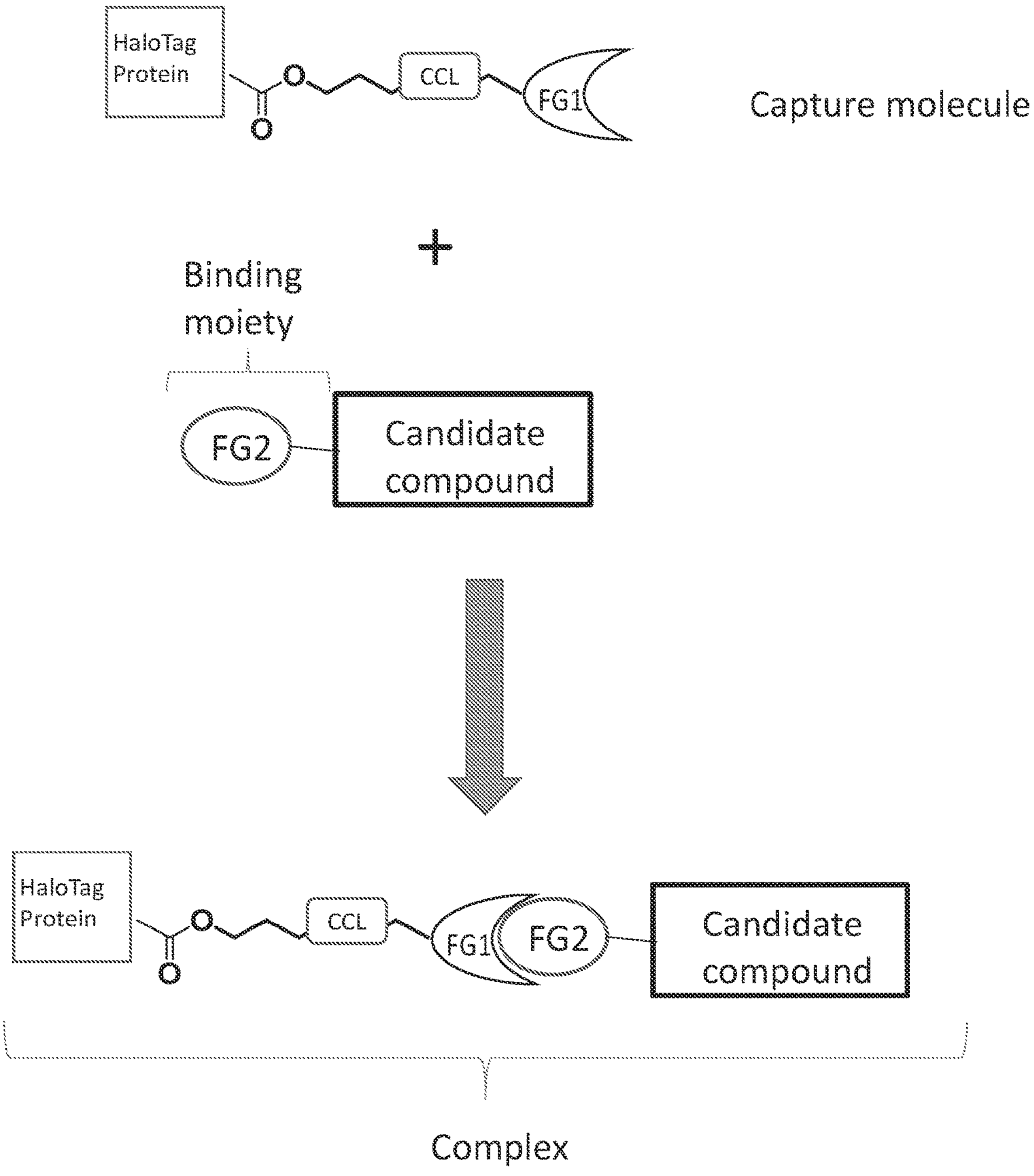
FIG. 10 is a drawing showing a non-limiting embodiment of the invention, where each of the capture molecule and the binding moiety attached to the candidate compound bears a functional group, where the functional groups are complementary to each other.

It will be understood that the entirety of the binding moiety need not react with the functional group FG1 on the capture molecule. Thus, in some embodiments, a portion of the binding moiety reacts with the capture molecule. As shown in FIG. 10, the portion of the binding moiety that reacts with and binds to the capture molecule may be a functional group. See, for example, FIG. 10, where the functional group in the binding moiety is labeled functional group 2 (FG2).

Figure 11:
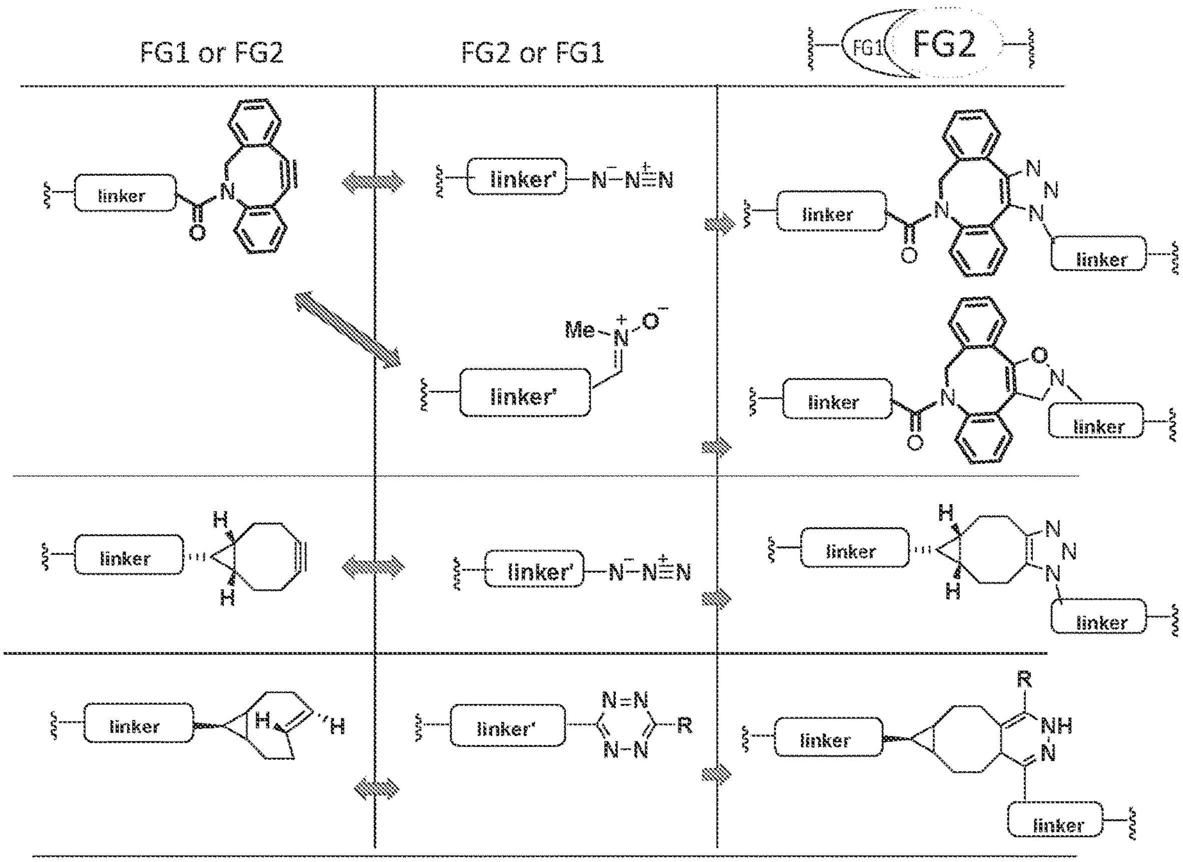
FIG. 11 is a drawing showing some non-limiting functional groups that are complementary to one another and thus can be used as FG1 (as a portion the capture molecule) and/or FG2 (as a portion of the binding moiety attached to the candidate compound) within various embodiments of the invention.

Note that in FIG. 10, FG1 on the capture molecule is complementary to the FG2 on the binding moiety attached to the candidate compound. Note that by "complementary" is meant that two molecules (e.g., functional group, protein, peptide, small molecule, etc.) are able to form one or more covalent bonds with one another and thus be attached to one another. Note that in the attachment of the two complementary molecules, one or more atoms on each of the two molecules may be released. Also note that in the attachment of the two complementary molecules, the one of more covalent bonds joining the two molecules may for a single covalent bond (e.g., an ester bond) or form a cyclical ring (e.g., a heterocyclic group) with more than one covalent bond. A Halo-tag protein is complementary to a chloroalkane group on, for example, a binding moiety. Note that there may be an atom or groups of atoms released during the reaction (e.g., a bioorthogonal reaction) that forms the one or more covalent bonds between two complementary functional groups. It will be understood that in various embodiments of the invention, capture molecules comprising other functional groups can be used together with complementary functional groups on other binding moieties. FIG. 11 shows some non-limiting functional groups that could be used as FG1 (as a portion the capture molecule) and/or FG2 (as a portion of the binding moiety). As shown in FIG. 11, the FG1 and FG2 are interchangeable. Note that in FIG. 11, any of the linkers comprising FG1 or FG2 may further include a chemically cleavable linker.

Furthermore, it will be understood that capture molecules comprising various other components or substrates can be used within the various embodiments of the invention. For example, additional non-limiting examples of components of capture molecules include proteins that form covalent bonds with small molecule linkers, such as the SNAP-tag protein and the CLIP-tag protein sold by New England Biolabs (NEB) (Ipswich, MA), or modifications of these. Both the SNAP-tag protein and the CLIP-tag protein include a free sulfur ion from a cysteine residue.

Figure 12B:
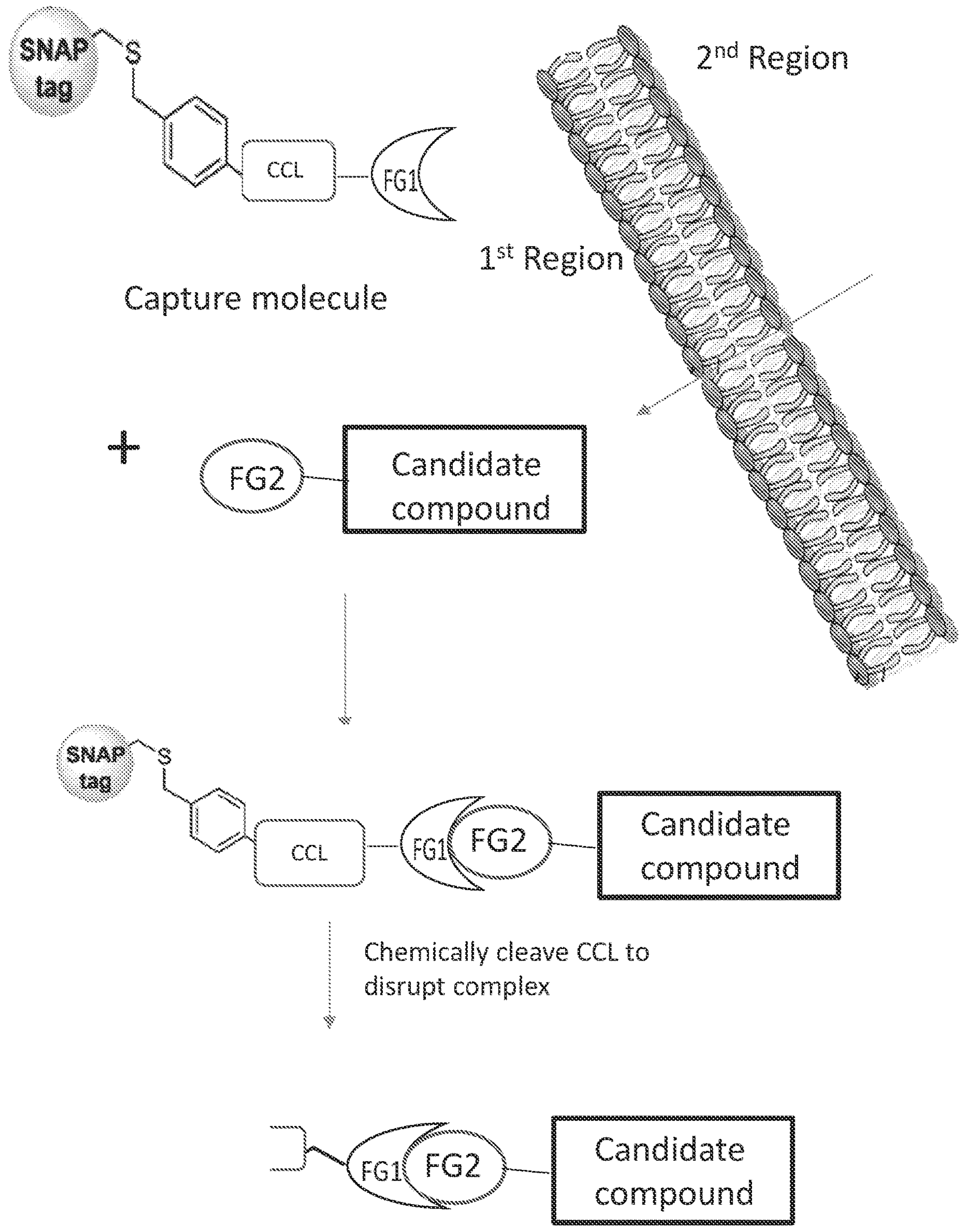

For example, the SNAP-tag protein will form a covalent bond with a benzylguanine derivative through strain-promoted conjugation, where the formation of the covalent bond releases a guanine. In other words, the SNAP-tag protein is complementary to a benzylguanine derivative, such as a benzylguanidine group on, e.g., a small linker. In the non-limiting example shown in FIGS. 12A-12B, a SNAP-tag protein is expressed in the first region and the small linker that includes a functional group (FG1), a chemically cleavable linker (CCL), and a benzylguanidine group is added to the second region. In some embodiments, the small linker is a small molecule (e.g., with a mass of less than about 900 daltons or with a size of less than about 1 nm). Being very small, the small linker traverses the phospholipid bilayer and enters the first region where it covalently bonds via the benzylguanidine group to the SNAP-tag protein, forming the capture molecule and freeing guanine (see bottom of FIG. 12A). As shown in FIG. 12B, a candidate compound attached to a binding moiety (where the binding moiety includes a second functional group (FG2)) is added to the second region. If the candidate compound is able to traverse the phospholipid bilayer, it will enter the first region and covalently bond to the capture molecule via the FG2 group binding to the FG1 group, since FG1 and FG2 are complementary. The resulting complex is then chemically cleaved with the appropriate agent for that CCL (e.g., NaIO4 for the CCL depicted in FIG. 8B) to create a candidate compound attached to a releasing moiety (see bottom of FIG. 12B). Note that in this non-limiting example, the releasing moiety is larger than the binding moiety.

Figure 13:
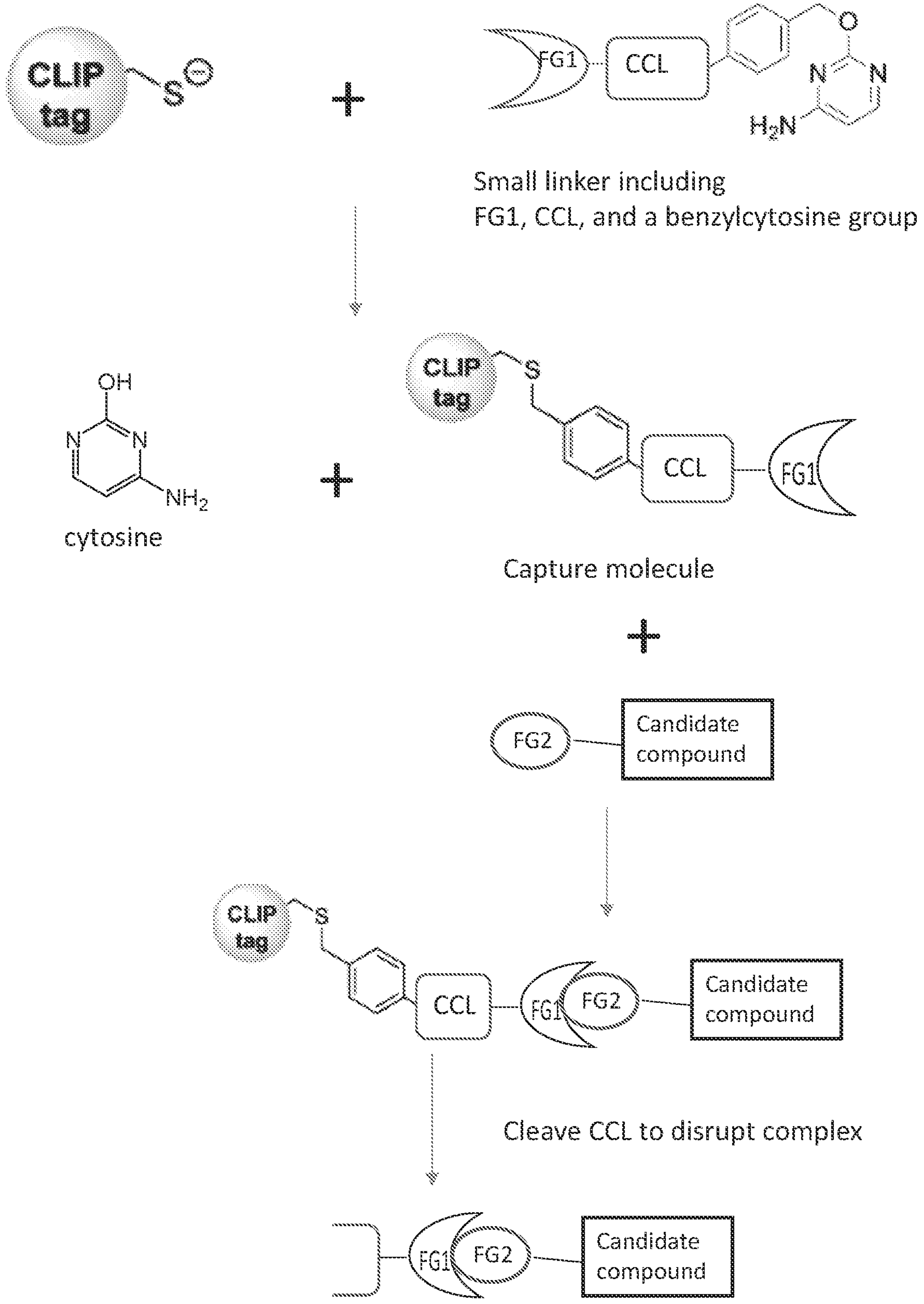
FIG. 13 is a drawing showing a non-limiting embodiment of the invention where the capture molecule includes a modification of a CLIP-tag protein. A capture molecule is created by covalent binding of a CLIP-tag protein to small linker (e.g., a small molecule linker) that includes a functional group (FG1), a chemically cleavable linker (CCL), and a benzylcytosine group (thereby releasing a cytosine molecule). A complex can then be created by covalent binding of the capture molecule to a candidate compound attached to a binding moiety that includes a second functional group (FG2) that is complementary to FG1. Disruption of the complex by cleaving the CCL creates a candidate compound attached to a releasing moiety.

Yet another non-limiting component of a capture molecule is a modification of the CLIP-tag protein. The CLIP-tag protein is complementary to, and thus forms a covalent bond with, a $O_2$-benzylcytosine (BC) derivative, such as the benzylcytosine group on the small linker in FIG. 13. As shown in FIG. 13, a capture molecule can be created (e.g., in the first region) by allowing a CLIP-tag protein to covalently bind to a small molecule linker that includes a functional group (FG1), a chemically cleavable linker (CCL), and a benzylcytosine group, where the reaction creating the capture molecule will release a cytosine. If present (e.g., in a first region), a candidate compound attached to a binding moiety that includes a second functional group (FG2) that is complementary to FG1 will covalently bond to the capture molecule to create a complex. Disruption of the complex by chemically cleaving the CCL with the appropriate agent (e.g., TFA for the CCL depicted in FIG. 8C) will result in a candidate compound attached to a releasing moiety (see bottom of FIG. 13).

As is well known, there are various other capture molecules with various other binding moieties can be used in various embodiments of the present invention. For example, the small molecule penicillin will covalently attach to the active site of D-alanine carboxypeptidase to form an ester bond. Thus, yet another non-limiting capture molecule may be D-alanine carboxypeptidase, and a binding moiety may be penicillin or a derivative thereof that retains the site that binds to D-alanine carboxypeptidase. Other examples include asprin, omeprazole, clopidogrel, neratinib, afatinib, carfilzomib, ibrutinib, or other small molecules which have been reported to form small molecule+protein pairs, in many cases, covalently. Such compounds may be utilized for connecting a functional group and optionally a linker to an agent, e.g., a cellular protein, in a region that an agent to be assessed to is to cross a barrier to reach. In some embodiments, such compounds are useful as $R^F$ moieties. If the candidate compound is able to traverse a phospholipid bilayer to access the region containing the capture molecule, the complex formed containing the ester bond could be disrupted by base hydrolysis, freeing the candidate compound attached to a releasing moiety which would be different from the binding moiety and thus the candidate compound would be identifiable as a compound that is able to traverse an animal cell membrane.

Candidate compounds that are able to traverse the phospholipid bilayer (and thus able to traverse an animal cell membrane) are distinguishable because they are attached to a releasing moiety instead of a binding moiety. In other words, there is no need to obtain the structure of the one or more candidate compounds attached to the binding moiety. Rather, candidate compounds that are attached to a releasing moiety can be identified and analyzed to determine their structure. In this way, properties of compounds capable of traversing a phospholipid bilayer can be determined. Such properties include, of course, whether or not the compound specifically binds to a particular target (e.g., b-catenin) and whether or not the specific binding of the compound to its target has any effect on the target and/or on an animal cell expressing the target.

Methods for identifying candidate compounds are known. For example, if the candidate compound comprises amino acids (e.g., a peptide, a stapled peptide, a synthetic peptide, a protein, etc.), methods for determining the amino acid sequence are well known. See, e.g., U.S. Pat. Nos. 5,240,859; 5,665,037; ,863,870; EP Patent No. EP0257735; Edman and Begg, Eur. J. Biochem. 1 (1):80-91, 1967; and PCT Publication Nos. WO2012178023 and WO2016069124A1.

In a non-limiting method to identify a candidate compound attached to a releasing moiety, mass spectrometry can be used. In another embodiment, liquid chromatography-mass spectrometry (LC-MS) is used to identify a candidate compound attached to a releasing moiety. The released compounds (i.e., candidate compounds attached to a releasing moiety) are identified and quantified by liquid chromatography-mass spectrometry (LC-MS). The compounds are separated by LC, and then introduced into the mass spectrometer. High-resolution mass spectra of the intact compounds are collected for identification and quantification. The compounds are further assessed by MS/MS or $MS^n$ in the mass spectrometer via gas phase dissociation of the intact species into smaller product ions, which are then used to sequence the compounds and validate identifications. For peptide sequencing, b- and y-type product ions are generated containing the N-terminus and C-terminus, respectively. Intact MS and fragmentation $MS^n$ spectra are then used to search against theoretical databases of known compounds to identify and quantify the released compounds. In some cases, the spectra can be de novo sequenced directly from the spectra with no need for a compound database.

In another non-limiting method to identify a compound attached to a releasing moiety, where the candidate compound is a peptide, Edman degradation can be used. For example, Edman degradation can be performed on a protein sequenator. See, e.g., Edman and Begg, Eur. J. of Biochem. 1(1): 80-91, 1967. Protein sequenators (or protein sequencers) are widely commercially available. For example, the PPOSQ-51A protein sequencer is commercially available from Shimadzu Corp., Kyoto, Japan.

In various embodiments, the methods described herein can be used at various stages in the efforts to identify agents that can (a) specifically bind to and/or modulate an intracellular target and (b) traverse the cell membrane to gain access to the cytosol. For example, in some embodiments, various candidate compounds can be screened to find one or more that specifically bind to and/or modulate a desired intracellular target molecule. This screening may be done, for example, without the use of whole cells. For example, immunoprecipitation assays using cell lysates or 3-D modeling may be used. Once such a molecule that specifically binds to and/or modulates an intracellular target is identified, the molecule may then be screened to determine if the molecule is able to traverse the cell membrane using, for example, the methods described herein.

In some embodiments, the invention provides a method for determining if a candidate compound can traverse the cell membrane, and then determining whether that candidate compound can specifically bind to and/or modulate an intracellular target. For example, an initial series of molecules (e.g., a series of small molecule chemicals, peptides, stapled peptides, etc.) may be generated that may or may not bind to any intracellular target molecule with any degrees of affinity. Those molecules may then be first screened to determine if they can cross a cell membrane using, for example, the methods and reagents described herein. Those molecules that are identified as being able to cross a cell membrane can then be screened for the ability to specifically bind to and/or modulate an intracellular target molecule.

As used herein, by “specifically bind” is meant that a molecule (e.g., a compound or an agent) is able to bind to an intended target (e.g., an intracellular molecule) with high affinity. In some embodiments, a molecule that specifically binds to its target binds with an affinity ($K_D$) of not more than 500 uM. In some embodiments, a molecule that specifically binds to its target binds with an affinity ($K_D$) of not more than 50 uM. In some embodiments, a molecule that specifically binds to its target binds with an affinity ($K_D$) of not more than 5 uM. In some embodiments, a molecule that specifically binds to its target binds with an affinity ($K_D$) of not more than 500 nM. In some embodiments, a molecule that specifically binds to its target binds with an affinity ($K_D$) of not more than 50 nM. In some embodiments, a molecule that specifically binds to its target binds with an affinity ($K_D$) of not more than 5 nM.

As used herein, by “modulate” is meant that a molecule (e.g., a compound or agent) is changes the gene expression and/or activity of the intracellular molecule that it is modulating. For example, a molecule may modulate the intracellular molecule by inhibiting the activity and/or expression of the intracellular molecule or by increasing the activity and/or expression of the molecule. In some embodiments, the candidate compound increases the activity and/or expression of an intracellular molecule. In some embodiments, the candidate compound increases the activity and/or expression of an intracellular molecule.

As used herein, by “intracellular target molecule” or “intracellular target” is meant any type of molecule that in located partially or entirely within the cytosol of an animal cell. The intracellular molecule can be free-floating in the cytosol, attached to the inside surface of the cell membrane, and/or attached to the surface of an organelle (e.g., attached to the nuclear membrane or the surface of an organelle). Thus, the intracellular portion of a transmembrane molecule (e.g., receptor tyrosine kinases such a VEGFR-1) is a non-limiting intracellular target molecule as the term is used herein. The intracellular molecule can also be covalently or non-covalently bound to another molecule. The intracellular molecule may be any type of molecule including a protein, a peptide, a nucleic acid molecule, a lipid, a sugar, etc. The intracellular molecule can be a modification of any type of protein (e.g., an intracellular molecule may be a methylated nucleic acid molecule or a glycoprotein).

In another aspect, the invention provides a kit for identifying whether a candidate compound traverses an animal cell membrane comprising a phospholipid bilayer comprising a first side and a second side, the first side defining a first region; a capture molecule for placement in the first region; a binding moiety for covalently attaching to a candidate compound, a portion of said binding moiety able to form a covalent bond with the capture molecule in the first region to form a complex; a reagent for disrupting the complex to create a releasing moiety attached to the candidate compound; and instructions for attaching the binding moiety to the candidate compound and for identifying the candidate compound attached to the releasing moiety. In some embodiments, the kit comprises instructions for identifying the amino acid sequence of the candidate compound. In some embodiments, the kit comprises instructions for identifying the structure of the candidate compound.

In another aspect, the invention provides a kit identifying whether a candidate compound traverses an animal cell membrane comprising an animal cell expressing a capture molecule in its cytosol; a binding moiety for covalently attaching to a candidate compound, a portion of said binding moiety able to form a covalent bond with the capture molecule to form a complex; a reagent for disrupting the complex to create a releasing moiety attached to the candidate compound; and instructions for attaching the binding moiety to the candidate compound and for identifying the candidate compound attached to the releasing moiety. In some embodiments, the kit comprises instructions for identifying the amino acid sequence of the candidate compound. In some embodiments, the kit comprises instructions for identifying the structure of the candidate compound.

Among other things, the present disclosure provides the following Embodiments:

1. A method, comprising:
   contacting an agent with a barrier; and/or
   detecting a product agent that is formed from an agent which has crossed the barrier.
2. The method of any one of the preceding embodiments, where the agent is a second agent as described herein.
3. The method of any one of the preceding embodiments, wherein the agent is a candidate compound linked to a binding moiety as described herein.
4. The method of any one of the preceding embodiments, wherein the agent comprises a scaffold agent moiety.
5. The method of any one of the preceding embodiments, wherein the agent comprises a CCL.
6. The method of any one of the preceding embodiments, wherein the CCL is or comprises —C(O)O—.
7. The method of any one of the preceding embodiments, wherein the CCL is or comprises vicinal diol.
8. The method of any one of the preceding embodiments, wherein the CCL is or comprises

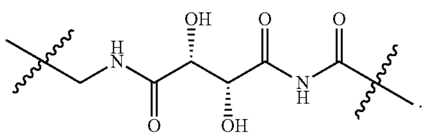 [SMILES: *CNC(=O)[C@H](O)[C@@H](O)C(=O)NC(*)=O]

9. The method of any one of the preceding embodiments, wherein the CCL is or comprises optionally substituted

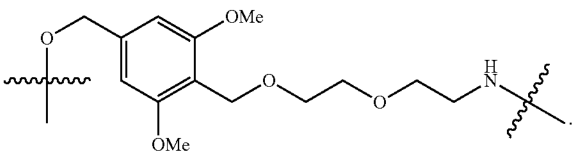 [SMILES: *NCCOCCOCc1c(OC)cc(CO*)cc1OC]

10. The method of any one of the preceding embodiments, wherein the CCL is or comprises optionally substituted

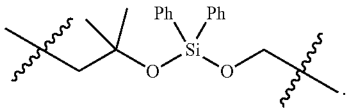 [SMILES: *CO[Si](OC(C)(C)C*)(c1ccccc1)c1ccccc1]

11. The method of any one of the preceding embodiments, wherein the CCL is or comprises optionally substituted

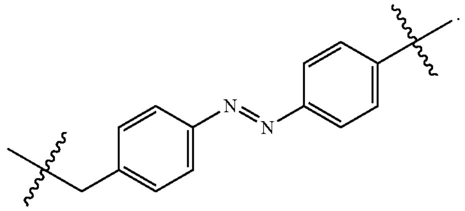 [SMILES: *Cc1ccc(/N=N/c2ccc(*)cc2)cc1]

12. The method of any one of the preceding embodiments, wherein the CCL is or comprises optionally substituted

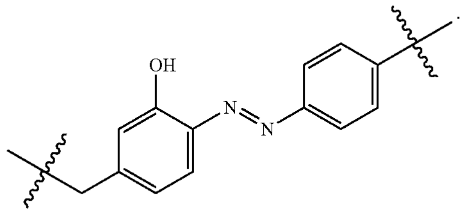 [SMILES: *Cc1ccc(/N=N/c2ccc(*)cc2)c(O)c1]

13. The method of any one of the preceding embodiments, wherein the CCL is or comprises optionally substituted

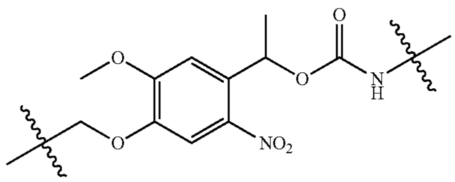

14. The method of any one of the preceding embodiments, wherein the CCL is or comprises optionally substituted

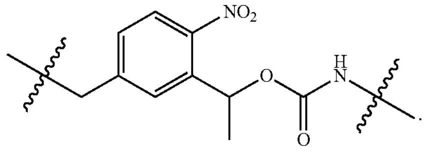 [SMILES: *Cc1ccc([N+](=O)[O-])c(C(C)OC(=O)N*)c1]

15. The method of any one of the preceding embodiments, wherein the CCL is or comprises optionally substituted

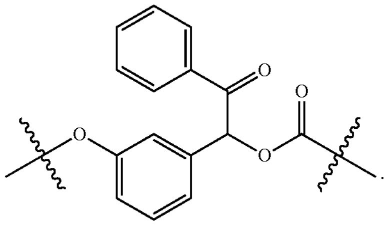 [SMILES: *Oc1cccc(C(OC(*)=O)C(=O)c2ccccc2)c1]

16. The method of any one of the preceding embodiments, wherein the CCL is or comprises optionally substituted

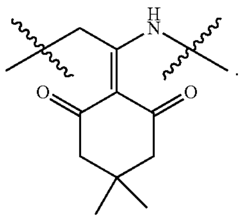 [SMILES: *CC(N*)=C1C(=O)CC(C)(C)CC1=O]

17. The method of any one of the preceding embodiments, wherein the CCL is or comprises —N═N—.
18. The method of any one of the preceding embodiments, wherein the CCL is or comprises —Ar—N═N—Ar—, wherein each Ar is independently an optionally substituted aromatic moiety.
19. The method of any one of the preceding embodiments, wherein the agent comprises a binding moiety.
20. The method of any one of the preceding embodiments, wherein the agent comprise a functional group (a second functional group).
21. The method of any one of the preceding embodiments, wherein a second functional group is or comprises FG2.
22. The method of any one of the preceding embodiments, wherein a second functional group is or comprises —Cl.
23. The method of any one of the preceding embodiments, wherein an agent has the structure of $R^B$-L-FG2 or a salt thereof, wherein $R^B$ is a scaffold agent moiety, FG2 is a functional group, and L is a covalent bond, or a bivalent optionally substituted, linear or branched $C_{1-30}$ group comprising one or more aliphatic moieties, aryl moieties, heteroaliphatic moieties each independently having 1-10 heteroatoms, heteroaromatic moieties each independently having 1-10 heteroatoms, or a combination of one or more of such moieties, wherein one or more methylene units of the group are optionally and independently replaced with $C_{1-6}$ alkylene, $C_{1-6}$ alkenylene, a bivalent $C_{1-6}$ heteroaliphatic group having 1-5 heteroatoms, —C≡C—, —N═N—, -Cy-, —$C(R')_2$—, —O—, —S—, —S—S—, —N(R')—, —$Si(R')_2$—, —C(O)—, —C(S)—, —C(NR')—, —C(O)N(R')—, —$C(O)C(R')_2N(R')$—, —N(R')C(O)N(R')—, —N(R')C(O)O—, —S(O)—, —$S(O)_2$—, —$S(O)_2N(R')$—, —C(O)S—, —C(O)O—, an amino acid residue, or —[(—O—$C(R')_2$—$C(R')_2$—$)_n$]—, wherein n is 1-20;

each -Cy- is independently an optionally substituted bivalent monocyclic, bicyclic or polycyclic group wherein each monocyclic ring is independently selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —OR, —C(O)R, —$CO_2$R, or —$SO_2$R;

each R is independently —H, or an optionally substituted group selected from $C_{1-20}$ aliphatic, $C_{1-20}$ heteroaliphatic having 1-10 heteroatoms, $C_{6-20}$ aryl, $C_{6-20}$ arylaliphatic, $C_{6-20}$ arylheteroaliphatic having 1-10 heteroatoms, 5-20 membered heteroaryl having 1-10 heteroatoms, and 3-20 membered heterocyclyl having 1-10 heteroatoms, or two R groups are optionally and independently taken together to form a covalent bond, or:

two or more R groups on the same atom are optionally and independently taken together with the atom to form an optionally substituted, 3-20 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

24. The method of any one of the preceding embodiments, wherein L is or comprises a CCL.
25. The method of any one of the preceding embodiments, wherein L is or comprises —$(CH_2)_n$—, wherein n is 1-20.
26. The method of any one of the preceding embodiments, wherein L is or comprises —$(CH_2)_4$—.
27. The method of any one of the preceding embodiments, wherein FG2 is —Cl.
28. The method of any one of the preceding embodiments, wherein -L-FG2 is Cl—$(CH_2)_6O(CH_2)_2O(CH_2)_2$NHC(O)$(CH_2)_2$C(O)—.
29. The method of any one of the preceding embodiments, wherein a scaffold agent is or comprises a stapled peptide.
30. The method of any one of the preceding embodiments, wherein a scaffold agent is or comprises a stapled peptide, and -L-FG2 is bonded to a stapled peptide moiety at its N-terminus optionally through a linker.
31. The method of any one of the preceding embodiments, wherein a barrier is or comprises a bilayer.
32. The method of any one of the preceding embodiments, wherein a barrier is or comprises a phospholipid bilayer.
33. The method of any one of the preceding embodiments, wherein a barrier is or comprises a biological barrier.
34. The method of any one of the preceding embodiments, wherein a barrier is or comprises a cell membrane.
35. The method of any one of the preceding embodiments, wherein a barrier is or comprises a monolayer of cells.

36. The method of any one of the preceding embodiments, wherein a product agent comprises a scaffold agent moiety and a releasing moiety and optionally a linker.
37. The method of any one of the preceding embodiments, wherein a product agent comprises a scaffold agent moiety, a functional group, and optionally a linker.
38. The method of any one of the preceding embodiments, wherein a product agent comprises a scaffold agent moiety, FG3, and optionally a linker.
39. The method of any one of the preceding embodiments, wherein a product agent and an agent share the same scaffold moiety or a characteristic portion thereof.
40. The method of any one of the preceding embodiments, wherein a product agent and an agent share the same scaffold moiety.
41. The method of any one of the preceding embodiments, wherein the product agent has the structure of $R^P$-L-FG3 or a salt thereof.
42. The method of any one of the preceding embodiments, wherein L of a product agent is or comprises $-(CH_2)_n-$, wherein n is 1-20.
43. The method of any one of the preceding embodiments, wherein L of a product agent is or comprises $-(CH_2)_4-$.
44. The method of any one of the preceding embodiments, wherein FG3 is or comprises —OH.
45. The method of any one of the preceding embodiments, wherein FG3 is or comprises -Cy-.
46. The method of any one of the preceding embodiments, wherein FG3 is or comprises an optionally substituted partially saturated or aromatic ring.
47. The method of any one of the preceding embodiments 1-44, wherein FG3 is —OH.
48. The method of any one of the preceding embodiments 1-44, wherein -L-FG3 is $HO-(CH_2)_6O(CH_2)_2O(CH_2)_2NHC(O)(CH_2)_2C(O)-$.
49. The method of any one of the preceding embodiments, wherein a scaffold agent is or comprises a stapled peptide, and -L-FG3 is bonded to a stapled peptide moiety at its N-terminus optionally through a linker.
50. The method of any one of the preceding embodiments, wherein the agent is directly administered to one side of the barrier (a second region).
51. The method of any one of the preceding embodiments, wherein the other side of the barrier (a first region) comprises a first agent.
52. The method of any one of the preceding embodiments, wherein a first region is inside a cell.
53. The method of any one of the preceding embodiments, wherein a first region comprises a first agent as described herein.
54. The method of any one of the preceding embodiments, wherein a first agent is or comprises a capture molecule as described herein.
55. The method of any one of the preceding embodiments, wherein a first agent comprises a CCL.
56. The method of any one of the preceding embodiments, wherein a first agent comprises a functional group (a first functional group).
57. The method of any one of the preceding embodiments, wherein the first functional group reacts with a functional group of the agent (a second functional group).
58. The method of any one of the preceding embodiments, wherein the CCL of a first agent is or comprises —C(O)O—.
59. The method of any one of the preceding embodiments, wherein the CCL of a first agent is or comprises vicinal diol.
60. The method of any one of the preceding embodiments, wherein the CCL of a first agent is or comprises

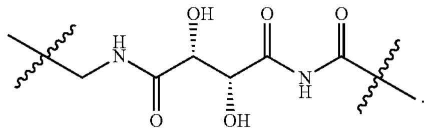 [SMILES: *CNC(=O)[C@H](O)[C@@H](O)C(=O)NC(*)=O]

61. The method of any one of the preceding embodiments, wherein the CCL of a first agent is or comprises optionally substituted

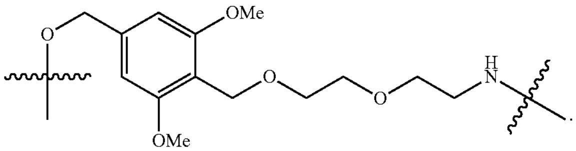 [SMILES: *NCCOCCOCc1c(OC)cc(CO*)cc1OC]

62. The method of any one of the preceding embodiments, wherein the CCL of a first agent is or comprises optionally substituted

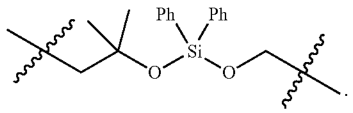 [SMILES: *CO[Si](OC(C)(C)C*)(c1ccccc1)c1ccccc1]

63. The method of any one of the preceding embodiments, wherein the CCL of a first agent is or comprises optionally substituted

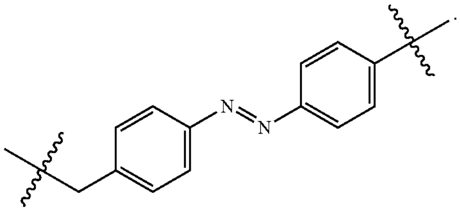 [SMILES: *Cc1ccc(/N=N/c2ccc(*)cc2)cc1]

64. The method of any one of the preceding embodiments, wherein the CCL of a first agent is or comprises optionally substituted

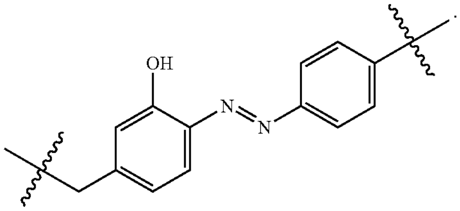 [SMILES: *Cc1ccc(/N=N/c2ccc(*)cc2)c(O)c1]

65. The method of any one of the preceding embodiments, wherein the CCL of a first agent is or comprises optionally substituted

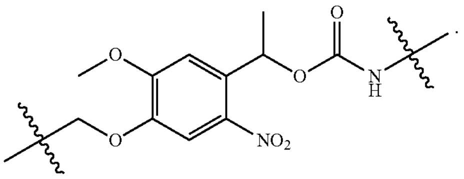 [SMILES: *COc1cc([N+](=O)[O-])c(C(C)OC(=O)N*)cc1OC]

66. The method of any one of the preceding embodiments, wherein the CCL of a first agent is or comprises optionally substituted

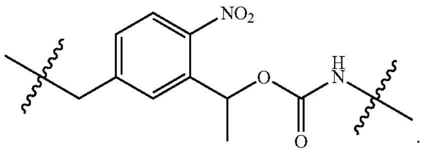 [SMILES: *Cc1ccc([N+](=O)[O-])c(C(C)OC(=O)N*)c1]

67. The method of any one of the preceding embodiments, wherein the CCL of a first agent is or comprises optionally substituted

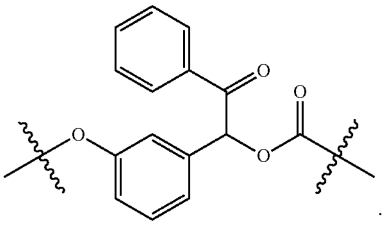 [SMILES: *Oc1cccc(C(OC(*)=O)C(=O)c2ccccc2)c1]

68. The method of any one of the preceding embodiments, wherein the CCL of a first agent is or comprises optionally substituted

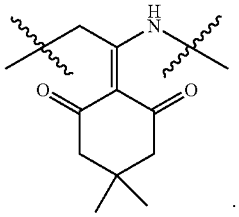 [SMILES: *CC(N*)=C1C(=O)CC(C)(C)CC1=O]

69. The method of any one of the preceding embodiments, wherein the CCL of a first agent is or comprises —N═N—.
70. The method of any one of the preceding embodiments, wherein the CCL of a first agent is or comprises —Ar—N═N—Ar—, wherein each Ar is independently an optionally substituted aromatic moiety.
71. The method of any one of the preceding embodiments, wherein a first functional group is —COOH.
72. The method of any one of the preceding embodiments, wherein a first agent is or comprises a polypeptide agent.
73. The method of any one of the preceding embodiments, wherein a first agent is or comprises a polypeptide agent, wherein the peptide agent is or comprises an enzyme.
74. The method of any one of the preceding embodiments, wherein a first agent is or comprises a polypeptide agent, wherein the peptide agent is or comprises a dehalogenase.
75. The method of any one of the preceding embodiments, wherein a first agent is or comprises a polypeptide agent, wherein the peptide agent is or comprises DhaA.
76. The method of any one of the preceding embodiments, wherein a first functional group is —COOH or a salt form of an amino acid residue.
77. The method of any one of the preceding embodiments, wherein the first agent comprises a tag.
78. The method of any one of the preceding embodiments, wherein a tag is or comprises a His tag.
79. The method of any one of the preceding embodiments, wherein a tag is or comprises a GST tag.
80. The method of any one of the preceding embodiments, wherein a tag is or comprises a FLAG tag.
81. The method of any one of the preceding embodiments, wherein a tag is or comprises a SNAP tag.
82. The method of any one of the preceding embodiments, wherein a first agent has the structure of $R^C$-L-FG1 or salt thereof, wherein $R^C$ is a scaffold agent moiety, FG1 is a functional group, and L is a linker.
83. The method of any one of the preceding embodiments, wherein a scaffold agent of a first agent is a protein or polypeptide expressed in a cell.
84. The method of any one of the preceding embodiments, wherein FG1 and FG2 can react with other when in contact.
85. The method of any one of the preceding embodiments, wherein a reaction between FG1 and FG2 is a bioorthogonal reaction.
86. The method of any one of the preceding embodiments, wherein a reaction between FG1 and FG2 is a cycloaddition reaction.
87. The method of any one of the preceding embodiments, wherein one of FG1 and FG2 is or comprises a dipole or a diene, and the other is or comprises an alkene or alkyne.
88. The method of any one of the preceding embodiments, wherein one of FG1 and FG2 is or comprises —$N_3$, and the other is or comprises an alkyne.
89. The method of any one of embodiments 1-85, wherein one of FG1 and FG2 is or comprises —COOH or a salt or activated form thereof, and the other is or comprises a leaving group.
90. The method of any one of embodiments 1-85, wherein one of FG1 and FG2 is or comprises —COOH or a salt or activated form thereof, and the other is or comprises a leaving group, wherein a reaction between FG1 and FG2 is or comprises replacement of a leaving group by —C(O)O—.
91. The method of any one of the preceding embodiments, wherein the first agent does not significantly cross the barrier.
92. The method of any one of the preceding embodiments, wherein the first agent is formed by a reaction between a polypeptide or a protein with a compound having the structure of $R^F$-L-FG1 or a salt thereof.
93. The method of any one of the preceding embodiments, wherein the polypeptide or protein is a mutant enzyme.
94. The method of any one of the preceding embodiments, wherein the polypeptide or protein is a mutant dehalogenase which has significantly reduced or removed hydrolase activity.

95. The method of any one of the preceding embodiments, wherein the agent is covalently bonded to a first agent to form a complex.

96. The method of any one of the preceding embodiments, wherein a complex is enriched.

97. The method of any one of the preceding embodiments, wherein a complex is enriched based on a tag of a first agent.

98. The method of any one of the preceding embodiments, wherein a complex is formed in a cell.

99. The method of any one of the preceding embodiments, wherein a complex is enriched from a cell lysate.

100. The method of any one of the preceding embodiments, wherein a complex comprises a CCL.

101. The method of any one of the preceding embodiments, wherein the CCL of a complex is or comprises —C(O)O—.

102. The method of any one of the preceding embodiments, wherein the CCL of a complex is or comprises vicinal diol.

103. The method of any one of the preceding embodiments, wherein the CCL of a complex is or comprises

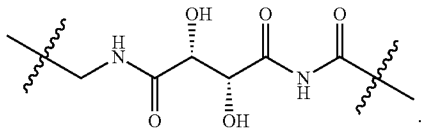 [SMILES: *CNC(=O)[C@H](O)[C@@H](O)C(=O)NC(*)=O]

104. The method of any one of the preceding embodiments, wherein the CCL of a complex is or comprises optionally substituted

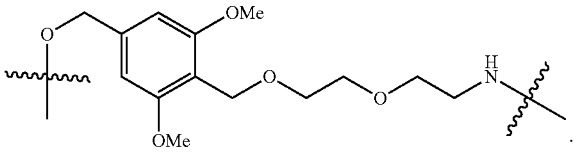 [SMILES: *NCCOCCOCc1c(OC)cc(CO*)cc1OC]

105. The method of any one of the preceding embodiments, wherein the CCL of a complex is or comprises optionally substituted

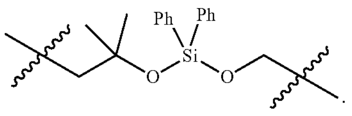 [SMILES: *CO[Si](OC(C)(C)C*)(c1ccccc1)c1ccccc1]

106. The method of any one of the preceding embodiments, wherein the CCL of a complex is or comprises optionally substituted

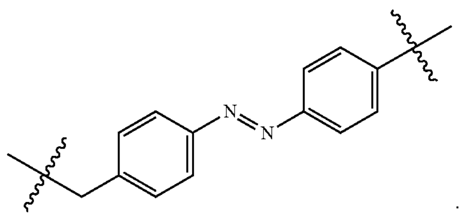 [SMILES: *Cc1ccc(/N=N/c2ccc(*)cc2)cc1]

107. The method of any one of the preceding embodiments, wherein the CCL of a complex is or comprises optionally substituted

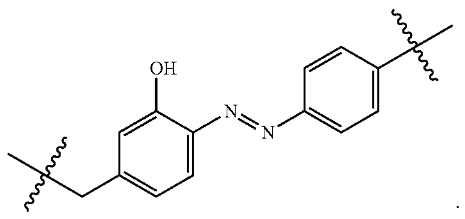 [SMILES: *Cc1ccc(/N=N/c2ccc(*)cc2)c(O)c1]

108. The method of any one of the preceding embodiments, wherein the CCL of a complex is or comprises optionally substituted

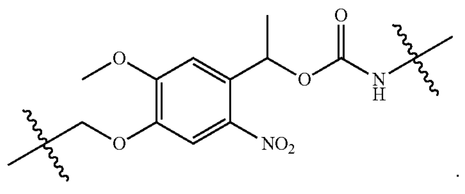 [SMILES: *COc1cc([N+](=O)[O-])c(C(C)OC(=O)N*)cc1OC]

109. The method of any one of the preceding embodiments, wherein the CCL of a complex is or comprises optionally substituted

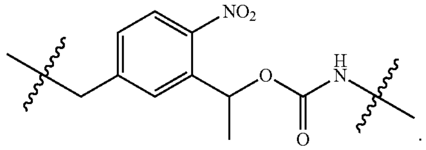 [SMILES: *Cc1ccc([N+](=O)[O-])c(C(C)OC(=O)N*)c1]

110. The method of any one of the preceding embodiments, wherein the CCL of a complex is or comprises optionally substituted

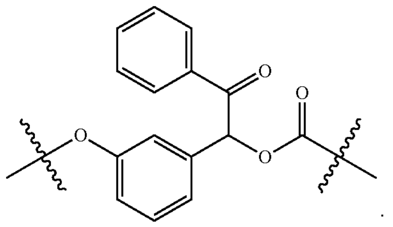 [SMILES: *Oc1cccc(C(OC(*)=O)C(=O)c2ccccc2)c1]

111. The method of any one of the preceding embodiments, wherein the CCL of a complex is or comprises optionally substituted

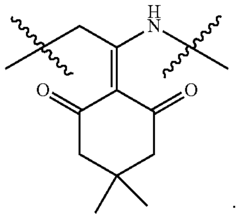 [SMILES: *CC(N*)=C1C(=O)CC(C)(C)CC1=O]

.

112. The method of any one of the preceding embodiments, wherein the CCL of a complex is or comprises —N═N—.

113. The method of any one of the preceding embodiments, wherein the CCL of a complex is or comprises —Ar—N═N—Ar—, wherein each Ar is independently an optionally substituted aromatic moiety.

114. The method of any one of the preceding embodiments, wherein the complex agent has the structure of $R^C$-L-$L^P$-L-R B or a salt thereof.

115. The method of any one of the preceding embodiments, wherein $L^P$ comprises a reaction product moiety of a functional group of an agent and a functional group of a first agent.

116. The method of any one of the preceding embodiments, wherein $L^P$ is or comprises —C(O)O—.

117. The method of any one of the preceding embodiments, wherein $L^P$ is or comprises -Cy-.

118. The method of any one of the preceding embodiments, wherein $L^P$ is or comprises an optionally substituted partially saturated or aromatic ring.

119. The method of any one of the preceding embodiments, wherein L bonded to $R^C$ and/or L bonded to $R^B$ independently comprise a CCL as described herein.

120. The method of anyone of the preceding embodiments, wherein a complex is a transient intermediate of an enzymatic reaction.

121. The method of anyone of the preceding embodiments, wherein a complex is a sufficiently stable for enrichment, isolation, and/or purification.

122. The method of any one of the preceding embodiments, wherein a complex does not significantly cross a barrier.

123. The method of any one of the preceding embodiments, wherein a complex is converted into a product agent.

124. The method of any one of the preceding embodiments, wherein a complex is converted into a product agent by base hydrolysis.

125. The method of any one of the preceding embodiments, wherein a complex is converted into a product agent by cleavage of a CCL.

126. The method of any one of the preceding embodiments, wherein a complex is converted into a product agent by enzymatic cleavage of a CCL.

127. The method of any one of the preceding embodiments, wherein a product agent comprises a releasing moiety which is different from a second functional group.

128. The method of any one of the preceding embodiments, wherein a product agent of the agent differs from the agent in that the product agent comprises a releasing moiety that is not a second functional group.

129. The method of any one of the preceding embodiments, wherein a product agent of the agent and the agent are the same except that the product agent comprises a releasing moiety and the agent comprises a second functional group.

130. The method of any one of the preceding embodiments, wherein a releasing moiety is formed after cleavage of a CCL.

131. The method of any one of the preceding embodiments, wherein a releasing moiety is or comprises a moiety or a portion thereof, wherein the moiety is formed by a reaction between a first and a second functional groups.

132. The method of any one of the preceding embodiments, wherein a releasing moiety is or comprises —OH.

133. The method of any one of the preceding embodiments, wherein a product agent is detected by mass spectrometry.

134. The method of anyone of the preceding embodiments, wherein the agent contacts the barrier together with a positive and/or a negative reference agent.

135. A method, comprising:

contacting a plurality of agents with a barrier; and/or detecting a plurality of product agents that are formed from an agent which has crossed the barrier.

136. The method of embodiment 135, wherein the plurality of agents are agents of a library.

137. The method of embodiment 135, wherein the plurality of agents are peptide agents of a peptide library.

138. The method of embodiment 135, wherein the plurality of agents are stapled peptide agents of a stapled peptide library.

139. The method of any one of embodiments 135-138, wherein the library is assessed without purification.

140. The method of any one of embodiments 135-139, wherein each agent of the plurality is independently an agent described in any one of the preceding embodiments.

141. The method of any one of embodiments 135-140, wherein each product agent of the plurality is independently a product agent described in any one of the preceding embodiments.

142. The method of any one of embodiments 135-141, wherein the plurality of agents can react with a plurality of first agents when contacted.

143. The method of any one of embodiments 135-142, wherein each agent of the plurality can independently react with a first agent of the plurality when contacted.

144. The method of any one of embodiments 135-143, wherein each agent of the plurality independently comprises a functional group (a second functional group).

145. The method of any one of embodiments 135-144, wherein each agent of the plurality independently comprises the same functional group (a second functional group).

146. The method of any one of embodiments 135-144, wherein agents of the plurality independently comprise different functional groups (second functional groups).

147. The method of any one of embodiments 135-146, wherein each first agent of the plurality independently comprises a functional group (a first functional group).

148. The method of any one of embodiments 135-147, wherein each first agent of the plurality independently comprises the same functional group (a first functional group).

149. The method of any one of embodiments 135-147, wherein first agents of the plurality independently comprise different functional groups (first functional groups).

150. The method of any one of embodiments 135-149, wherein agents of the plurality that cross the barrier form a plurality of complexes with the plurality of first agents.

151. The method of any one of embodiments 135-150, wherein one or more or all complexes of the plurality independently comprise a tag.

152. The method of any one of embodiments 135-151, wherein one or more or all complexes of the plurality independently comprise the same tag.

153. The method of any one of embodiments 135-152, wherein one or more or all complexes of the plurality independently comprise a CCL.

154. The method of any one of embodiments 135-153, wherein one or more or all complexes of the plurality independently comprise the same CCL.

155. The method of any one of embodiments 135-154, wherein the plurality of complexes is converted into a plurality of product agents.

156. The method of any one of embodiments 135-155, wherein the plurality of complexes is converted into a plurality of product agents by base hydrolysis.

157. The method of any one of embodiments 135-156, wherein the plurality of complexes is converted into a plurality of product agents by base hydrolysis of one or more CCLs in one or more complexes.

158. The method of any one of embodiments 135-155, wherein the plurality of complexes is converted into a plurality of product agents by enzymatic cleavage of one or more CCLs in one or more complexes.

159. The method of any one of embodiments 135-158, wherein the plurality of complexes is detected using mass spectrometry.

160. The method of any one of the preceding embodiments, wherein each product agent independently comprises the same scaffold agent moiety as an corresponding agent.

161. The method of any one of the preceding embodiments, wherein a scaffold agent is or comprises a peptide.

162. The method of any one of the preceding embodiments, wherein a scaffold agent is or comprises a stapled peptide.

163. The method of anyone of the preceding embodiments, wherein a scaffold agent moiety is or comprises the amino acid sequence or a characteristic portion thereof of the scaffold agent.

164. The method of anyone of the preceding embodiments, wherein a scaffold agent moiety is or comprises one or more or all staples of the scaffold agent.

165. The method of any one of the preceding embodiments, wherein if a product agent is detected, it is determined that the agent crosses the barrier.

166. The method of any one of the preceding embodiments, wherein if a product agent is detected to reach a certain level, it is determined that the agent crosses the barrier.

167. The method of any one of the preceding embodiments, wherein the level is 2, 3, 4, 5, 6, 7, 8, 9, 10, 20, 30, 40, 50, 100, 200, 300, 400, or 500 times of a level observed under a comparable condition for a negative reference agent.

168. The method of any one of the preceding embodiments, wherein a negative reference agent does not cross the barrier.

169. The method of any one of the preceding embodiments, wherein a scaffold agent comprises 170. An agent of any one of the preceding embodiments.

171. A first agent of any one of the preceding embodiments.

172. A complex of any one of the preceding embodiments.

173. A product agent of any one of the preceding embodiments.

174. A plurality of agents of any one of the preceding embodiments.

175. A plurality of first agents of any one of the preceding embodiments.

176. A plurality of second agents of any one of the preceding embodiments.

177. A plurality of complexes of any one of the preceding embodiments.

178. A plurality of product agents of any one of the preceding embodiments.

179. A system or composition, comprising one or more or all of an agent, a first agent, a complex, and a product agent of any one of the preceding embodiments.

180. A system or composition, comprising an agent and a first agent of any one of the preceding embodiments.

181. A system or composition, comprising an agent and a complex agent of any one of the preceding embodiments.

182. A system or composition, comprising an agent and a product agent of any one of the preceding embodiments.

183. A system or composition, comprising an agent, a first agent, a product agent of any one of the preceding embodiments.

184. A system or composition, comprising an agent, a first agent, a product agent of any one of the preceding embodiments.

185. A system or composition, comprising an agent, a first agent, a complex, and a product agent of any one of the preceding embodiments.

186. A system or composition, comprising one or more or all of a plurality of agents, a plurality of first agents, a plurality of complexes, and a plurality of product agents of any one of the preceding embodiments.

187. A system or composition, comprising a plurality of agents and a plurality of first agents of any one of the preceding embodiments.

188. A system or composition, comprising a plurality of agents and a plurality of complexes of any one of the preceding embodiments.

189. A system or composition, comprising a plurality of agents and a plurality of product agents of any one of the preceding embodiments.

190. A system or composition, comprising a plurality of agents, a plurality of first agents, a plurality of product agents of any one of the preceding embodiments.

191. A system or composition, comprising a plurality of agents, a plurality of first agents, a plurality of product agents of any one of the preceding embodiments.

192. A system or composition, comprising a plurality of agents, a plurality of first agents, a plurality of complexes, and a plurality of product agents of any one of the preceding embodiments.

193. The system or composition of any one of the preceding embodiments, comprising a barrier.

194. A cell, comprising an agent, a plurality of agent, or a composition or a system of any one of embodiments 170-192.

195. A plurality of cells, one or more or all of which independently comprise an agent, a plurality of agent, or a composition or a system of any one of embodiments 170-192.

196. The system or composition of any one of the preceding embodiments, comprising a plurality of cells.

197. The system or composition of any one of the preceding embodiments, comprising a plurality of cells, each of which is independently a cell of embodiment 194.

198. The system or composition of any one of the preceding embodiments, comprising a plurality of cells of embodiment 195.

199. A method for identifying one or more candidate compounds that traverse an cell monolayer, the method comprising:
   providing cell monolayer comprising a first side and a second side, the first side defining a first region, said first region comprising one or more capture molecules;
   adding a plurality of distinct candidate compounds, each distinct candidate compound attached to a binding moiety, to a second region defined by the second side of the cell monolayer, under conditions whereby each distinct candidate compound of the plurality traversing the cell monolayer enters the first region and forms a complex with a capture molecule in the first region via a covalent bond between a portion of the binding moiety attached to the distinct candidate compound and the capture molecule, wherein one or more complexes are formed;
   disrupting the one or more complexes to create one or more distinct candidate compounds each attached to a releasing moiety, said releasing moiety different from the binding moiety; and
   identifying the one or more distinct candidate compounds attached to the releasing moiety as being one or more candidate compounds that traverses an animal cell monolayer.

200. A method for determining if a candidate compound traverses an animal cell monolayer, the method comprising:
   providing a cell monolayer comprising a first side and a second side, the first side defining a first region, said first region comprising one or more capture molecules;
   adding the candidate compound attached to a binding moiety to a second region defined by the second side of the cell monolayer, under conditions whereby the candidate compound traversing the cell monolayer enters the first region and forms a complex with a capture molecule in the first region via a covalent bond between a portion of the binding moiety attached to the candidate compound and the capture molecule;
   disrupting the complex to create the candidate compound attached to a releasing moiety, said releasing moiety different from the binding moiety; and
   identifying the candidate compound attached to the releasing moiety as being a compound that traverses an animal cell monolayer.

201. A method for identifying one or more candidate compounds that traverse an animal cell membrane, the method comprising:
   providing phospholipid bilayer comprising a first side and a second side, the first side defining a first region, said first region comprising one or more capture molecules;
   adding a plurality of distinct candidate compounds, each distinct candidate compound attached to a binding moiety, to a second region defined by the second side of the phospholipid bilayer, under conditions whereby each distinct candidate compound of the plurality traversing the phospholipid bilayer enters the first region and forms a complex with a capture molecule in the first region via a covalent bond between a portion of the binding moiety attached to the distinct candidate compound and the capture molecule, wherein one or more complexes are formed;
   disrupting the one or more complexes to create one or more distinct candidate compounds each attached to a releasing moiety, said releasing moiety different from the binding moiety; and
   identifying the one or more distinct candidate compounds attached to the releasing moiety as being one or more candidate compounds that traverses an animal cell membrane.

202. A method for determining if a candidate compound traverses an animal cell membrane, the method comprising:
   providing phospholipid bilayer comprising a first side and a second side, the first side defining a first region, said first region comprising one or more capture molecules;
   adding the candidate compound attached to a binding moiety to a second region defined by the second side of the phospholipid bilayer, under conditions whereby the candidate compound traversing the phospholipid bilayer enters the first region and forms a complex with a capture molecule in the first region via a covalent bond between a portion of the binding moiety attached to the candidate compound and the capture molecule;
   disrupting the complex to create the candidate compound attached to a releasing moiety, said releasing moiety different from the binding moiety; and
   identifying the candidate compound attached to the releasing moiety as being a compound that traverses an animal cell membrane.

203. The method of embodiment 201 or 202, wherein the phospholipid bilayer is a cell membrane of an animal cell and the first region is a cytosol of the animal cell.

204. The method of embodiment 201 or 202, wherein the phospholipid bilayer is contiguous and the first region is an interior of a liposome.

205. The method of embodiment 201 or 202, wherein the phospholipid bilayer is contiguous and the first region is a cytosol of an animal cell.

206. The method of embodiment 205, wherein the animal cell is a cell of a vertebrate animal.

207. The method of embodiment 206, wherein the vertebrate animal is a mammal.

208. The method of embodiment 207, wherein the mammal is a human.

209. The method of embodiment 205, wherein the animal cell has a nucleus.

210. The method of embodiment 201 or 202, wherein the phospholipid bilayer is planar.
211. The method of embodiment 201 or 202, further comprising the step of disrupting the phospholipid bilayer so that the first region and the second region are combined to create a mixed region after complex formation in the first region.
212. The method of any one of embodiments 199-202, wherein the binding moiety is larger in mass than the releasing moiety.
213. The method of any one of embodiments 199-202, wherein the binding moiety is smaller in mass than the releasing moiety.
214. The method of any one of embodiments 199-202, wherein the releasing moiety is created by replacing at least one atom of the binding moiety with at least one different atom.
215. The method of any one of embodiments 199-202, wherein the complex is disrupted by exposing the complex to an environment with a pH of 11.0 or higher.
216. The method of embodiment 215, wherein the pH is 11.5 or higher.
217. The method of embodiment 216, wherein the pH is 12.0 or higher.
218. The method of any one of embodiments 199-202, wherein the identification step is by mass spectrometry analysis.
219. The method of any one of embodiments 199-202, wherein the identification step is by Edman degradation analysis.
220. The method of any one of embodiments 199-202, wherein the candidate compound comprises a peptide.
221. The method of embodiment 220, wherein the peptide is selected from the group consisting of a stapled peptide, a synthetic peptide, a stitched peptide, and a combination of two or more of the foregoing.
222. The method of embodiment 219 or 220, wherein the peptide comprises, consists essentially of, or consists of an alpha helical turn.
223. The method of embodiment 219, wherein the candidate compound further comprises a small molecule scaffold stabilizing an alpha helical turn in the peptide.
224. The method of any one of embodiments 199-202, wherein the capture molecule comprises a linker comprising a chemically cleavable linker and a functional group, said functional group able to covalently bind to at least a portion of a binding moiety attached to a candidate compound.
225. The method of any one of embodiments 199-202, wherein the capture molecule comprises, consists essentially of, or consists of a mutant form of a haloalkane dehalogenase, said mutant form lacking a hydrolase activity.
226. The method of any one of embodiments 199-202, wherein the capture molecule forms a covalent bond with a group selected from the group consisting of a benzylguanine derivative and a $O_2$-benzylcystosine derivative.
227. The method of any one of embodiments 199-202, wherein the capture molecule comprises, consists essentially of, or consists of a mutant form of an $O^6$-alkylguanine-DNA alkyltransferase.
228. The method of any one of embodiments 199-227, wherein disrupting the one or more complexes is or comprises breakup of an intermediate and/or release of a product by a capture molecule.
229. A kit for identifying whether a candidate compound traverses an animal cell membrane comprising:
   a phospholipid bilayer comprising a first side and a second side, the first side defining a first region;
   one or more capture molecules for placement in the first region;
   a binding moiety for covalently attaching to a candidate compound, said small molecule linker able to form a covalent bond with the capture molecule in the first region to form a complex;
   a reagent for disrupting the complex to create a releasing moiety attached to the candidate compound; and/or
   instructions for attaching the binding moiety to the candidate compound and for identifying the candidate compound attached to the releasing moiety.

The following examples in no way limit the present invention.

EXEMPLIFICATION

Certain embodiments of the provided technologies are exemplified in one or more Examples below. Those skilled in the art appreciate that conditions, agents, etc. described in such Examples may be suitably adjusted and/or modified.

Example 1

This example describes a standard method used in various embodiments of the present invention.

Animal cells (e.g., human HEK 293 cells commercially available from the American Type Culture Collection, Manassas, VA) were seeded in tissue culture plate and cultured in MEM (Minimal Essential Media) supplemented with 10% FBS and 1% PenStrep, and transfected using standard method with an expression vector encoding a capture molecule. Following transfection, the transfected cells were returned to the cell culture incubator (e.g., 37° C., 5% $CO_2$). Control cells were transfected with empty vector. Transfection was done using the Turbofect reagent sold by Thermo Fisher Scientific (Waltham, MA; catalog no. R0532) according to manufacturer's instruction.

48 hours after transfection, the transfected cells were split into 96 well or 12 well tissue culture plates. Following cell adherence to the plate (approximately 6 hours in incubator), the cells were treated with either DMSO (dimethyl sulfoxide) or a chloro-alkane-tagged peptide that was being tested for an ability to traverse the cell membrane for 24 hours incubation.

After 24 hours of incubation, the media fraction and the cell fraction were collected as follows:

For the Media fraction, 50 μL of cell culture media (i.e., conditioned media) from each sample was collected and transferred to a tissue culture plate that has low binding to protein, such as the Protein Lo-Bind plate sold by Eppendorf, catalog Nos. 0030504305, 951031305, and 951031704 (Eppendorf North America, Hauppauge, NY).

For the cellular fraction, the cells were trypsinized to detach them from the plate, followed by addition of media to quench the trypsin. This trypsin-media-cell suspension was transferred to a 96-well V-bottom plate followed by centrifugation, so that the cells can pellet at the bottom of the wells and the supernatant liquid can be removed to allow other washes. The cells are subjected to a series of washes, first, phosphate buffered saline (PBS) and second, fetal bovine serum (Heat Inactivated, complete FBS), and third, media. The sequential washes were done to remove any residual peptide that may be loosely connected to the external cell membrane but is not internalized by the cell. The final washed cell pellets were then resuspended in PBS. An equal volume (i.e., equal to the volume of the cells) of ammonium hydroxide base was added to the resuspended cells. The cell mixture with ammonium hydroxide, which had a pH of 12.0, was then returned to the 37° C. incubator (shaking at 3000 rpm) for 1 hour. During this 1-hour incubation, the cells underwent base hydrolysis.

Following base hydrolysis, the cell samples were dried in a SpeedVac (e.g., commercially available from Thermo-Fisher) overnight.

The following day, the dried sample was resuspended in 50 ul PBS to create the final cellular fraction. This final cellular fraction was then transferred to a protein Lo-Bind plate. A fresh solution of Methanol and 1% Formic acid was made and chilled to 4° C. 100 ul of chilled methanol 1% formic acid (FA) was added to both the media fractions and the final cellular fractions (each fraction in protein Lo-Bind plates), and the plate was stored at −20° C. for 4-5 hours to release the proteins and peptides from each of the fractions. The plates were then removed from −20° C. and their contents analyzed by mass spectrometry to look specifically for starting peptide in the media fraction and its base hydrolyzed analog in the cellular fraction.

For mass spectrometry analysis, the following methods were employed:

Compounds were separated via a 2.1×50 mm (1.7 μm particle size) AQUITY BEH C18 column (Waters, Milford, MA) heated at 50° C. using a Dionex Ultimate 3000 RSLCnano (Santa Clara, CA) system. The eluents used for separation were as follows: eluent A was 0.1% formic acid in water and eluent B was 0.1% formic acid in acetonitrile. Gradients were implemented at a flow rate of 200 μL/min using a linear gradient of 15% eluent B at time zero, 98% eluent B from 10 to 11.5 minutes, and 15% eluent B from 11.6 to 14 minutes. After separation, the compounds were introduced into a Thermo Scientific Q Exactive HF-X (Bremen, Germany) for mass spectrometric analysis. Data-dependent acquisitions (DDA) were performed as follows: MS1 events were comprised of the positive mass scan at a range of 500-1300 m/z followed by five HCD events at 25, 35 and 45% stepped normalized collision energy (NCE) on the most abundant ions from the MS1 scan; isolation window was set to 1.4 m/z. Dynamic exclusion duration was 2.0 s, and only 2+ and 3+ charged species were picked for dissociation. The ESI voltage was set to 3.5 kV, capillary temperature was 250° C., sheath gas was 35, aux gas was 10, and the Funnel RF level was set to 40. Resolution was 45,000 for MS1 scans, and 15,000 for MS/MS scans. AGC was set to 3E6 with a maximum injection time of 250 ms for MS1, and AGC was 1E5 with a maximum injection time of 250 ms for MS/MS scans. All MS1 and MS/MS spectra were produced from 1 microscan.

Example 2

In this Example 2, the methods of Example 1 were followed using the HaloTag protein sold by Promega as a portion of the capture molecule. Some known methods for determining if a candidate compound (e.g., a stapled peptide) can traverse a cell membrane require observation of cellular effect of the compound modulating an intracellular target. Other known methods may simply involve labeling a candidate compound with a small detectable marker (e.g., fluorescein isothiocyanate), incubating cells with the labeled compound for a time adequate for the compound to traverse the cell membrane, rinsing the cells fresh media or PBS, and inspecting the cells (e.g., under a fluorescent microscope) to see if the marker is contained within the cell (e.g., within the cytosol). See, for example, the methods described in Y. S. Chang et al., Proc. Natl. Acad. Sci. USA 110(36):E3445-54, 2013 (and supplemental material); U.S. Pat. No. 7,960,506; Chandra et al., J. Biochem Biophys Methods 70(3): 329-333, 2007; PCT Publication No. WO2015179691A2.

Figure 14A:
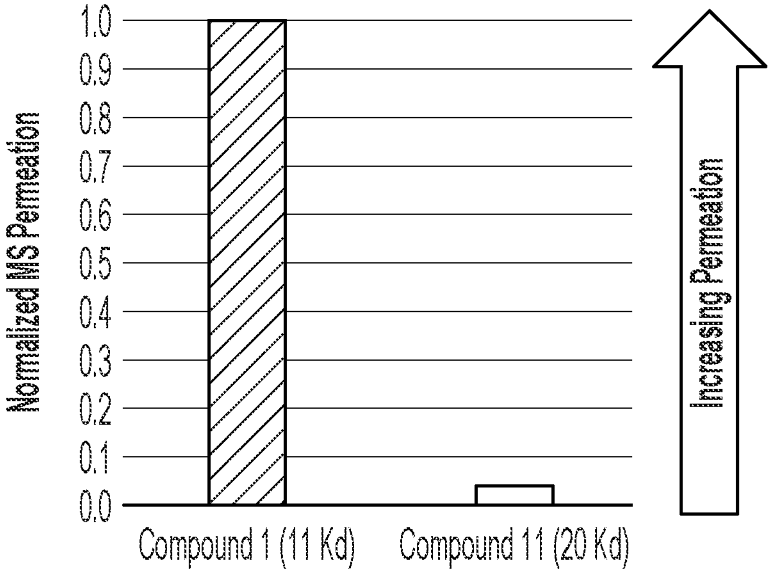
FIGS. 14A and 14B are bar graphs showing side by side comparisons of a cell membrane traversing compound, Compound 1, and Compound 11, which does not traverse the cell membrane, in NanoBRET (FIG. 14B) and mass spectrometry permeation (14A).
Figure 14B:
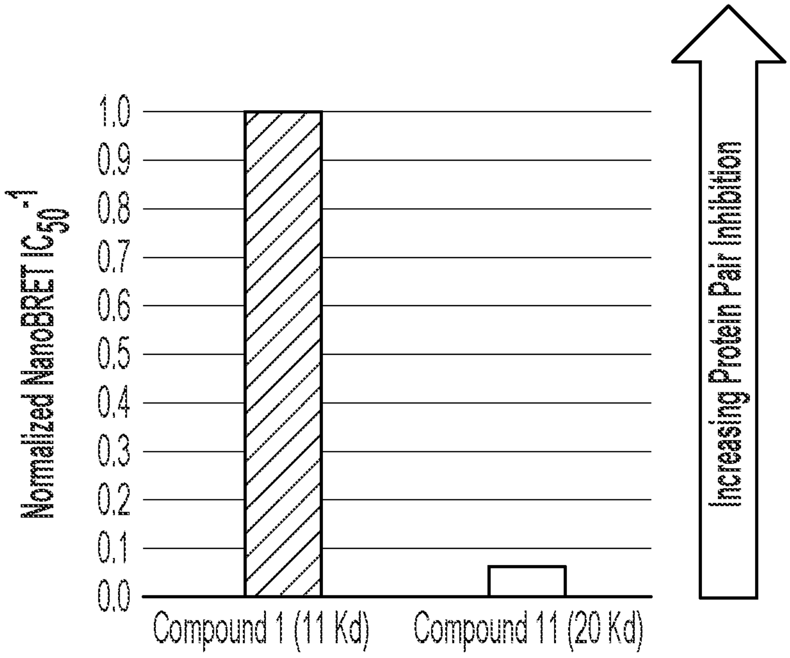

Using standard methods, peptides were generated using FMOC peptide synthesis and stapled with a hydrocarbon linker (see, e.g., U.S. Pat. No. 7,192,713) and were analyzed to determine whether they are able to traverse the cell membrane of human cells using standard methods. Compounds 1 and 11 were generated, where each specifically binds to the same target molecule with affinities of $K_D$ 11 nM (Compound 1) and $K_D$ 20 nM (Compound 11). FIGS. 14A and 14B show the results of two of these standard assays. Mass spectrometry permeation experiments were performed by incubating Compound 1 or Compound 11 with cells, applying rigorous washing of the cells to remove outer membrane-bound compound, and then lysing the cells to quantify the amount of internalized compound by mass spectrometry. As shown in FIG. 14A, a significant signal was observed for Compound 1 confirming cell internalization, and a very low signal was observed for Compound 11. These results show that Compound 1 traverses the cell membrane but Compound 11 does not. The second standard method was the NanoBRET™ assay (commercially available from Promega Corp., Madison, WI) which utilizes bioluminescence resonance energy transfer to quantify the inhibition or induction of protein interactions in live cells. Since both Compound 1 and Compound 11 specifically bind to the same target and are known disrupt a specific protein pair in vitro, the protein pair was transfected into live cells using the NanoBRET™ system (according to manufacturer's instructions), and significant inhibition of the protein interaction was observed after dosing the cells with Compound 1 (FIG. 14B), while very little inhibition of protein interaction was observed after dosing the cells with Compound 11. In other words, Compound 11 showed little inhibition because it was unable to get into the cytosol of the cell whereas Compound 1 was able to get into the cytosol of the cell and thus inhibited protein interaction. The data results shown in FIGS. 14A and 14B show that Compound 1 readily traverses the cell membrane and can inhibit its target protein and interactions but Compound 11 does not.

Thus, Compound 1 was been determined to be cell membrane permeable based on mass spectrometry permeation experiments (FIG. 14B) and on orthogonal NanoBRET™ (FIG. 14A), as well as other data not shown. Compound 1 was used as a positive control in the methods described herein.

Figure 15A:
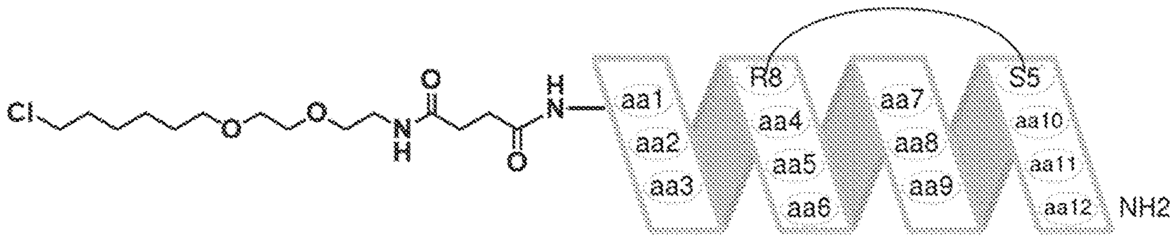
FIGS. 15A and 15B are drawings showing a non-limiting candidate compound of the invention, specifically the stapled peptide Compound 1 attached to: (a) a non-limiting binding moiety (FIG. 15A) and (b) a non-limiting releasing moiety (FIG. 15B).

A binding moiety having the structure:

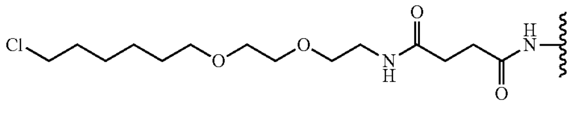 [SMILES: *NC(=O)CCC(=O)NCCOCCOCCCCCCCl]

was covalently attached to the C terminus of Compound 1 using standard methods to create the Compound 1-Cl molecule depicted in FIG. 15A.

In accordance with the methods described in Example 1, HEK 293 cells (from the ATCC) previously transfected with an expression vector encoding the HaloTag molecule were treated by adding 3 uM Compound 1-Cl to the culture media, and returning the treated cells to the incubator (i.e., at 37° C., 5% CO2) for 24 hours. During this 24 hour incubation, Compound 1—Cl, which was known to be able to traverse the cell membrane, entered the cytoplasm of the cells and covalently attached to the HaloTag protein in the cytoplasm via a covalent bond between the binding moiety on the Compound 1-Cl molecule and the HaloTag protein. Following the 24 hour incubation, the incubated cells were treated described in Example 1 and the media and cellular fractions separated and analyzed as described in Example 1. As part of the analysis, the cells were lysed in ammonium hydroxide (i.e., by base hydrolysis), which also disrupted the candidate compound: product of binding moiety and HaloTag:HaloTag protein complex, creating the Compound 1-OH molecule depicted in FIG. 15B, namely the candidate Compound 1 covalently attached to a releasing moiety.

with an expression vector encoding a capture molecule. In this example, the HaloTag protein was a portion of the capture molecule. Following transfection, the transfected cells were returned to the cell culture incubator (e.g., 37° C., 5% $CO_2$). Control cells were transfected with empty vector. Transfection in suspension FreeStyle 293-F cells was done using the 293fectin reagent and instructions from Thermo Fisher Scientific. 293fectin is a solution of cationic polymer, which interacts with the DNA to form small complexes which are diffusible and can be endocytosed into the cells.

48-72 hours after transfection, the transfected cells were split into 96 well deep-well tissue culture plates having low binding to protein (e.g., the protein Lo-Bind plate sold by Eppendorf). Next, the cells were treated with a clickable linker (PEG2) for two hours. The PEG2 clickable linker had the following structure:

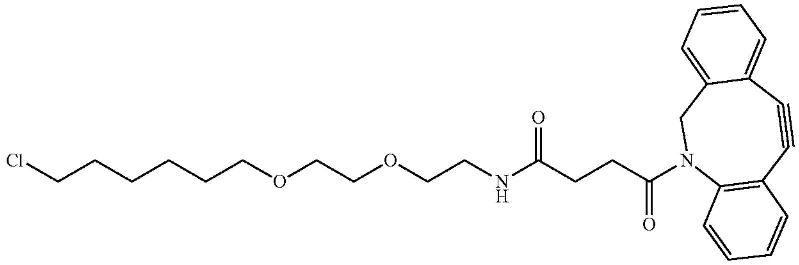

clickable PEG2 linker

Figure 15B:
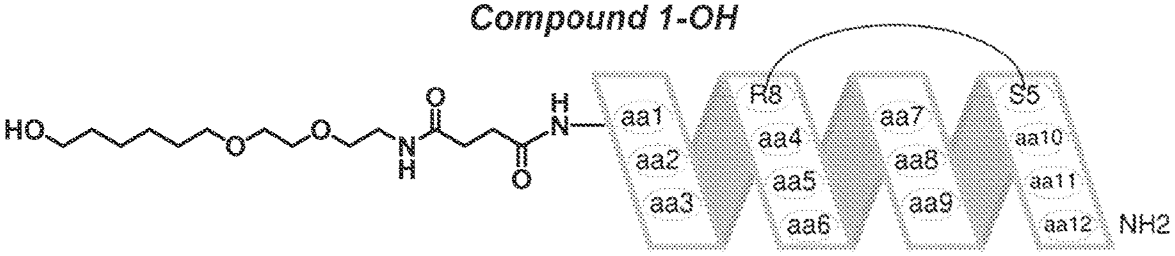

As shown in FIGS. 15A and 15B, the created Compound 1-OH molecule (e.g., a candidate compound attached to a releasing moiety; FIG. 15B) is different from the Compound 1-Cl molecule (e.g., a candidate compound attached to a binding moiety; FIG. 15A).

Figure 16A:
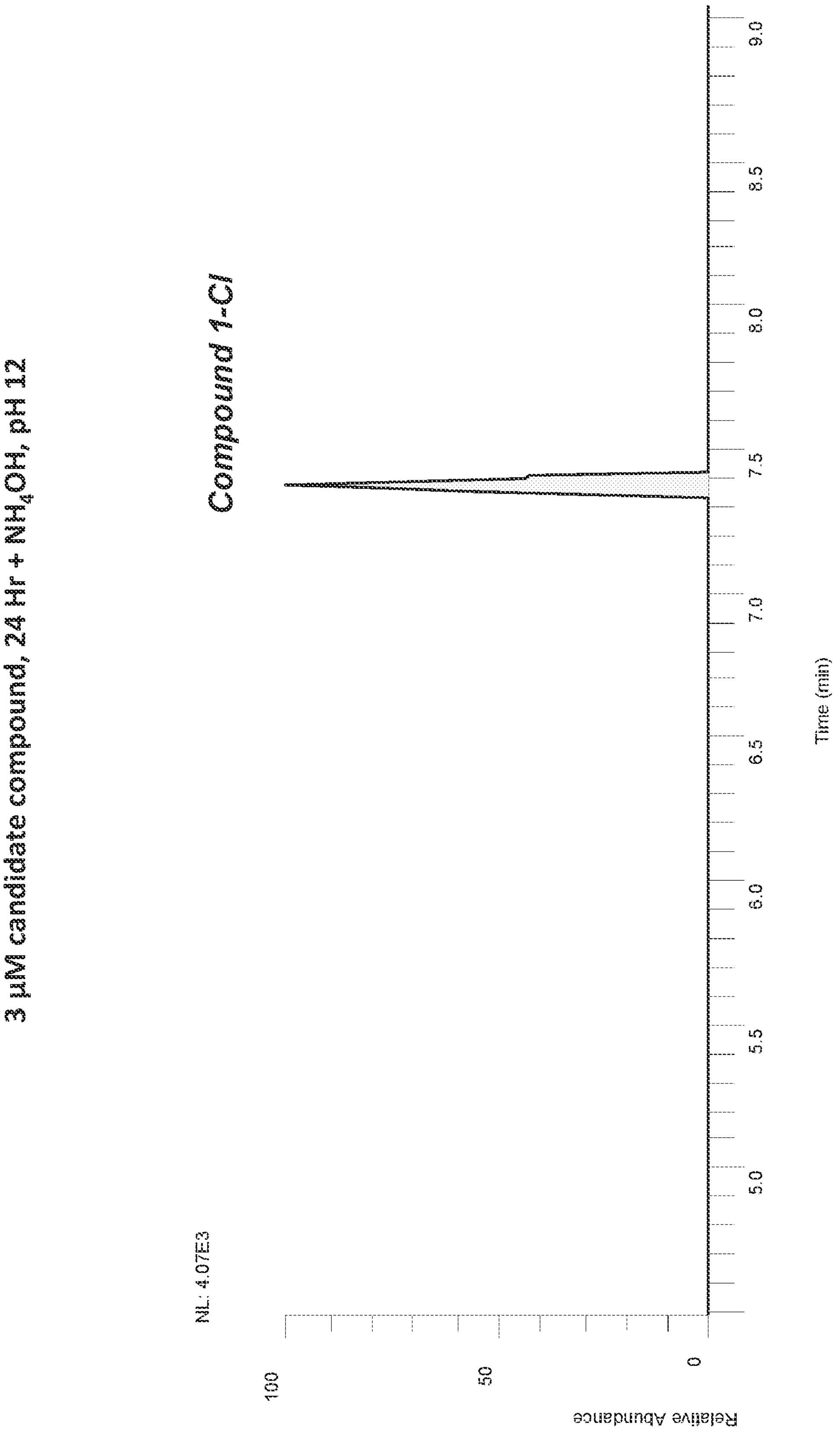
FIGS. 16A and 16B are mass spectra of the candidate compound attached to a binding moiety of FIG. 15A and the candidate compound attached to a releasing moiety of FIG. 15B, respectively.
Figure 16B:
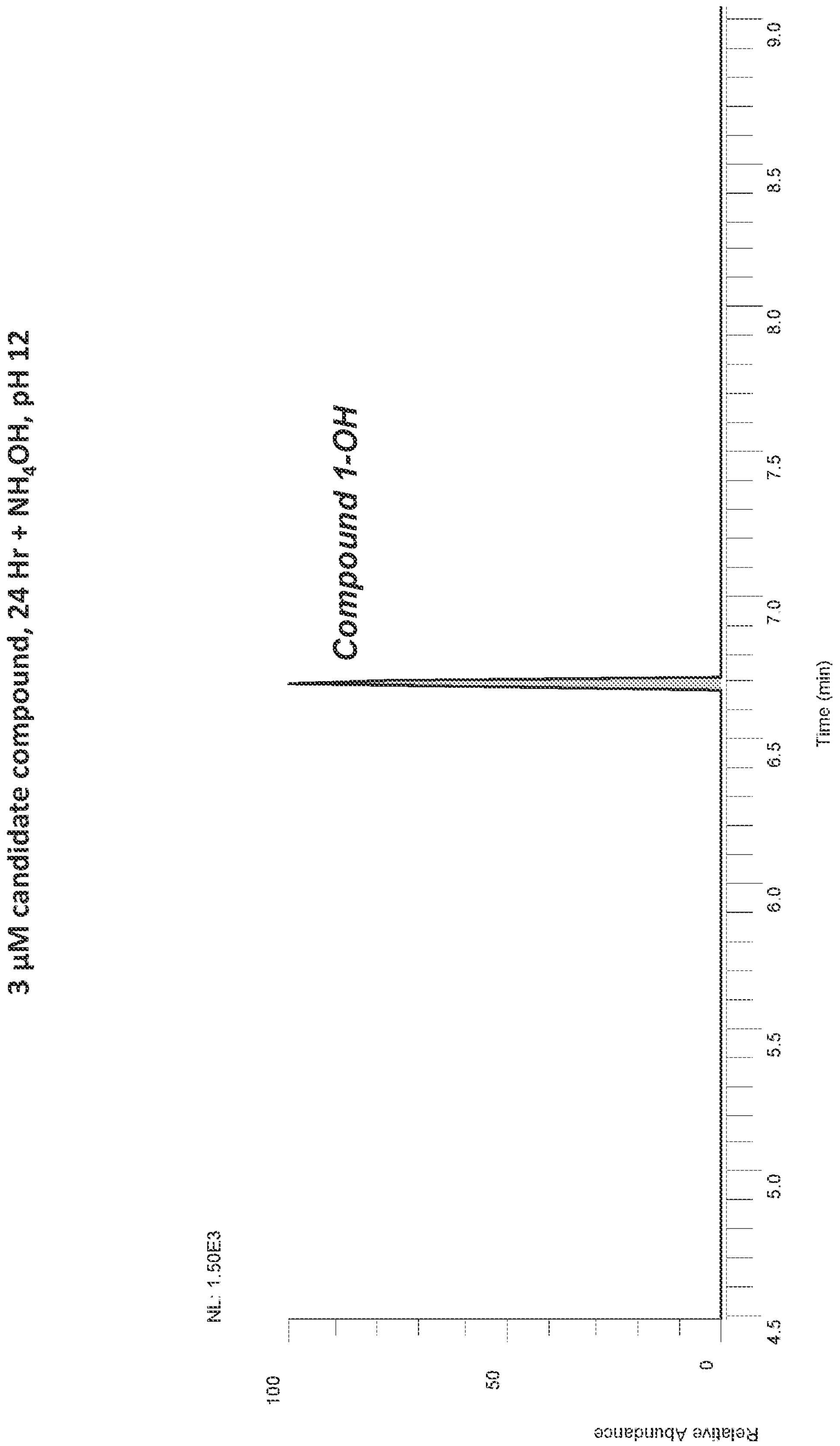

This difference in the Compound 1-Cl molecule and the Compound 1-OH molecule was distinguishable by mass spectrometry. As shown in FIG. 16A, the Compound 1-Cl molecule (i.e., in this example, the candidate compound attached to a binding moiety) showed an elution peak at approximately 7.375 minutes. In contrast, as shown in FIG. 16B, the Compound 1-OH molecule (i.e., in this example, the candidate compound attached to a releasing moiety) showed an elution peak at approximately 6.7 minutes. This shift in peaks showed that the method described herein was able to identify Compound 1 (i.e., a candidate compound not attached to either a binding moiety or a releasing moiety) as a compound that is able to traverse the cell membrane of an animal cell.

Example 3

In this Example 3, the methods described in Examples 1 and 2 were repeated to determine if multiple candidate compounds could be tested at the same time to see if one or more of them were able to traverse the cell membrane of an animal cell.

For these studies, human 293F suspension cells (FreeStyle™ 293-F cells commercially available from ThermoFisher Scientific, Waltham, MA) were used. These cells were seeded in Erlenmeyer Flasks with baffled bottom (Nalgene™ Single-Use PETG Erlenmeyer Flasks with Baffled Bottom: Sterile) and cultured in FreeStyle™ 293 Expression Media, and transfected using standard method Next, the PEG2-containing media was removed, and replaced with fresh media. The cells were then treated with media containing either DMSO or the ten chloroalkane-peptides that were being tested for an ability to traverse the cell membrane for 24 hours incubation. Note that in this Example 3, the ten peptides (i.e., candidate compounds) were either added individually (i.e., 1 uM of one distinct peptide per well), or were added to the same group of cells at the same time in a multiplexing method (i.e., 1 uM of each distinct peptide, for a total of 10 uM of peptides at the same time). The ten candidate compounds tested in this example were as follows: Compound 1 (control), Compound 2, Compound 3, Compound 4, Compound 5, Compound 6, Compound 7, Compound 8, Compound 9, and Compound 10.

After 24 hours of incubation, the media fraction and the cell fraction were collected from the control plates, the plates with only one distinct candidate compound, and the multiplexed plates with 10 distinct candidate compounds as follows:

For the Media fraction, 50 ul of cell culture media (i.e., conditioned media) from each sample was collected and transferred to a tissue culture plate that has low binding to protein (e.g., the protein Lo-Bind plate sold by Eppendorf).

For the cellular fraction, the tissue culture plate containing cells was centrifuged, followed by removed of most of the supernatant. Cells were then resuspended in 100 ul of residual media and transferred to a 96 well V-bottom plate. The plate was centrifuged, followed by removal of all supernatant. The cell pellets were subjected to a series of washes, with first fetal bovine serum (Heat Inactivated, complete FBS) and media, second phosphate buffered saline (PBS) and third with trypsin followed by quenching with media. The sequential washes were done to remove any residual peptide that may be loosely connected to the external cell membrane but is not internalized by the cell. The trypsin-media-cell suspension was transferred into a new tissue culture plate. An equal volume of ammonium hydroxide base was added to the resuspended cells. The cell mixture with ammonium hydroxide, which had a pH of 12.0, was then returned to the 37° C. incubator (shaking at 300 rpm) for 1 hour. During this 1-hour incubation, the cells underwent base hydrolysis.

Following base hydrolysis, the cell samples were dried in a SpeedVac (e.g., commercially available from ThermoFisher Scientific) overnight.

The following day, the dried sample was resuspended in 50 ul PBS to create the final cellular fraction. This final cellular fraction was then transferred to a protein Lo-Bind plate.

Next, 100 ul of chilled methanol 1% FA formic acid was added to both the media fractions. (Note that the 1% formic acid was chilled to 4° C., as the cold solution improves the separation of the cell and media fractions, as well as the extraction of the cellular content.) The final cellular fractions (each fraction in protein Lo-Bind plates), and the plate was stored at −20° C. for 4-5 hours to release the proteins and peptides from each of the fractions. The plates were then removed from −20° C. and their contents analyzed by mass spectrometry to look specifically for starting peptide in the media fraction and its base hydrolyzed analog in the cellular fraction.

Figure 17A:
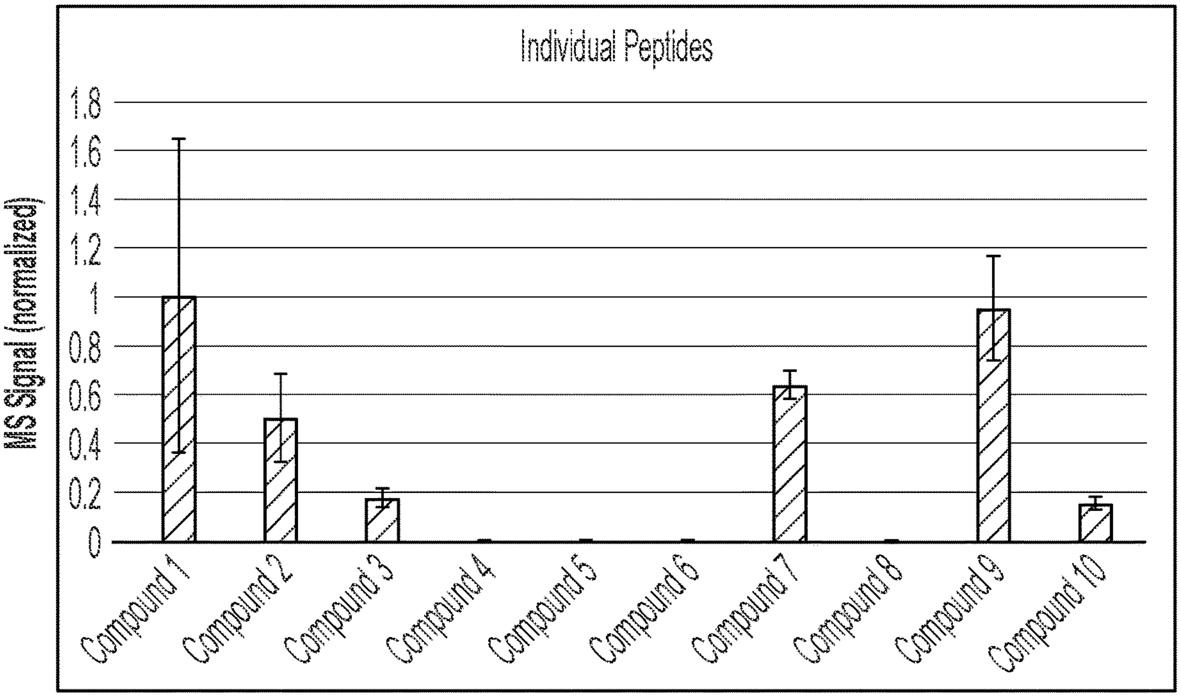
FIGS. 17A and 17B are bar graphs showing the cytosolic exposure (i.e., cytosolic presence) of the Candidate Compounds 2-10, all of which are stapled peptides, normalized to positive control stapled peptide Compound 1 as determined following testing of each compound individually (FIG. 17A) or together simultaneously (FIG. 17B).
Figure 17B:
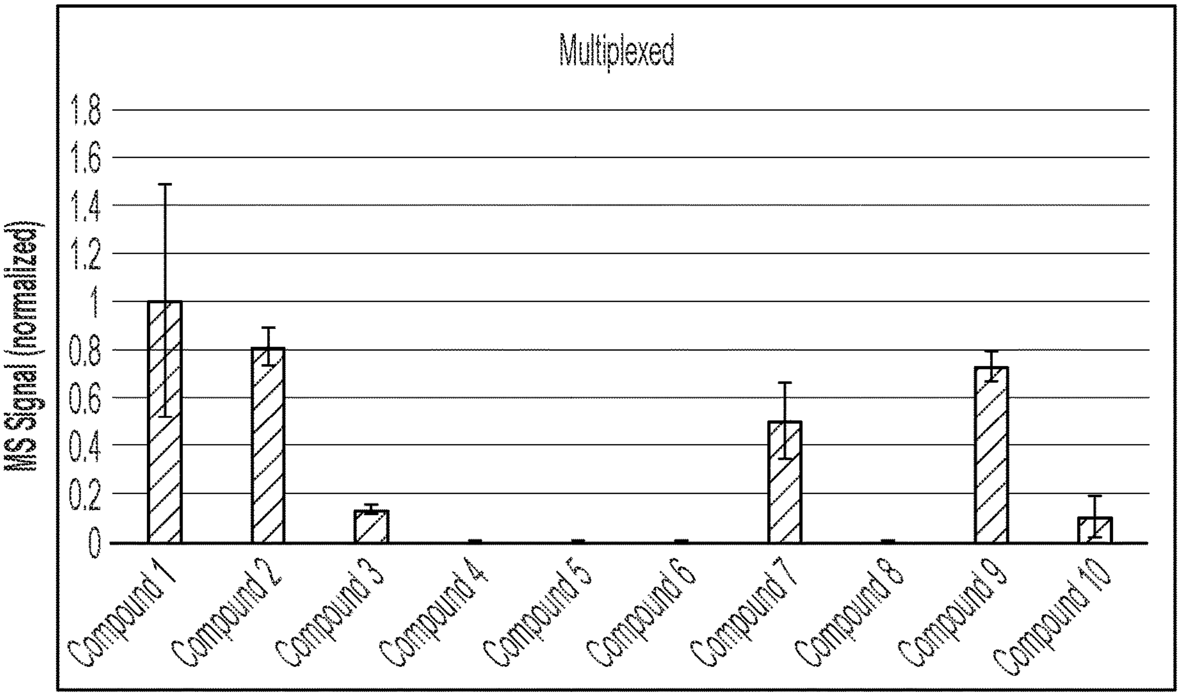

The results showed that the methods described in Examples 1 and 2 were replicable for the ten candidate compounds tested individually and together in a multiple method. FIGS. 17A and 17B show, in terms of an MS signal, the amount of a particular peptide that was found to be attached to the releasing moiety (i.e., attached to an —OH instead of a —Cl in this example. Note that data in FIGS. 17A and 17B is normalized to positive control Compound 1 described in Example 2 that was shown to be able to traverse the cell membrane (see FIGS. 14A-14B and data not shown). The data show that the cytosolic exposure patterns of the ten tested peptides is the very similar regardless of whether the peptides were tested individually (FIG. 17A) or together in a multiplex (FIG. 17B). Note that Compounds 2, 7, and 9 were able to cross the cell membrane almost as well as control Compound 1. These spectra of these three compounds (and the other compounds as well) can be further reviewed to identify the amino acid sequence according to standard mass spectrometry sequencing methods or by Edman degradation sequencing.

Example 4

In this prophetic example, human Jurkat T cells are obtained from the ATCC and transfected with an expression vector encoding HalogTag such that the transfected cells will constitutively express the HaloTag protein. For example, the Jurkat cells can be transfected (e.g., by electroporation or lipofectin) with the pHTC HaloTag CMV-neo Vector (G7711) or the PFC14A HaloTag CMV Flexi Vector (G9651), both of which are sold by Promega.

Following transfection (which may be transient or, in the case the pHTC HaloTag CMV-neo Vector is used, stable in cells grown in the presence of G418), cells expressing HaloTag protein are identified (e.g., by Western blotting of Jurkat cell lysates using an anti-HaloTag antibody such as the antibody sold as catalog no. G9211 by Promega).

The cells expressing HaloTag are next incubated in cell culture media containing 256 distinct candidate compounds each attached to a binding moiety, where each binding moiety contains a chloroalkane linker.

In other words, 256 distinct candidate compounds can be screened at the same time (e.g., in a multiplex screening assay) to identify those distinct candidate compounds that are able to traverse an animal cell membrane.

It should be noted that multiple copies of each candidate compound may be added to the HaloTag expressing cells. For example, if there are 256 distinct candidate compounds being screened that the same time, the cells may be incubated with 10,000 copies of each of the 256 distinct candidate compounds (i.e., with 2,560,000 compounds), where each candidate compound is covalently attached to a binding moiety that includes a chloroalkane linker.

In this prophetic example, 256 distinct candidate compounds will be screened. Each of the 256 distinct candidate compounds, each attached to a binding moiety, will be analyzed by mass spectrometry and their data retained.

The cells will be incubated in culture media (e.g., RPMI 1640) containing the candidate compounds, each attached to a binding moiety, for a time sufficient for those compounds that are able to traverse the cell membrane to traverse the cell membrane form a complex with the HaloTag via the binding moiety within the cytoplasm of the cell. While this time may vary, according to the cell type, the time may be discerned using routine techniques.

Following this incubation time, the culture media will be removed and can be discarded since mass spectrometry analysis has already been performed on the candidate compounds attached to binding moieties prior to adding these to the culture media.

The cells will then be lysed in base hydrolysis by changing the pH to 11.0 or higher (e.g., a pH of 12.0). The complex that includes the HaloTag covalently attached to at least part of the binding moiety attached to the candidate compound will be disrupted also by the base hydrolysis, and those candidate compounds freed (i.e., detached) from the complex will have a releasing moiety attached to them instead of a binding moiety.

Each distinct candidate compound from the lysed cells can be analyzed by mass spectrometry to detect the presence of the releasing moiety attached to the candidate compound. Each distinct candidate compound attached to a releasing molecule can be identified by comparing its mass spectrometry spectrum to the mass spectrometry spectrum of the starting candidate compounds, each attached to a binding moiety.

In this manner, 256 candidate compounds can be screened for their abilities to traverse the cell membrane of a non-adherent animal cell at the same time.

Example 5

Animal cells (e.g., Expi293 cells or human HEK 293 cells) were seeded in tissue culture plates and cultured in Opti-MEM media. The cells were set in PETG flasks at a concentration of $6\times10^5$ cells/mL and a volume of 30 mL. The cell viability was checked to be above 90-93%. Two flasks containing Expi293 cells were prepared, one for control and one for halotag transfection. The flasks were placed in a shaking incubator at 300 rpm in 8% $CO_2$.

After 24 hours of incubation, four 2-mL Lo-Bind tubes were prepared, wherein tube 1a contained 100 μL of Opti-MEM, tube 2a contained 10 μL (30 μg) of halotag plasmid in 990 μL of Opti-MEM, and tubes 1b and 2b each contained 60 μL of ExpiFectamine 293 in 940 μL of Opti-MEM, which was incubated at room temperature for 5 minutes. The mixture in tube 1a was added to tube 1b, and the mixture in tube 2a was added to tube 2b. The combined mixtures were incubated at room temperature for 20 minutes, and subsequently added to cells. The cells were placed in a shaking incubator for 72 hours, during which the media was not changed.

After 48 hours of transfection, the transfected cells were checked for viability (90% or higher). The transfected cells were transferred to a protein Lo-Bind Eppendorf 96-well deep well plate (1000 μL), where each well contained 1 million cells in 500 μL of Expi293 media. A 2 μM solution of PEG2 (linker molecule containing chloroalkane tag) was prepared. 500 μL of the PEG2 solution was added to each well. The 96-well plate was placed in a shaking incubator for 2 hours. Following incubation, the plate was placed in a centrifuge at 300 g for 5 minutes. 850 μL of the supernatant was removed without disturbing the cell pellet. If it is not easy to remove media from the plate after the final spin, 800 μL of the supernatant was removed instead. The cells were resuspended in the residual media (200 μL), and the suspension was transferred to a v-bottom 96-well plate. The v-bottom plate was placed in a centrifuge at 300 g for 5 minutes. All residual media was subsequently removed. The cells were resuspended in 200 μL of fresh media. The suspension was transferred to a new 96-well deep well plate. Another 300 μL of media was added and the cells were let rest.

Solutions of a new set of candidate compounds (compounds 1-30) from a peptide library were diluted to 20 μM. 500 μL of each candidate compound solution was added in duplicates to the 96-well plate, resulting in a final concentration of 10 μM of each candidate compound in a single well. Each well further contained a positive and a negative control. For counting wells, 500 μL of plain media was added. The cells were kept in a shaking incubator at 300 rpm, 8% $CO_2$ overnight for about 18-20 hours.

The following day, the 96-well plate was placed in the centrifuge at 300 g for 5 minutes. For the media fraction, 50 μL of media was transferred to a Lo-Bind 96-well deep well Eppendorf plate (500 μL).

For the cellular fraction, the 96-well plate was placed in the centrifuge at 300 g for another 5 minutes. 750 μL of the supernatant was removed. The cells were resuspended in residual 200 μL of media. The suspensions were transferred to a 96-well v-bottom plate, which was placed in the centrifuge at 300 g for an additional 5 minutes. All remaining media was removed. The cell pellets were subjected to a series of washes, with first fetal bovine serum (Heat Inactivated, complete FBS) and media, second phosphate buffered saline (PBS) and third with trypsin followed by quenching with media. The plate was centrifuged, followed by removal of all supernatant. The cell pellets were subjected to a series of washes, with first fetal bovine serum (Heat Inactivated, complete FBS) and media, second phosphate buffered saline (PBS) and third with trypsin followed by quenching with media. The sequential washes were done to remove any residual peptide that may be loosely connected to the external cell membrane but is not internalized by the cell. The trypsin-media-cell suspension was transferred into a new tissue culture plate. An equal volume of ammonium hydroxide base was added to the resuspended cells. The cell mixture with ammonium hydroxide, which had a pH of 12.0, was then returned to the 37° C. incubator (shaking at 300 rpm) for 1 hour. During this 1-h incubation, the cells underwent base hydrolysis.

Following base hydrolysis, the cell samples were dried in a SpeedVac (e.g., commercially available from ThermoFisher Scientific) overnight.

The following day, the dried sample was resuspended in 50 μL of PBS to create the final cellular fraction. This final cellular fraction was then transferred to a protein Lo-Bind plate. 100 μL of chilled methanol/1% formic acid (FA) was subsequently added to both the media fractions, (note: the 1% formic acid was chilled to 4° C., as the cold solution improves the separation of the cell and media fractions, as well as the extraction of the cellular content.) and the final cellular fractions (each fraction in protein Lo-Bind plates). The plates were stored at 4° C. for 24 hours or at −20° C. for 4-5 hours to release the proteins and peptides from each of the fractions. The plates were placed in a centrifuge cooled to 4° C. at 4000 rpm for 8-10 minutes. Approximately 90 μL of the solution was transferred to a Greiner 96-well plate, which was kept at 4° C. and sealed, and placed in the autosampler of a mass spectrometer. In some embodiments, samples may optionally be mixed with certain additives to ensure stability of samples and.or prevent degradation or loss of samples to, e.g., plastic binding. Useful additives include proteins such as BSA, defatted milk powder, peptides or mixtures of peptides, mass-spectrometry compatible detergents, DMSO, and guanidinium hydrochloride.

Certain data were presented in the Table below. Numbers are MS ion intensity. Administered agents comprising —Cl (FG2) are converted into product agents comprising —OH (FG3, which replaces —Cl).

Cell free OH (Agents comprising halotag substrate (-L-Cl) were mixed with an enzyme (e.g., DhaA, aka Haloalkane dehalogenase, from *Rhodococcus rhodochrous*) that converts —Cl to —OH catalytically in vitro. Among other things, this may provide what the theoretical 100% signal should be for each agent in its —OH form. Such sample may be used as "input" to normalize values observed, e.g., in cells, as some agents, e.g., library/pool members, may be presented at different starting levels):

| Compound | N = 1 (Run 1) | N = 2 (Run 2) | N = 2 SD | N = 1 SD |
|---|---|---|---|---|
| Cpd 1 | 22669496 | | | 1139809 |
| Cpd 2 | 13333718 | 13348164 | 1163851 | 327869.3 |
| Cpd 3 | 12988804 | 9486974 | 1894026 | 445196.2 |
| Cpd 4 | 43986601 | 51465808 | 21338607 | 61711.4 |
| Cpd 5 | 19092224 | 17302050 | 6253285 | 319588.6 |
| Cpd 6 | 17657923 | 21245422 | 9791648 | 538552.3 |
| Cpd 7 | 11775348 | 14992090 | 5657798 | 955589.8 |
| Cpd 8 | 16466203 | 12780067 | 1913383 | 602150.2 |
| Cpd 9 | 14024522 | 20313249 | 5620877 | 2792768 |
| Cpd 10 | 11304067 | 13738733 | 5455465 | 250871.7 |
| Cpd 11 | 16437924 | 21733517 | 8639816 | 442227.3 |
| Cpd 12 | 17105893 | 15612482 | 887465.9 | 121095.4 |
| Cpd 13 | 13723501 | 13390849 | 5194529 | 267688.9 |
| Cpd 14 | 19972396 | 21162630 | 276960.4 | 709325.5 |
| Cpd 15 | 18256272 | 22693264 | 1238967 | 889369 |
| Cpd 16 | 3475501 | 2905029 | 99030.4 | 206122.5 |
| Cpd 17 | 18546916 | 17764908 | 1095409 | 1326646 |
| Cpd 18 | 10870355 | 10061169 | 306262 | 752641.3 |
| Cpd 19 | 8958926 | 9521273 | 840546.5 | 171304 |
| Cpd 20 | 13030452 | 10663373 | 1588017 | 785188.5 |
| Cpd 21 | 14970390 | 14349758 | 696227.5 | 800765.4 |
| Cpd 22 | 18054760 | 20094631 | 155283.9 | 1465630 |
| Cpd 23 | 14951853 | 18242932 | 375379.1 | 1236508 |
| Cpd 24 | 13335461 | 15733276 | 765784.4 | 502764.9 |

-continued

| Compound | N = 1 (Run 1) | N = 2 (Run 2) | N = 2 SD | N = 1 SD |
|---|---|---|---|---|
| Cpd 25 | 15599151 | 13360556 | 489052.9 | 704258.5 |
| Cpd 26 | 16518694 | 18832043 | 4992190 | 1422833 |
| Cpd 27 | 23660206 | 23485792 | 1011866 | 832035.4 |
| Cpd 28 | 20471984 | 19664419 | 294799.5 | 700416.9 |
| Cpd 29 | 15328794 | 15592006 | 679159.2 | 849901.6 |
| Cpd 30 | 18294335 | 15535973 | 829279.9 | 1479937 |

Cell OH (Ion signal of —OH containing product agents found in cells. In some embodiments, COR equals Cell OH divided by Cell free OH. In some embodiments, RPF is similarly calculated but also uses positive and negative controls to normalize data):

| Compound | N = 1 (Run 1) | N = 2 (Run 2) | N = 2 SD | N = 1 SD |
|---|---|---|---|---|
| Cpd 1 | 2446285 | | | 256649.5 |
| Cpd 2 | 1715910 | 1896482 | 673579 | 130439.6 |
| Cpd 3 | 396587.3 | 735852.8 | 89681.6 | 98941.6 |
| Cpd 4 | 8067345 | 7513427 | 1296164 | 1060534 |
| Cpd 5 | 1098771 | 2167341 | 56506.5 | 86030.8 |
| Cpd 6 | 1499607 | 2315526 | 636956 | 231702.9 |
| Cpd 7 | 1021688 | 874979.1 | 814528.1 | 156363.1 |
| Cpd 8 | 837882.1 | 664583.6 | 239293.2 | 60734.8 |
| Cpd 9 | 1000324 | 1915857 | 189446.2 | 185146.1 |
| Cpd 10 | 417410.7 | 1327339 | 199895.9 | 91122.4 |
| Cpd 11 | 688822.3 | 1211493 | 195237.1 | 67071 |
| Cpd 12 | 737427.4 | 1655671 | 532593.4 | 64151.9 |
| Cpd 13 | 941692.6 | 2020378 | 190453.7 | 173255.4 |
| Cpd 14 | 1882705 | 1752580 | 709193.8 | 145777.7 |
| Cpd 15 | 2103937 | 5325080 | 885198.8 | 206284.9 |
| Cpd 16 | 512461.8 | 553158.9 | 146576.8 | 45937.4 |
| Cpd 17 | 1989114 | 2227911 | 693954 | 380338.8 |
| Cpd 18 | 1171599 | 1469398 | 247423.4 | 30756.9 |
| Cpd 19 | 813729.9 | 531355.2 | 110312 | 19732.3 |
| Cpd 20 | 1224001 | 1093078 | 254786.1 | 107814.2 |
| Cpd 21 | 327109.7 | 1990173 | 325483.1 | 101169.8 |
| Cpd 22 | 1480678 | 2080071 | 306314.8 | 260541.9 |
| Cpd 23 | 360683.6 | 1426248 | 344555 | 63819.4 |
| Cpd 24 | 923573.6 | 1300506 | 150578 | 14405.7 |
| Cpd 25 | 1830807 | 3762960 | 787375.6 | 223164 |
| Cpd 26 | 1556570 | 2513540 | 441413.4 | 95731.6 |
| Cpd 27 | 1236493 | 2072587 | 624449 | 129293.2 |
| Cpd 28 | 1015868 | 2624706 | 798576.2 | 92036.1 |
| Cpd 29 | 1711889 | 2238678 | 623885.5 | 186774.4 |
| Cpd 30 | 3027038 | 2579181 | 497844.6 | 344387.4 |

In some embodiments, percentage of product agent over tested agent (e.g., cell OH over Cell Free OH) is calculated and utilized to assess permeability of tested agent. In some embodiments, RPF is utilized. In some embodiments, COR is utilized. Certain data were presented below using data above (for RPF, negative data not shown):

RPF:

| Compound | N = 1 | N = 2 | RPF_sd N = 2 | RPF_sd (N = 1) |
|---|---|---|---|---|
| Cpd 1 | 0.31 | | | 0.05 |
| Cpd 2 | 0.48 | 0.29 | 0.07 | 0.11 |
| Cpd 3 | 0.07 | 0.11 | 0.06 | 0.02 |
| Cpd 4 | 0.48 | 0.22 | 0.10 | 0.21 |
| Cpd 5 | 0.07 | 0.16 | 0.07 | 0.01 |
| Cpd 6 | 0.15 | 0.16 | 0.04 | 0.10 |
| Cpd 7 | 0.18 | 0.18 | 0.17 | 0.10 |
| Cpd 8 | 0.15 | 0.14 | 0.08 | 0.03 |
| Cpd 9 | 0.15 | 0.10 | 0.03 | 0.06 |
| Cpd 10 | 0.05 | 0.13 | 0.05 | 0.03 |
| Cpd 11 | 0.09 | 0.06 | 0.01 | 0.03 |
| Cpd 12 | 0.18 | 0.14 | 0.02 | 0.09 |
| Cpd 13 | 0.16 | 0.19 | 0.02 | 0.07 |
| Cpd 14 | 0.27 | 0.12 | 0.03 | 0.04 |

-continued

| Compound | N = 1 | N = 2 | RPF_sd N = 2 | RPF_sd (N = 1) |
|---|---|---|---|---|
| Cpd 15 | 0.48 | 0.27 | 0.07 | 0.23 |
| Cpd 16 | 0.56 | 0.17 | 0.06 | 0.15 |
| Cpd 17 | 0.31 | 0.22 | 0.05 | 0.05 |
| Cpd 18 | 0.33 | 0.15 | 0.04 | 0.07 |
| Cpd 19 | 0.22 | 0.10 | 0.01 | 0.04 |
| Cpd 20 | 0.34 | 0.10 | 0.04 | 0.03 |
| Cpd 21 | 0.07 | 0.16 | 0.03 | 0.03 |
| Cpd 22 | 0.32 | 0.12 | 0.03 | 0.02 |
| Cpd 23 | 0.08 | 0.10 | 0.02 | 0.01 |
| Cpd 24 | 0.20 | 0.09 | 0.01 | 0.06 |
| Cpd 25 | 0.40 | 0.44 | 0.08 | 0.06 |
| Cpd 26 | 0.36 | 0.09 | 0.01 | 0.13 |
| Cpd 27 | 0.15 | 0.11 | 0.02 | 0.05 |
| Cpd 28 | 0.13 | 0.17 | 0.06 | 0.02 |
| Cpd 29 | 0.58 | 0.30 | 0.05 | 0.17 |
| Cpd 30 | 0.83 | 0.43 | 0.03 | 0.12 |

COR:

| Compound | N = 1 | N = 2 | COR SD MM | COR SD BG |
|---|---|---|---|---|
| Cpd 1 | 0.89 | | | 0.10 |
| Cpd 2 | 0.78 | 1.05 | 0.18 | 0.12 |
| Cpd 3 | 0.14 | 0.38 | 0.05 | 0.03 |
| Cpd 4 | 3.18 | 3.02 | 0.22 | 0.31 |
| Cpd 5 | 0.33 | 0.59 | 0.03 | 0.05 |
| Cpd 6 | 0.56 | 0.78 | 0.17 | 0.18 |
| Cpd 7 | 0.33 | 1.63 | 0.81 | 0.05 |
| Cpd 8 | 0.32 | 0.67 | 0.27 | 0.03 |
| Cpd 9 | 0.34 | 1.01 | 0.19 | 0.03 |
| Cpd 10 | 0.15 | 0.45 | 0.04 | 0.02 |
| Cpd 11 | 0.26 | 0.50 | 0.09 | 0.01 |
| Cpd 12 | 0.38 | 0.57 | 0.05 | 0.15 |
| Cpd 13 | 0.36 | 0.66 | 0.11 | 0.09 |
| Cpd 14 | 0.91 | 0.79 | 0.19 | 0.05 |
| Cpd 15 | 1.13 | 1.37 | 0.19 | 0.47 |
| Cpd 16 | 0.24 | 0.17 | 0.03 | 0.05 |
| Cpd 17 | 0.89 | 1.94 | 0.53 | 0.05 |
| Cpd 18 | 0.48 | 0.93 | 0.03 | 0.01 |
| Cpd 19 | 0.35 | 0.33 | 0.05 | 0.01 |
| Cpd 20 | 0.55 | 0.43 | 0.07 | 0.07 |
| Cpd 21 | 0.17 | 0.70 | 0.13 | 0.04 |
| Cpd 22 | 0.72 | 0.66 | 0.11 | 0.02 |
| Cpd 23 | 0.17 | 0.53 | 0.10 | 0.01 |
| Cpd 24 | 0.42 | 0.33 | 0.01 | 0.06 |
| Cpd 25 | 1.01 | 1.46 | 0.20 | 0.13 |
| Cpd 26 | 0.73 | 1.18 | 0.16 | 0.15 |
| Cpd 27 | 0.59 | 0.65 | 0.08 | 0.11 |
| Cpd 28 | 0.38 | 0.84 | 0.28 | 0.02 |
| Cpd 29 | 0.88 | 1.05 | 0.21 | 0.25 |
| Cpd 30 | 1.57 | 1.37 | 0.09 | 0.12 |

Example 6

Among other things, provided technologies can provide high efficiency. In some embodiments, the provided technologies can provide high-throughput assessment of pluralities of agents. For example, in some embodiments, crude library products comprising multiple member agents may be assessed in a single system, e.g., a single well, as described herein.

Animal cells (e.g., Expi293 cells or human HEK 293 cells) were seeded in tissue culture plates and cultured in Opti-MEM media. The cells were set in PETG flasks at a concentration of $6\times10^5$ cells/mL and a volume of 30 mL. The cell viability was checked to be above 90-93%. The flasks were placed in a shaking incubator at 300 rpm in 8% $CO_2$.

After 24 hours of incubation, for each flask, one 1.5-mL Lo-bind tube and one 2-mL Lo-Bind tube were prepared. In the 1.5-mL tube, 30 μg of polyhistidine-tagged halotag (His-Halotag) plasmid and Opti-MEM media were added to provide a 1-mL mixture. In the 2-mL Lo-Bind tube, 60 μL of ExpiFectamine and 940 μL of Opti-MEM were added. After 5 minutes, the plasmid/Opti-MEM mixture was added to the ExpiFectamine/Opti-MEM mixture. The combined mixture was placed in an incubator at room temperature for 20 minutes, which was subsequently added to the flask.

After 48 hours of transfection, the transfected cells were checked for viability (90% or higher). The transfected cells were transferred to a protein Lo-Bind Eppendorf 96-well deep well plate (1000 μL), where each well contained 1 million cells in 500 μL of Expi293 media.

Solutions of candidate compounds, either individual peptides or peptides from a peptide library (DPLs), were received at a stock concentration of 10 mM and diluted in DMSO and kept in a "Source Plate". For DPLs, the peptide concentration in the "Source Plate" was 1 mM, whereas for individual peptides, the concentration was either 100 μM (for a final concentration of 100 nM) or 10 μM (for a final concentration of 10 nM). 500 μL of the DPL or individual peptide solution was added in triplicates to the 96-well plate. The cells were kept in a shaking incubator at 300 rpm and 37° C., 8% $CO_2$ overnight for about 18-20 hours.

The following day, one of the following two methods was performed: i) capture beads method or ii) cell crash method.

Capture beads method: the 96-well plate was placed in the centrifuge at 300 g for 5 minutes. 720 μL of the supernatant was removed. The cells were resuspended in residual 200 μL of media. The suspensions were transferred to a 96-well v-bottom plate, which was placed in the centrifuge at 300 g for an additional 5 minutes. All remaining media was removed. The cell pellets were washed with 200 μL of PBS, mixed and placed back in the centrifuge at 300 g and 4° C. for an additional 5 minutes. The supernatant was removed. 100 μL of 5 μM HaloTag TMR ligand (HaloTag® TMR Ligand (555Ex/585Em) from Promega: Cat #: G825A was added to each well. The plate was placed in a shaking incubator at 300 rpm and 37° C., 8% $CO_2$ for 30 minutes. The cells were then washed with 200 μL of PBS twice, mixed, and placed back in the centrifuge at 300 g and 4° C. for an additional 5 minutes. Cold lysis buffer (EasyPep™ Lysis Buffer with a 100× of protease inhibitor without EDTA, 0.1 μL/mL of Thermofisher universal nuclease) was prepared. 200 μL of lysis buffer was added to each well and the samples were transferred to a KingFisher DeepWell plate (1000 μL). Additional 300 μL of lysis buffer was added. The mixture was kept at 4° C. in a cold room to shake for 20-30 minutes.

The following protocol was used for KingFisher purification.

Seven plates were prepared as follows: (i) Tip Plate (plate type 96 standard plate), (ii) His magnetic bead plate (plate type 96 standard plate), which contained 50 μL of His beads (Dynabeads His-Tag Isolation & Pulldown (Invitrogen by thermofisher REF10104D)) in each sample well, (iii) His bead wash plate (plate type 96 standard plate), with 100 μL of lysis buffer without PI/nuclease in each sample well, (iv) Halo His Lysis plate (plate type 96 deep well plate), containing 500 μL of the cell lysate, (v) Bead Wash plate I (plate type 96 standard plate), containing 100 μL of wash buffer I(HEPES pH 7.5+200 mM NaCl), (vi) Bead Wash plate II (plate type 96 standard plate), containing 100 μL of Wash Buffer II (HEPES pH 7.5+200 mM NaCl), and (vii) Bead Elution Plate (plate type 96 standard plate), containing 100 μL of Elution Buffer (HEPES pH 7.5+150 mM imidazole). Each plate was loaded, as directed by KingFisher. The purification process began, once all 7 plates were loaded. Upon collection of the eluate, all plates were removed from the instrument.

Cell crash method: the 96-well plate was placed in the centrifuge at 300 g for 5 minutes. 720 μL of the supernatant was removed. The cells were resuspended in residual 200 μL of media. The suspensions were transferred to a 96-well v-bottom plate, which was placed in the centrifuge at 300 g for an additional 5 minutes. All remaining media was removed. The cell pellets were washed with 200 μL of PBS, mixed and placed back in the centrifuge at 300 g and 4° C. for an additional 5 minutes. The supernatant was removed and 80 μL of PBS was added.

80 μL of eluted proteins/peptides from the capture beads method or the PBD solution from the cell crash method was transferred into a deepwell low binding plate (500 μL). 80 μL of ammonium hydroxide was added. The plate was kept on a shaker at 37° C. for 3 hours. The plate was dried in a speedvac overnight.

The following day, the dried cell pellet was resuspended in 70 μL of 47.5% water with 0.1% FA/47.5% ACN with 0.1% FA/10 μM pepmix (10 mM stock)/5% fresh DMSO. The mixture was let sit in the plate for 1 hour to allow the dissolution of the pellet. If the sample appeared cloudy, more resuspension solution was added (50 μL at a time). 50 μL was transferred directly to the mass spec plate and the plate was sealed with the 384-well plate seal.

For the cell free systems, DPLs were diluted in a 500 μL DPW plate (library dilution plate). Individual peptides were diluted individually in low-bind tubes until making the final working dilution in PBS. At this point, the individual peptides were transferred to the library dilution plate. By having all final dilutions in one plate, a multichannel was used to transfer the diluted peptides to the cell free plates. The same design as "Source Plate" was used for the cell assay. For the peptide only plate, 45 μL of PBS was added to each well and 5 μL of the diluted library/peptide was added in triplicates. For peptide/DhaA plate, 5 μL of 50 μM DhaA enzyme was added, followed by 40 μL of PBS and 5 μL of the diluted library/peptide. Both plates were kept at the bench top thermomixer at 350 rpm and 37° C. overnight. The next day, 2 mL of a cell free solution was prepared with 1 mL of DMSO, 20 μL of PepMix and 980 μL of a 1:1 ratio of ACN/0.1% FA and $H_2O$/0.1% FA. 5 μL of the cell free solution was added to a 384 well plate, followed by 45 μL of the cell free sample.

Once all samples were added (including cell free), the plate was placed in an autosampler of a mass spectrometer. For the mass spectrometry analysis, methods from example 1 were employed.

Results from certain assessment were presented blow. Cell crash method was utilized. Mass Shifted Peptide Theoretical Max signal is signal of an agent comprising —OH obtained when using the DhaA to convert input agent comprising —Cl into product agent comprising —OH form without involving cells (multiple agents may be converted simultaneously; in some embodiments, can be performed library by library). In some embodiments, each library pool plus positive and negative references was tested in a single well, which in some cases contain about a million or so cells. Each library pool is an individually prepared library with no purifications—all members mixed together along with side products, etc. "Cell Penetration Score" is calculated by dividing "Mass Shifted Peptide Signal in Cells" by "Mass Shifted Peptide Theoretical Max Signal" for each pair of replicates, then averaging those values across replicates; additionally or alternatively, COR and/or RPF may also be utilized.

| Peptide | B | C | D | E | F | G | H | I | J | K | L | M | N |
|---|---|---|---|---|---|---|---|---|---|---|---|---|---|
| PEP000001 | 329 | 3E+06 | 4E+05 | 1E+07 | 9E+05 | 295 | 8E+04 | 4E+06 | 9E+05 | Library | A | 1298 | NA |
| PEP000002 | 335 | 5E+06 | 8E+05 | 4E+06 | 3E+05 | 300 | 2E+06 | 9E+05 | 4E+05 | Library | A | 50 | 29 |
| PEP000003 | 333 | 7E+06 | 1E+06 | 3E+07 | 2E+06 | 299 | 3E+06 | 8E+06 | 2E+06 | Library | A | 262 | 87 |
| PEP000004 | 339 | 1E+07 | 1E+06 | 2E+07 | 2E+06 | 304 | 5E+06 | 9E+06 | 2E+06 | Library | A | 191 | 60 |
| PEP000005 | 336 | 5E+06 | 7E+05 | 1E+07 | 3E+05 | 302 | 2E+06 | 5E+06 | 1E+06 | Library | A | 229 | 48 |
| PEP000006 | 340 | 1E+06 | 4E+05 | 3E+05 | 2E+04 | 305 | 0E+00 | 6E+03 | 1E+04 | Library | A | NA | NA |
| PEP000007 | 332 | 2E+06 | 3E+05 | 8E+05 | 5E+05 | 296 | 4E+05 | 6E+04 | 3E+04 | Library | A | 13 | 6 |
| PEP000008 | 328 | 3E+06 | 5E+05 | 2E+07 | 1E+06 | 295 | 2E+06 | 4E+06 | 1E+06 | Library | A | 291 | 175 |
| PEP000009 | 335 | 6E+06 | 1E+06 | 1E+07 | 7E+05 | 301 | 3E+06 | 5E+06 | 7E+05 | Library | A | 193 | 27 |
| PEP000010 | 333 | 6E+06 | 9E+05 | 2E+07 | 1E+06 | 299 | 2E+06 | 6E+06 | 2E+06 | Library | A | 368 | 109 |
| PEP000011 | 340 | 8E+06 | 1E+06 | 2E+07 | 2E+06 | 305 | 4E+06 | 1E+07 | 2E+06 | Library | A | 273 | 64 |
| PEP000012 | 338 | 4E+06 | 5E+05 | 7E+06 | 4E+05 | 302 | 8E+05 | 2E+06 | 4E+05 | Library | A | 176 | NA |
| PEP000013 | 372 | 3E+05 | 4E+05 | 0E+00 | 0E+00 | 283 | 2E+05 | 0E+00 | 0E+00 | Library | B | 0 | NA |
| PEP000014 | 375 | 8E+05 | 8E+04 | 0E+00 | 0E+00 | 344 | 0E+00 | 2E+06 | 8E+04 | Library | B | NA | NA |
| PEP000015 | 385 | 2E+05 | 3E+05 | 0E+00 | 0E+00 | 353 | 0E+00 | 0E+00 | 0E+00 | Library | B | NA | NA |
| PEP000016 | 373 | 8E+05 | 6E+04 | 0E+00 | 0E+00 | 343 | 0E+00 | 2E+06 | 2E+05 | Library | B | NA | NA |
| PEP000017 | 381 | 1E+06 | 2E+05 | 5E+03 | 8E+03 | 349 | 3E+05 | 4E+06 | 3E+05 | Library | B | 815 | NA |
| PEP000018 | 365 | 2E+05 | 4E+05 | 0E+00 | 0E+00 | 318 | 0E+00 | 4E+04 | 5E+04 | Library | B | NA | NA |
| PEP000019 | 347 | 3E+06 | 2E+05 | 0E+00 | 0E+00 | 315 | 1E+06 | 5E+06 | 1E+06 | Library | B | 369 | 99 |
| PEP000020 | 354 | 5E+06 | 2E+05 | 0E+00 | 0E+00 | 321 | 2E+06 | 5E+06 | 1E+06 | Library | B | 224 | 54 |
| PEP000021 | 366 | 6E+06 | 1E+05 | 3E+04 | 2E+04 | 334 | 3E+06 | 8E+06 | 3E+06 | Library | B | 291 | 136 |
| PEP000022 | 353 | 6E+06 | 2E+05 | 5E+04 | 7E+04 | 319 | 2E+06 | 9E+06 | 2E+06 | Library | B | 357 | 95 |
| PEP000023 | 340 | 2E+06 | 2E+05 | 0E+00 | 0E+00 | 327 | 3E+05 | 2E+06 | 7E+05 | Library | B | 639 | 271 |
| PEP000024 | 346 | 3E+06 | 3E+05 | 0E+00 | 0E+00 | 313 | 1E+06 | 3E+06 | 9E+05 | Library | B | 250 | 74 |
| PEP000025 | 351 | 2E+04 | 4E+04 | 0E+00 | 0E+00 | 320 | 6E+05 | 1E+06 | 9E+05 | Library | B | 248 | 155 |
| PEP000026 | 357 | 4E+06 | 9E+04 | 1E+04 | 1E+04 | 325 | 2E+06 | 6E+06 | 2E+06 | Library | B | 363 | 100 |
| PEP000027 | 355 | 4E+06 | 1E+05 | 1E+04 | 1E+04 | 324 | 2E+06 | 5E+06 | 1E+06 | Library | B | 269 | 66 |
| PEP000028 | 361 | 7E+06 | 5E+04 | 3E+04 | 6E+04 | 328 | 3E+06 | 9E+06 | 3E+06 | Library | B | 301 | 106 |
| PEP000029 | 348 | 3E+06 | 2E+05 | 3E+03 | 5E+03 | 334 | 5E+05 | 1E+06 | 7E+05 | Library | B | 304 | 20 |
| PEP000030 | 438 | 9E+05 | 4E+03 | 0E+00 | 0E+00 | 403 | 6E+05 | 1E+07 | 2E+05 | Library | C | 1856 | 55 |
| PEP000031 | 460 | 4E+05 | 1E+05 | 0E+00 | 0E+00 | 437 | 0E+00 | 0E+00 | 0E+00 | Library | C | NA | NA |
| PEP000032 | 459 | 4E+05 | 1E+05 | 0E+00 | 0E+00 | 437 | 0E+00 | 0E+00 | 0E+00 | Library | C | NA | NA |
| PEP000033 | 433 | 1E+06 | 4E+04 | 0E+00 | 0E+00 | 394 | 4E+05 | 1E+07 | 2E+05 | Library | C | 1835 | NA |
| PEP000034 | 452 | 8E+05 | 1E+05 | 0E+00 | 0E+00 | 429 | 4E+05 | 4E+06 | 5E+05 | Library | C | 1135 | 121 |
| PEP000035 | 449 | 1E+06 | 1E+05 | 0E+00 | 0E+00 | 425 | 9E+05 | 2E+07 | 1E+06 | Library | C | 1908 | 184 |
| PEP000036 | 452 | 8E+05 | 7E+04 | 0E+00 | 0E+00 | 288 | 2E+05 | 2E+04 | 3E+04 | Library | C | 0 | NA |
| PEP000037 | 444 | 5E+05 | 3E+04 | 0E+00 | 0E+00 | 416 | 0E+00 | 4E+06 | 5E+04 | Library | C | NA | NA |
| PEP000038 | 438 | 6E+05 | 4E+04 | 0E+00 | 0E+00 | 405 | 0E+00 | 6E+06 | 6E+05 | Library | C | NA | NA |
| PEP000039 | 443 | 6E+05 | 6E+04 | 0E+00 | 0E+00 | 414 | 0E+00 | 4E+06 | 3E+05 | Library | C | NA | NA |
| PEP000040 | 436 | 1E+06 | 5E+04 | 0E+00 | 0E+00 | 399 | 9E+05 | 1E+07 | 9E+05 | Library | C | 1239 | 145 |
| PEP000041 | 458 | 6E+05 | 2E+05 | 0E+00 | 0E+00 | 434 | 4E+05 | 1E+06 | 5E+05 | Library | C | 270 | 109 |
| PEP000042 | 442 | 7E+05 | 8E+04 | 0E+00 | 0E+00 | 412 | 3E+05 | 6E+06 | 6E+05 | Library | C | 1365 | NA |
| PEP000043 | 461 | 3E+05 | 2E+04 | 0E+00 | 0E+00 | 438 | 0E+00 | 0E+00 | 0E+00 | Library | C | NA | NA |
| PEP000044 | 451 | 8E+05 | 1E+05 | 0E+00 | 0E+00 | 427 | 4E+05 | 6E+06 | 8E+05 | Library | C | 1399 | 174 |
| PEP000045 | 433 | 1E+06 | 1E+05 | 0E+00 | 0E+00 | 394 | 7E+05 | 1E+07 | 9E+05 | Library | C | 1893 | 263 |
| PEP000046 | 449 | 1E+06 | 9E+04 | 0E+00 | 0E+00 | 425 | 8E+05 | 1E+07 | 2E+06 | Library | C | 1764 | 167 |
| PEP000047 | 437 | 1E+06 | 1E+05 | 0E+00 | 0E+00 | 401 | 9E+05 | 1E+07 | 5E+05 | Library | C | 1598 | 71 |
| PEP000048 | 453 | 8E+05 | 1E+05 | 0E+00 | 0E+00 | 429 | 4E+05 | 5E+06 | 6E+05 | Library | C | 1080 | 195 |
| PEP000049 | 441 | 8E+05 | 4E+04 | 0E+00 | 0E+00 | 410 | 2E+05 | 5E+06 | 4E+05 | Library | C | 1141 | NA |
| PEP000050 | 458 | 4E+05 | 2E+05 | 0E+00 | 0E+00 | 436 | 9E+04 | 3E+04 | 6E+04 | Library | C | 35 | NA |
| PEP000051 | 439 | 7E+05 | 5E+04 | 0E+00 | 0E+00 | 405 | 2E+05 | 8E+06 | 3E+05 | Library | C | 1631 | NA |
| PEP000052 | 433 | 2E+06 | 6E+04 | 0E+00 | 0E+00 | 394 | 1E+06 | 2E+07 | 1E+07 | Library | C | 1885 | 936 |
| PEP000053 | 457 | 4E+06 | 3E+05 | 0E+00 | 0E+00 | 434 | 1E+06 | 6E+06 | 3E+06 | Library | C | 418 | 216 |
| PEP000054 | 398 | 3E+06 | 5E+04 | 1E+05 | 8E+04 | 367 | 9E+05 | 6E+06 | 3E+06 | Library | C | 700 | 299 |
| PEP000055 | 455 | 4E+05 | 1E+04 | 0E+00 | 0E+00 | 434 | 0E+00 | 1E+06 | 7E+05 | Library | C | NA | NA |
| PEP000056 | 375 | 1E+06 | 7E+04 | 0E+00 | 0E+00 | 340 | 8E+05 | 3E+06 | 7E+05 | Library | C | 377 | 83 |
| PEP000057 | 431 | 2E+06 | 7E+04 | 0E+00 | 0E+00 | 389 | 9E+05 | 1E+07 | 5E+06 | Library | C | 1181 | 589 |
| PEP000058 | 449 | 3E+06 | 1E+04 | 3E+04 | 5E+04 | 425 | 1E+06 | 3E+07 | 1E+07 | Library | C | 1722 | 999 |
| PEP000059 | 389 | 3E+06 | 7E+04 | 3E+04 | 2E+04 | 356 | 1E+06 | 7E+06 | 3E+06 | Library | C | 676 | 313 |
| PEP000060 | 446 | 1E+06 | 1E+05 | 0E+00 | 0E+00 | 422 | 8E+05 | 2E+07 | 8E+06 | Library | C | 1898 | 1005 |
| PEP000061 | 438 | 2E+06 | 1E+05 | 0E+00 | 0E+00 | 405 | 1E+06 | 2E+07 | 7E+06 | Library | C | 1516 | 718 |
| PEP000062 | 382 | 1E+06 | 9E+04 | 0E+00 | 0E+00 | 347 | 6E+05 | 3E+06 | 1E+06 | Library | C | 477 | 168 |
| PEP000063 | 436 | 7E+05 | 6E+04 | 0E+00 | 0E+00 | 400 | 5E+05 | 7E+06 | 3E+06 | Library | C | 1563 | 774 |
| PEP000064 | 433 | 2E+06 | 1E+05 | 0E+00 | 0E+00 | 394 | 9E+05 | 2E+07 | 2E+06 | Library | C | 1980 | 167 |
| PEP000065 | 458 | 2E+06 | 2E+05 | 0E+00 | 0E+00 | 434 | 1E+06 | 4E+06 | 5E+05 | Library | C | 428 | 15 |
| PEP000066 | 450 | 2E+06 | 2E+05 | 0E+00 | 0E+00 | 425 | 1E+06 | 2E+07 | 2E+06 | Library | C | 2170 | 106 |
| PEP000067 | 428 | 2E+06 | 8E+04 | 0E+00 | 0E+00 | 383 | 8E+05 | 5E+06 | 6E+05 | Library | C | 668 | 31 |
| PEP000068 | 449 | 2E+06 | 2E+05 | 0E+00 | 0E+00 | 425 | 1E+06 | 2E+07 | 2E+06 | Library | C | 1965 | 58 |
| PEP000069 | 442 | 2E+06 | 3E+04 | 0E+00 | 0E+00 | 411 | 1E+06 | 3E+07 | 1E+06 | Library | C | 2046 | 33 |
| PEP000070 | 438 | 1E+06 | 5E+04 | 0E+00 | 0E+00 | 405 | 9E+05 | 1E+07 | 1E+06 | Library | C | 1536 | 38 |
| PEP000071 | 365 | 5E+05 | 5E+03 | 0E+00 | 0E+00 | 324 | 3E+05 | 2E+05 | 8E+04 | Library | C | 64 | 27 |
| PEP000072 | 432 | 1E+06 | 1E+05 | 0E+00 | 0E+00 | 392 | 7E+05 | 1E+07 | 1E+06 | Library | C | 1516 | 127 |
| PEP000073 | 436 | 1E+06 | 9E+04 | 0E+00 | 0E+00 | 403 | 1E+06 | 4E+06 | 1E+06 | Library | D | 380 | 94 |
| PEP000074 | 468 | 3E+05 | 7E+04 | 0E+00 | 0E+00 | 443 | 0E+00 | 0E+00 | 0E+00 | Library | D | NA | NA |
| PEP000075 | 457 | 3E+05 | 2E+04 | 0E+00 | 0E+00 | 433 | 0E+00 | 0E+00 | 0E+00 | Library | D | NA | NA |
| PEP000076 | 476 | 3E+04 | 5E+04 | 0E+00 | 0E+00 | 443 | 0E+00 | 0E+00 | 0E+00 | Library | D | NA | NA |
| PEP000077 | 447 | 8E+04 | 3E+04 | 0E+00 | 0E+00 | 425 | 0E+00 | 6E+04 | 8E+04 | Library | D | NA | NA |
| PEP000078 | 459 | 3E+04 | 5E+04 | 0E+00 | 0E+00 | 262 | 0E+00 | 0E+00 | 0E+00 | Library | D | NA | NA |
| PEP000079 | 443 | 2E+06 | 8E+04 | 0E+00 | 0E+00 | 416 | 1E+06 | 4E+06 | 1E+06 | Library | D | 394 | 92 |

-continued

| Peptide | B | C | D | E | F | G | H | I | J | K | L | M | N |
|---|---|---|---|---|---|---|---|---|---|---|---|---|---|
| PEP000080 | 438 | 3E+05 | 2E+04 | 0E+00 | 0E+00 | 410 | 0E+00 | 1E+05 | 1E+05 | Library | D | NA | NA |
| PEP000081 | 444 | 3E+05 | 9E+03 | 0E+00 | 0E+00 | 419 | 0E+00 | 5E+04 | 8E+04 | Library | D | NA | NA |
| PEP000082 | 438 | 4E+05 | 2E+04 | 0E+00 | 0E+00 | 408 | 0E+00 | 1E+06 | 4E+05 | Library | D | NA | NA |
| PEP000083 | 443 | 5E+05 | 4E+04 | 0E+00 | 0E+00 | 418 | 0E+00 | 1E+06 | 3E+04 | Library | D | NA | NA |
| PEP000084 | 462 | 2E+05 | 2E+04 | 0E+00 | 0E+00 | 439 | 2E+05 | 0E+00 | 0E+00 | Library | D | 0 | NA |
| PEP000085 | 432 | 4E+05 | 2E+04 | 0E+00 | 0E+00 | 397 | 0E+00 | 9E+05 | 3E+05 | Library | D | NA | NA |
| PEP000086 | 437 | 5E+05 | 1E+04 | 0E+00 | 0E+00 | 405 | 0E+00 | 8E+05 | 4E+05 | Library | D | NA | NA |
| PEP000087 | 455 | 2E+05 | 1E+05 | 0E+00 | 0E+00 | 431 | 0E+00 | 1E+05 | 5E+04 | Library | D | NA | NA |
| PEP000088 | 445 | 5E+05 | 1E+04 | 0E+00 | 0E+00 | 421 | 0E+00 | 8E+05 | 7E+04 | Library | D | NA | NA |
| PEP000089 | 467 | 3E+05 | 8E+04 | 0E+00 | 0E+00 | 441 | 1E+05 | 0E+00 | 0E+00 | Library | D | 0 | NA |
| PEP000090 | 438 | 5E+05 | 3E+04 | 0E+00 | 0E+00 | 409 | 0E+00 | 2E+06 | 3E+05 | Library | D | NA | NA |
| PEP000091 | 432 | 6E+05 | 4E+04 | 0E+00 | 0E+00 | 397 | 0E+00 | 3E+06 | 8E+05 | Library | D | NA | NA |
| PEP000092 | 442 | 4E+05 | 2E+04 | 0E+00 | 0E+00 | 415 | 0E+00 | 2E+06 | 4E+05 | Library | D | NA | NA |
| PEP000093 | 448 | 1E+05 | 1E+05 | 0E+00 | 0E+00 | 424 | 0E+00 | 9E+05 | 6E+05 | Library | D | NA | NA |
| PEP000094 | 429 | 4E+05 | 4E+04 | 0E+00 | 0E+00 | 391 | 0E+00 | 2E+06 | 6E+05 | Library | D | NA | NA |
| PEP000095 | 438 | 9E+05 | 5E+04 | 0E+00 | 0E+00 | 409 | 7E+05 | 7E+06 | 2E+06 | Library | D | 1026 | 326 |
| PEP000096 | 432 | 5E+05 | 4E+04 | 0E+00 | 0E+00 | 399 | 0E+00 | 1E+06 | 6E+05 | Library | D | NA | NA |
| PEP000097 | 435 | 9E+05 | 5E+04 | 0E+00 | 0E+00 | 404 | 5E+05 | 2E+06 | 1E+06 | Library | D | 274 | NA |
| PEP000098 | 436 | 5E+05 | 5E+03 | 0E+00 | 0E+00 | 406 | 0E+00 | 4E+06 | 7E+05 | Library | E | NA | NA |
| PEP000099 | 442 | 3E+05 | 3E+04 | 0E+00 | 0E+00 | 414 | 0E+00 | 4E+04 | 4E+04 | Library | E | NA | NA |
| PEP000100 | 453 | 3E+05 | 3E+04 | 0E+00 | 0E+00 | 435 | 0E+00 | 0E+00 | 0E+00 | Library | E | NA | NA |
| PEP000101 | 448 | 2E+05 | 2E+04 | 0E+00 | 0E+00 | 280 | 6E+04 | 0E+00 | 0E+00 | Library | E | 0 | NA |
| PEP000102 | 439 | 3E+05 | 2E+04 | 0E+00 | 0E+00 | 413 | 0E+00 | 3E+06 | 4E+05 | Library | E | NA | NA |
| PEP000103 | 445 | 1E+05 | 1E+05 | 0E+00 | 0E+00 | 422 | 0E+00 | 0E+00 | 0E+00 | Library | E | NA | NA |
| PEP000104 | 436 | 9E+05 | 6E+04 | 5E+04 | 9E+04 | 405 | 6E+05 | 2E+07 | 2E+06 | Library | E | 2470 | 195 |
| PEP000105 | 450 | 9E+05 | 8E+04 | 0E+00 | 0E+00 | 430 | 6E+05 | 2E+06 | 1E+05 | Library | E | 346 | 29 |
| PEP000106 | 437 | 2E+06 | 4E+04 | 3E+05 | 1E+05 | 409 | 1E+06 | 3E+07 | 3E+06 | Library | E | 1992 | 228 |
| PEP000107 | 462 | 1E+06 | 2E+04 | 0E+00 | 0E+00 | 438 | 1E+06 | 3E+05 | 5E+05 | Library | E | 21 | 36 |
| PEP000108 | 455 | 6E+05 | 6E+04 | 0E+00 | 0E+00 | 436 | 4E+05 | 0E+00 | 0E+00 | Library | E | 0 | 0 |
| PEP000109 | 428 | 8E+05 | 1E+04 | 4E+05 | 1E+05 | 391 | 7E+05 | 1E+07 | 1E+06 | Library | E | 1989 | 266 |
| PEP000110 | 447 | 8E+05 | 7E+04 | 0E+00 | 0E+00 | 427 | 6E+05 | 3E+06 | 5E+05 | Library | E | 583 | 86 |
| PEP000111 | 434 | 2E+06 | 4E+04 | 0E+00 | 0E+00 | 402 | 1E+06 | 2E+07 | 1E+06 | Library | E | 2339 | 65 |
| PEP000112 | 454 | 8E+05 | 4E+04 | 0E+00 | 0E+00 | 434 | 7E+05 | 6E+05 | 5E+05 | Library | E | 90 | 66 |
| PEP000113 | 439 | 7E+05 | 7E+04 | 0E+00 | 0E+00 | 413 | 0E+00 | 1E+07 | 1E+06 | Library | E | NA | NA |
| PEP000114 | 460 | 4E+05 | 8E+04 | 0E+00 | 0E+00 | 441 | 4E+05 | 0E+00 | 0E+00 | Library | E | 0 | 0 |
| PEP000115 | 431 | 1E+06 | 1E+05 | 0E+00 | 0E+00 | 397 | 6E+05 | 2E+07 | 1E+06 | Library | E | 2804 | 350 |
| PEP000116 | 451 | 1E+07 | 3E+05 | 4E+07 | 1E+06 | 425 | 8E+06 | 4E+07 | 1E+06 | Library | F | 475 | 20 |
| PEP000117 | 448 | 1E+07 | 4E+05 | 1E+05 | 1E+05 | 422 | 7E+06 | 8E+07 | 2E+06 | Library | F | 1141 | 37 |
| PEP000118 | 449 | 1E+07 | 3E+05 | 4E+07 | 1E+06 | 421 | 8E+06 | 4E+07 | 2E+06 | Library | F | 536 | 28 |
| PEP000119 | 458 | 1E+07 | 5E+05 | 1E+07 | 1E+06 | 434 | 6E+06 | 2E+07 | 2E+06 | Library | F | 304 | 39 |
| PEP000120 | 458 | 1E+07 | 6E+05 | 3E+05 | 2E+05 | 433 | 5E+06 | 4E+07 | 2E+06 | Library | F | 757 | 59 |
| PEP000121 | 459 | 1E+07 | 1E+05 | 1E+07 | 8E+05 | 434 | 5E+06 | 2E+07 | 9E+05 | Library | F | 401 | 29 |
| PEP000122 | 451 | 1E+07 | 4E+05 | 8E+06 | 3E+06 | 425 | 8E+06 | 9E+07 | 4E+06 | Library | F | 1188 | 54 |
| PEP000123 | 454 | 1E+07 | 2E+05 | 1E+07 | 3E+06 | 429 | 9E+06 | 9E+07 | 6E+06 | Library | F | 1083 | 69 |
| PEP000124 | 459 | 2E+07 | 1E+06 | 3E+06 | 8E+05 | 433 | 6E+06 | 5E+07 | 6E+05 | Library | F | 745 | 10 |
| PEP000125 | 458 | 1E+07 | 4E+05 | 4E+06 | 1E+06 | 433 | 6E+06 | 5E+07 | 1E+06 | Library | F | 888 | 20 |
| PEP000126 | 460 | 1E+07 | 8E+05 | 4E+06 | 1E+06 | 436 | 7E+06 | 4E+07 | 1E+06 | Library | F | 561 | 24 |
| PEP000127 | 379 | 1E+07 | 4E+05 | 0E+00 | 0E+00 | 327 | 8E+06 | 1E+06 | 3E+05 | Library | G | 17 | 3 |
| PEP000128 | 372 | 5E+06 | 2E+05 | 0E+00 | 0E+00 | 322 | 4E+06 | 1E+05 | 6E+04 | Library | G | 3 | 2 |
| PEP000129 | 374 | 9E+06 | 3E+05 | 0E+00 | 0E+00 | 325 | 6E+06 | 1E+06 | 4E+05 | Library | G | 19 | 6 |
| PEP000130 | 383 | 1E+07 | 5E+05 | 5E+03 | 9E+03 | 333 | 7E+06 | 2E+06 | 3E+05 | Library | G | 27 | 4 |
| PEP000131 | 380 | 6E+06 | 1E+05 | 0E+00 | 0E+00 | 328 | 3E+06 | 1E+05 | 3E+04 | Library | G | 3 | 1 |
| PEP000132 | 383 | 1E+07 | 4E+05 | 0E+00 | 0E+00 | 330 | 6E+06 | 1E+06 | 3E+05 | Library | G | 20 | 4 |
| PEP000133 | 380 | 7E+06 | 7E+05 | 0E+00 | 0E+00 | 330 | 5E+06 | 3E+05 | 1E+05 | Library | G | 5 | 2 |
| PEP000134 | 378 | 8E+06 | 8E+05 | 3E+03 | 5E+03 | 328 | 6E+06 | 1E+05 | 9E+04 | Library | G | 2 | 1 |
| PEP000135 | 385 | 7E+06 | 7E+05 | 0E+00 | 0E+00 | 336 | 5E+06 | 3E+05 | 8E+04 | Library | G | 7 | 2 |
| PEP000136 | 380 | 5E+06 | 5E+05 | 0E+00 | 0E+00 | 328 | 4E+06 | 1E+04 | 3E+03 | Library | G | 0 | 0 |
| PEP000137 | 384 | 9E+06 | 1E+06 | 0E+00 | 0E+00 | 334 | 6E+06 | 4E+05 | 1E+05 | Library | G | 6 | 2 |
| PEP000138 | 466 | 3E+06 | 9E+05 | 5E+06 | 1E+06 | 441 | 2E+06 | 0E+00 | 0E+00 | Library | H | 0 | 0 |
| PEP000139 | 462 | 6E+06 | 1E+06 | 3E+06 | 9E+05 | 443 | 3E+06 | 0E+00 | 0E+00 | Library | H | 0 | 0 |
| PEP000140 | 457 | 2E+06 | 4E+05 | 8E+06 | 2E+06 | 437 | 2E+06 | 6E+05 | 5E+05 | Library | H | 28 | 23 |
| PEP000141 | 461 | 7E+06 | 8E+05 | 3E+06 | 9E+05 | 444 | 2E+06 | 2E+05 | 2E+05 | Library | H | 7 | 8 |
| PEP000142 | 463 | 4E+06 | 1E+06 | 2E+06 | 4E+05 | 450 | 2E+06 | 0E+00 | 0E+00 | Library | H | 0 | 0 |
| PEP000143 | 467 | 5E+06 | 7E+05 | 6E+06 | 3E+06 | 464 | 3E+04 | 5E+05 | 3E+05 | Library | H | 149 | NA |
| PEP000144 | 458 | 6E+06 | 1E+06 | 6E+06 | 1E+06 | 438 | 3E+06 | 9E+05 | 6E+05 | Library | H | 34 | 23 |
| PEP000145 | 459 | 3E+06 | 4E+05 | 4E+06 | 5E+05 | 439 | 2E+06 | 7E+05 | 5E+05 | Library | H | 32 | 20 |
| PEP000146 | 462 | 3E+06 | 9E+05 | 2E+06 | 7E+05 | 446 | 2E+06 | 0E+00 | 0E+00 | Library | H | 0 | 0 |
| PEP000147 | 466 | 5E+06 | 1E+06 | 5E+05 | 3E+05 | 454 | 2E+06 | 0E+00 | 0E+00 | Library | H | 0 | 0 |
| PEP000148 | 476 | 8E+06 | 1E+06 | 4E+06 | 9E+05 | 438 | 2E+06 | 1E+05 | 2E+05 | Library | H | 8 | 10 |
| PEP000149 | 466 | 5E+06 | 2E+05 | 5E+06 | 3E+05 | 441 | 2E+06 | 3E+04 | 5E+04 | Library | H | 2 | 3 |
| PEP000150 | 468 | 5E+05 | 4E+04 | 0E+00 | 0E+00 | 455 | 6E+04 | 0E+00 | 0E+00 | Library | H | 0 | NA |
| PEP000151 | 476 | 1E+06 | 2E+05 | 4E+05 | 1E+05 | 444 | 6E+05 | 6E+04 | 8E+04 | Library | H | 9 | 11 |
| PEP000152 | 466 | 2E+06 | 1E+05 | 0E+00 | 0E+00 | 462 | 5E+05 | 0E+00 | 0E+00 | Library | H | 0 | 0 |
| PEP000153 | 464 | 7E+06 | 4E+05 | 9E+05 | 7E+04 | 445 | 2E+06 | 1E+05 | 1E+05 | Library | H | 6 | 5 |
| PEP000154 | 461 | 4E+05 | 8E+04 | 0E+00 | 0E+00 | 441 | 2E+05 | 0E+00 | 0E+00 | Library | H | 0 | NA |
| PEP000155 | 466 | 1E+06 | 8E+04 | 0E+00 | 0E+00 | 449 | 3E+05 | 0E+00 | 0E+00 | Library | H | 0 | 0 |
| PEP000156 | 461 | 9E+05 | 1E+05 | 1E+06 | 2E+05 | 441 | 5E+05 | 0E+00 | 0E+00 | Library | H | 0 | 0 |

-continued

| Peptide | B | C | D | E | F | G | H | I | J | K | L | M | N |
|---|---|---|---|---|---|---|---|---|---|---|---|---|---|
| PEP000157 | 469 | 1E+06 | 1E+05 | 3E+05 | 2E+04 | 448 | 6E+05 | 0E+00 | 0E+00 | Library | H | 0 | 0 |
| PEP000158 | 476 | 5E+06 | 1E+05 | 2E+06 | 3E+05 | 441 | 2E+06 | 0E+00 | 0E+00 | Library | H | 0 | 0 |
| PEP000159 | 466 | 7E+06 | 2E+05 | 4E+05 | 2E+05 | 449 | 2E+06 | 2E+05 | 2E+05 | Library | H | 17 | 16 |
| PEP000160 | 465 | 2E+05 | 5E+04 | 0E+00 | 0E+00 | 446 | 0E+00 | 0E+00 | 0E+00 | Library | H | NA | NA |
| PEP000161 | 403 | 5E+06 | 9E+05 | 1E+06 | 9E+04 | 366 | 3E+06 | 1E+07 | 4E+05 | Library | I | 360 | 21 |
| PEP000162 | 383 | 2E+06 | 5E+05 | 9E+04 | 6E+04 | 353 | 1E+06 | 4E+06 | 2E+05 | Library | I | 284 | 25 |
| PEP000163 | 428 | 2E+06 | 8E+04 | 1E+05 | 1E+05 | 396 | 1E+06 | 3E+06 | 6E+05 | Library | I | 320 | 37 |
| PEP000164 | 412 | 9E+06 | 1E+06 | 2E+06 | 1E+05 | 374 | 5E+06 | 2E+07 | 8E+05 | Library | I | 425 | 15 |
| PEP000165 | 364 | 1E+06 | 2E+05 | 0E+00 | 0E+00 | 334 | 5E+05 | 9E+05 | 9E+04 | Library | I | 170 | 50 |
| PEP000166 | 370 | 1E+06 | 3E+05 | 3E+03 | 5E+03 | 340 | 9E+05 | 1E+06 | 2E+05 | Library | I | 167 | 25 |
| PEP000167 | 415 | 2E+06 | 2E+05 | 1E+04 | 2E+04 | 377 | 4E+05 | 2E+06 | 3E+05 | Library | I | 289 | NA |
| PEP000168 | 419 | 8E+06 | 4E+05 | 3E+06 | 6E+05 | 383 | 4E+06 | 2E+07 | 2E+06 | Library | I | 427 | 26 |
| PEP000169 | 426 | 1E+07 | 4E+05 | 4E+06 | 5E+05 | 391 | 8E+06 | 4E+07 | 6E+06 | Library | I | 515 | 60 |
| PEP000170 | 374 | 1E+06 | 3E+05 | 4E+04 | 3E+04 | 345 | 8E+05 | 2E+06 | 3E+05 | Library | I | 223 | 39 |
| PEP000171 | 353 | 1E+06 | 6E+04 | 0E+00 | 0E+00 | 322 | 2E+06 | 2E+04 | 3E+04 | Library | I | 2 | 2 |
| PEP000172 | 383 | 5E+06 | 9E+05 | 9E+05 | 1E+05 | 354 | 3E+06 | 8E+06 | 7E+05 | Library | I | 282 | 20 |
| PEP000173 | 362 | 1E+06 | 3E+05 | 1E+04 | 1E+04 | 331 | 1E+06 | 4E+04 | 7E+04 | Library | I | 4 | 8 |
| PEP000174 | 367 | 3E+06 | 5E+05 | 6E+03 | 1E+04 | 337 | 2E+06 | 5E+05 | 1E+05 | Library | I | 23 | 4 |
| PEP000175 | 360 | 4E+06 | 4E+05 | 1E+04 | 9E+03 | 329 | 3E+06 | 9E+04 | 3E+04 | Library | I | 3 | 1 |
| PEP000176 | 363 | 2E+06 | 2E+05 | 6E+04 | 5E+04 | 333 | 8E+05 | 2E+06 | 3E+05 | Library | I | 207 | 40 |
| PEP000177 | 370 | 3E+06 | 5E+05 | 2E+05 | 5E+04 | 340 | 2E+06 | 3E+06 | 4E+05 | Library | I | 211 | 36 |
| PEP000178 | 364 | 4E+06 | 6E+05 | 2E+04 | 3E+03 | 335 | 2E+06 | 2E+05 | 4E+04 | Library | I | 7 | 1 |
| PEP000179 | 371 | 1E+07 | 1E+06 | 9E+04 | 5E+04 | 341 | 5E+06 | 7E+05 | 3E+04 | Library | I | 14 | 1 |
| PEP000180 | 377 | 3E+06 | 4E+05 | 5E+05 | 6E+04 | 348 | 1E+06 | 3E+06 | 2E+05 | Library | I | 225 | 17 |
| PEP000181 | 429 | 6E+06 | 4E+05 | 3E+05 | 1E+05 | 392 | 4E+06 | 4E+07 | 2E+07 | Individual | N/A | 1004 | 404 |
| PEP000182 | 436 | 2E+07 | 2E+06 | 7E+06 | 2E+06 | 399 | 1E+07 | 1E+08 | 4E+07 | Individual | N/A | 779 | 233 |
| PEP000183 | 425 | 2E+07 | 5E+05 | 3E+07 | 5E+06 | 382 | 1E+07 | 6E+07 | 1E+07 | Individual | N/A | 420 | 37 |
| PEP000184 | 436 | 2E+07 | 4E+05 | 4E+07 | 5E+06 | 404 | 1E+07 | 4E+07 | 8E+06 | Individual | N/A | 305 | 66 |
| PEP000185 | 411 | 1E+07 | 3E+06 | 6E+07 | 9E+06 | 364 | 6E+06 | 7E+05 | 2E+05 | Individual | N/A | 12 | 4 |

B: Retention Time of Peptide (seconds) (agents comprising—Cl)
C: Peptide Input Signal (Directly using library mixture; agents comprising—Cl)
D: Peptide Input Signal (SD)
E: Peptide Signal in Cells (from cells; agents comprising—Cl)
F: Peptide Signal in Cells (SD)
G: Retention Time of Mass Shifted Peptide (seconds) (agents comprising—OH)
H: Mass Shifted Peptide Theoretical Max Signal
I: Mass Shifted Peptide Signal in Cells
J: Mass Shifted Peptide Signal in Cells (SD)
K: Experiment Type. Individual = Individual peptide
L: Library (Library Pools A-I)
M: Cell Penetration Score. (N/A - no signal detected in the particular run(s)).
N: Cell Penetration Score (SD)

PEP000116-126 were library based on ATSP-7041 and were cell penetrating. PEP000127-137 were library based on non-penetrating variant of ATSP-7041. PEP000181-184 are certain positive control peptides, and PEP000185 is a negative control peptide.

As confirmed, provided technologies can among other things be utilized to assess permeability of multiple agents with high efficiency.

Structure of certain agents are described below. In various embodiments, such agents comprise stapled peptides moieties. In some embodiments, staples are formed by R8 and S5 through olefin metathesis. In some embodiments, staples are formed by ReN and Az through olefin metathesis.

| SEQ ID NO | | |
|---|---|---|
| 67 | PEP000116 | HaloTag02-Leu-Thr-Phe-R8-Ala-Tyr-Trp-Ala-Gln-Cba-S5-Ser-Ala-Ala-NH2 |
| 68 | PEP000117 | HaloTag02-Leu-Thr-Phe-R8-Glu-Tyr-Trp-Ala-Gln-Cba-S5-Ser-Ala-Ala-NH2 |
| 69 | PEP000118 | HaloTag02-Leu-Thr-Phe-R8-Thr-Tyr-Trp-Ala-Gln-Cba-S5-Ser-Ala-Ala-NH2 |
| 70 | PEP000119 | HaloTag02-Leu-Thr-Phe-R8-Ala-Tyr-Trp-Ala-Gln-Cba-S5-Ser-Ala-Ala-NHMe |
| 71 | PEP000120 | HaloTag02-Leu-Thr-Phe-R8-Glu-Tyr-Trp-Ala-Gln-Cba-S5-Ser-Ala-Ala-NHMe |
| 72 | PEP000121 | HaloTag02-Leu-Thr-Phe-R8-Thr-Tyr-Trp-Ala-Gln-Cba-S5-Ser-Ala-Ala-NHMe |
| 73 | PEP000122 | HaloTag02-Leu-Thr-Phe-R8-Glu-Tyr-Trp-Ala-Ala-Cba-S5-Ser-Ala-Ala-NH2 |

-continued

| SEQ ID NO | | |
|---|---|---|
| 74 | PEP000123 | HaloTagO2-Leu-Thr-Phe-R8-Glu-Tyr-Trp-Ala-Thr-Cba-S5-Ser-Ala-Ala-NH2 |
| 75 | PEP000124 | HaloTagO2-Leu-Thr-Phe-R8-Glu-Tyr-Trp-Ala-Ala-Cba-S5-Ser-Ala-Ala-NHMe |
| 76 | PEP000125 | HaloTagO2-Leu-Thr-Phe-R8-Glu-Tyr-Trp-Ala-Gln-Cba-S5-Ser-Ala-Ala-NHMe |
| 77 | PEP000126 | HaloTagO2-Leu-Thr-Phe-R8-Glu-Tyr-Trp-Ala-Thr-Cba-S5-Ser-Ala-Ala-NHMe |
| 78 | PEP000127 | HaloTagO2-Leu-Thr-Phe-ReN-Ala-Tyr-Trp-Ala-Gln-Cba-Az-Ser-Ala-Ala-NH2 |
| 79 | PEP000128 | HaloTagO2-Leu-Thr-Phe-ReN-Glu-Tyr-Trp-Ala-Gln-Cba-Az-Ser-Ala-Ala-NH2 |
| 80 | PEP000129 | HaloTagO2-Leu-Thr-Phe-ReN-Thr-Tyr-Trp-Ala-Gln-Cba-Az-Ser-Ala-Ala-NH2 |
| 81 | PEP000130 | HaloTagO2-Leu-Thr-Phe-ReN-Ala-Tyr-Trp-Ala-Gln-Cba-Az-Ser-Ala-Ala-NHMe |
| 82 | PEP000131 | HaloTagO2-Leu-Thr-Phe-ReN-Glu-Tyr-Trp-Ala-Gln-Cba-Az-Ser-Ala-Ala-NHMe |
| 83 | PEP000132 | HaloTagO2-Leu-Thr-Phe-ReN-Thr-Tyr-Trp-Ala-Gln-Cba-Az-Ser-Ala-Ala-NHMe |
| 84 | PEP000133 | HaloTagO2-Leu-Thr-Phe-ReN-Glu-Tyr-Trp-Ala-Ala-Cba-Az-Ser-Ala-Ala-NH2 |
| 85 | PEP000134 | HaloTagO2-Leu-Thr-Phe-ReN-Glu-Tyr-Trp-Ala-Thr-Cba-Az-Ser-Ala-Ala-NH2 |
| 86 | PEP000135 | HaloTagO2-Leu-Thr-Phe-ReN-Glu-Tyr-Trp-Ala-Ala-Cba-Az-Ser-Ala-Ala-NHMe |
| 87 | PEP000136 | HaloTagO2-Leu-Thr-Phe-ReN-Glu-Tyr-Trp-Ala-Gln-Cba-Az-Ser-Ala-Ala-NHMe |
| 88 | PEP000137 | HaloTagO2-Leu-Thr-Phe-ReN-Glu-Tyr-Trp-Ala-Thr-Cba-Az-Ser-Ala-Ala-NHMe |

The structure of HaloTagO2 is described below. When utilized in a peptide, its —COOH forms an amide bond with an —$NH_2$ group (e.g., a N-terminal amino group). In some embodiments, a product agent of an agent comprising HaloTagO2 has the same structure as the agent except that the —Cl is replaced with —OH.

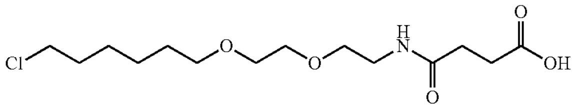 [SMILES: O=C(O)CCC(=O)NCCOCCOCCCCCCCl]

The embodiments of the invention described above are intended to be merely exemplary; numerous variations and modifications will be apparent to those skilled in the art. All such variations and modifications are intended to be within the scope of the present invention as defined in any appended claims.

The invention claimed is:

1. A method, comprising:

contacting an agent with one side of a barrier, wherein the agent has the structure of $R^B$-L-FG2 or a salt thereof, the composition on the other side of the barrier comprises a mutant dehalogenase, and if the agent crosses the barrier, the agent can be covalently bonded to the mutant dehalogenase to form a complex;

hydrolyzing the composition on the other side of the barrier to provide a hydrolysis composition; and detecting by mass spectrometry in the hydrolysis composition for a product agent, wherein the product agent has the structure of $R^P$-L-FG3 or a salt thereof;

wherein:

$R^B$ comprises a stapled peptide moiety;

$R^P$ comprises a stapled peptide moiety;

-L-FG2 is $—C(O)(CH_2)_2C(O)NH(CH_2)_2O(CH_2)_2O(CH_2)_6Cl$; and

-L-FG3 is $—C(O)(CH_2)_2C(O)NH(CH_2)_2O(CH_2)_2O(CH_2)_6OH$.

2. The method of claim 1, wherein a barrier is a cell membrane.

3. The method of claim 1, wherein $R^B$ and $R^P$ are the same.

4. The method of claim 1, wherein a barrier is a monolayer of cells.

5. The method of claim 1, wherein $R^B$ and $R^P$ are the same.

* * * * *